United States Patent
Castro Pineiro et al.

(10) Patent No.: US 7,105,509 B2
(45) Date of Patent: Sep. 12, 2006

(54) BENZODIAZEPINE DERIVATIVES AS APP MODULATORS

(75) Inventors: Jose Luis Castro Pineiro, Bishop's Stortford (GB); Ian Churcher, Great Dunmow (GB); Alexander Richard Guiblin, Cambourne (GB); Timothy Harrison, Great Dunmow (GB); Sonia Kerrard, Harlow (GB); Andrew Madin, Sawbridgeworth (GB); Alan John Nadin, Sawbridgeworth (GB); Andrew Pate Owens, Huntingdon (GB); Timothy Jason Sparey, London (GB); Martin Richard Teall, Bishop's Stortford (GB); Susannah Williams, Harlow (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 326 days.

(21) Appl. No.: 10/296,428

(22) PCT Filed: May 21, 2001

(86) PCT No.: PCT/GB01/02251

§ 371 (c)(1),
(2), (4) Date: Nov. 22, 2002

(87) PCT Pub. No.: WO01/90084

PCT Pub. Date: Nov. 29, 2001

(65) Prior Publication Data

US 2004/0082572 A1    Apr. 29, 2004

(30) Foreign Application Priority Data

May 24, 2000  (GB)  .................. 0012671.4

(51) Int. Cl.
 C07D 243/24  (2006.01)
 C07D 243/12  (2006.01)
 C07D 417/04  (2006.01)
 A61K 31/55   (2006.01)
 A61P 25/28   (2006.01)

(52) U.S. Cl. .............. 514/220; 514/221; 540/506; 540/509; 540/562; 540/572

(58) Field of Classification Search ........ 540/509, 540/506, 562, 572; 514/221, 220
See application file for complete search history.

(56) References Cited

U.S. PATENT DOCUMENTS

| 5,324,726 A | 6/1994 | Bock et al. |
| 5,776,930 A | 7/1998 | Lynch, Jr. et al. |
| 6,632,812 B1 * | 10/2003 | Han et al. .................. 514/221 |
| 2004/0024203 A1 | 2/2004 | Churcher et al. |

FOREIGN PATENT DOCUMENTS

| EP | 167919 | * | 1/1986 |
| EP | 272865 | * | 6/1998 |
| WO | WO 95/14471 | | 6/1995 |
| WO | WO 98/28268 | | 7/1998 |
| WO | WO 00/07995 | | 2/2000 |
| WO | WO 00/14073 | | 3/2000 |
| WO | WO 01/19797 | | 3/2000 |
| WO | WO 00/38618 | | 7/2000 |

OTHER PUBLICATIONS

Fryer et al. (Journal of Organic Chemistry (1977), vol. 42, No. 13, 2212-2219).*
Bell et al. (Journal of Medicinal Chemistry (1968), 11(3), 457-61).*
Selnick et al: Journal of Medicinal Chemistry, US, American Chemical Society. Washington, vol. 24, No. 40, 1997, pp. 3865-3868.
Rittle et al: Terahedron Letters, vol. 28, No. 5, 1987, pp. 521-525.
A Varnavas et al: Farmaco, IT, Societa Chimica Italiana, Pavia, vol. 46, No. 2, 1991, pp. 391-401.

* cited by examiner

*Primary Examiner*—Bruck Kfle
(74) *Attorney, Agent, or Firm*—John C. Todaro; Melvin Winokur

(57) ABSTRACT

A novel class of 1,4- and 1,5-benzodiazepines of formula (I) is disclosed. The compounds modulate the processing of amyloid precursor protein by γ-secretase, and hence find use in the treatment or prevention of conditions associated with the deposition of β-amyloid, such as Alzheimer's disease

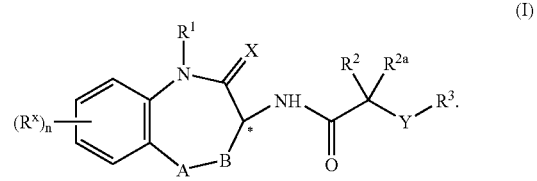

6 Claims, No Drawings

BENZODIAZEPINE DERIVATIVES AS APP MODULATORS

CROSS REFERENCE TO RELATED APPLICATIONS

This application is a U.S. National Phase application under 35 U.S.C. § 371 of PCT Application No. PCT/GB01/02251, filed May 21, 2001, which claims priority under 35 U.S.C. § 119 from GB Application No. 0012671.4, filed May 24, 2000.

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, *ID research alert* 1996 1(2): 1–7; *ID research alert* 1997 2(1):1–8; *Current Opinion in CPNS Investigational Drugs* 1999 1(3):327–332; and *Chemistry in Britain,* Jan. 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release $α-APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood, full length presenilin-1 undergoes cleavage to a C-terminal fragment and an N-terminal fragment.

There are relatively few reports in the literature of compounds with inhibitory activity towards β- or γ-secretase, as measured in cell-based assays. These are reviewed in the articles referenced above. Many of the relevant compounds are peptides or peptide derivatives.

EP-A-167919, WO95/14471 and WO95/14676 disclose classes of 3-acylaminobenzodiazepines which are antiarrhythmic agents, but do not disclose inhibition of γ-secretase or any other modulation of its activity.

The present invention provides a novel class of non-peptidic compounds which are useful in the treatment or prevention of AD by modulating the processing of APP by the putative γ-secretase, thus arresting the production of Aβ.

According to the invention, there is provided the use, for the manufacture of a medicament for the treatment or prevention of a condition associated with the deposition of β-amyloid, of a compound of formula I:

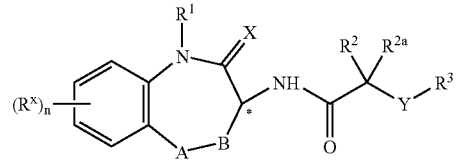

wherein:

n is 0–3;

each $R^x$ independently represents halogen, —CN, —$NO_2$, $C_{1-6}$alkyl, polyfluoro$C_{1-6}$alkyl, —OH or $C_{1-4}$alkoxy;

-A-B- represents:

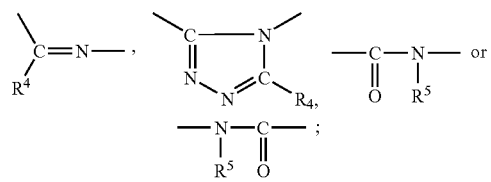

represents O, S or N—$R^a$ where $R^a$ together with $R^1$ completes a fused imidazole or 4,5-dihydroimidazole ring;

Y represents —CH($R^b$)—, —$(CH_2)_x$—CH($OR^c$)—, —CH($CH_2OCOR^b$)—, —CH(NHC(O)$R^b$)—, —$(CH_2)_x$—C(O)—, —$(CH_2)_x$—C(NO$R^b$)—, —CH($OSO_2NH_2$)—, —O— or —S—; where x is 0 or 1, $R^b$ represents H or $C_{1-6}$alkyl or $C_{2-6}$alkenyl, either of which is optionally substituted with halogen, CN, $NO_2$, $CF_3$, OH, $CO_2H$, $C_{1-4}$alkoxy or $C_{1-4}$alkoxycarbonyl, and $R^c$ represents $R^b$ or tris($C_{1-6}$alkyl)silyl;

$R^1$ represents H, $C_{1-6}$alkyl, $C_{3-8}$cycloalkyl, $C_{2-6}$alkenyl, $C_{2-6}$alkynyl or polyfluoro$C_{1-6}$alkyl, said alkyl, cycloalkyl, alkenyl and alkynyl groups being optionally substituted by halogen, —CN, —$NO_2$, aryl, heteroaryl, —$COR^6$, —$CO_2R^6$, —$CON(R^6)_2$, —$OCOR^7$, —$NR^6COR^7$, —$NR^6SO^2R^7$, —$SO_3R^6$, —$SO_2N(R^6)_2$, —$OR^6$, —$SR^6$ or —$N(R^6)_2$; or when X is N—$R^a$, $R^1$ together with $R^a$ completes a fused imidazole or 4,5-dihydroimidazole ring;

$R^2$ represents $C_{1-6}$alkyl, $C_{3-6}$cycloalkyl, $C_{2-6}$alkenyl, $C_{2-6}$alkynyl, polyfluoro$C_{1-6}$alkyl, aryl, heteroaryl, —$OR^7$, —$Oaryl$, —$N(R^8)_2$ or —$NR^6COR^9$, said alkyl, cycloalkyl, alkenyl and alkynyl groups optionally being substituted by halogen, —CN, —$NO_2$, aryl, heteroaryl, —$COR^6$, —$CO_2R^6$, —$CON(R^6)_2$, —$OCOR^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$;

R$^{2a}$ represents H or C$_{1-6}$alkyl;

or R$^2$ and R$^{2a}$ together complete a C$_{3-6}$cycloalkyl group;

R$^3$ represents aryl, heteroaryl, C$_{1-6}$alkyl, polyfluoroC$_{1-6}$alkyl, C$_{3-8}$cycloalkyl or C$_{3-8}$cycloalkylC$_{1-6}$alkyl;

R$^4$ represents H, halogen, —CN, C$_{1-10}$alkyl, C$_{3-10}$cycloalkyl, C$_{2-10}$alkenyl, C$_{2-10}$alkynyl, aryl, heteroaryl, —OR$^8$ or —N(R$^8$)$_2$, said alkyl, cycloalkyl, alkenyl and alkynyl groups optionally being substituted by halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_2$R$^6$, —SO$_2$N(R$^6$)$_2$, —OR$^6$, —SR$^6$ or —N(R$^6$)$_2$;

R$^5$ represents H, C$_{1-6}$alkyl or benzyl which optionally bears up to 3 substituents independently selected from halogen, —CN, —NO$_2$, —OH and methoxy;

each R$^6$ independently represents H, polyfluoroC$_{1-6}$alkyl, or C$_{1-6}$alkyl which is optionally substituted with halogen, —CN, —NO$_2$, —OH, —SH, —NH$_2$, phenyl, morpholin-4-yl, thiomorpholin-4-yl, piperidin-1-yl, piperazin-1-yl, pyrrolidin-1-yl, C$_{1-4}$alkoxy, C$_{1-4}$alkylthio, C$_{1-4}$alkylamino, di(C$_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$; or two R$^6$ groups attached to a single nitrogen atom may complete a heterocyclic ring or condensed ring system of from 3 to 12 members including the said nitrogen, the remaining atoms being selected from C, N, O and S, and the ring or condensed ring system optionally bearing up to 3 substituents independently selected from C$_{1-6}$alkyl, polyfluoroC$_{1-6}$alkyl, C$_{2-7}$acyl, —OH and —CONH$_2$;

R$^7$ represents R$^6$ that is other than H;

R$^8$ represents R$^6$, aryl or heteroaryl;

R$^9$ represents aryl, heteroaryl, C$_{3-6}$cycloalkyl or —OR$^7$;

"aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents independently selected from C$_{1-6}$alkyl [which is optionally substituted with halogen, —CN, —NO$_2$, —OH, —SH, —NH$_2$, C$_{1-4}$alkoxy, C$_{1-4}$alkylthio, C$_{1-4}$alkylamino, di(C$_{1-4}$alkyl)amino, —CO$_2$H, —CO$_2$C$_1$alkyl, —CONH$_2$, —CONHC$_{1-4}$alkyl or —CON(C$_{1-4}$alkyl)$_2$], polyfluoroC$_{1-6}$alkyl, halogen, —CN, —NO$_2$, heteroaryl, —COR$^6$, —CO$_2$R$_6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

"heteroaryl" refers to a heteroaromatic ring of 5 or 6 members, at least one member being nitrogen, oxygen or sulphur and the remainder carbon, said ring optionally being fused to a 5–7 membered saturated or unsaturated ring which may be carbocyclic or may comprise up to 3 heteroatoms selected from nitrogen, oxygen and sulphur, and which may be oxo-substituted, the heteroaromatic ring and optional fused ring together bearing 0–3 substituents independently selected from C$_{1-6}$alkyl [which is optionally substituted with halogen, —CN, —NO$_2$, —OH, —SH, —NH$_2$, C$_{1-4}$alkoxy, C$_{1-4}$alkylthio, C$_{1-4}$alkylamino, di(C$_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoroC$_{1-4}$alkyl, halogen, —CN, —NO$_2$, phenyl, —COR$^6$, —CO$_2$R$^6$, —CON(R$^6$)$^2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

with the proviso that when Y represents —CH(OR$^c$)—, —C(O)— or —C(NOR$^b$)—, R$^3$ represents aryl or heteroaryl;

or a pharmaceutically acceptable salt thereof.

In preferred embodiments, when Y represents —CH(OR$^c$)—, —C(O)— or —C(NOR$^b$)—, R$^3$ represents phenyl which bears 1–3 (preferably 2) substituents selected from Cl, F and CF$_3$.

In a subset of the compounds of formula I:

Y represents —CH$_2$—, —CH(OH)—, —O— or —S;

R$^2$ represents C$_{1-6}$alkyl, C$_{3-6}$cycloalkyl, C$_{2-6}$alkenyl, C$_{2-6}$alkynyl, aryl, heteroaryl, —OR$^7$, —Oaryl, —N(R$^8$)$_2$ or —NR$^6$COR$^9$, said alkyl, cycloalkyl, alkenyl and alkynyl groups optionally being substituted by halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$;

R$^{2a}$ represents H or C$_{1-6}$alkyl;

or R$^2$ and R$^{2a}$ together complete a C$_{3-6}$cycloalkyl group;

and each R$^6$ independently represents H, polyfluoroC$_{1-6}$alkyl, or C$_{1-6}$alkyl which is optionally substituted with halogen, —CN, —NO$_2$, —OH, —SH, —NH$_2$, phenyl, C$_{1-4}$alkoxy, C$_{1-4}$alkylthio, C$_{1-4}$alkylamino, di(C$_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$; or two R$^6$ groups attached to a single nitrogen atom may complete a heterocyclic ring or condensed ring system of from 3 to 12 members including the said nitrogen, the remaining atoms being selected from C, N, O and S, and the ring or condensed ring system optionally bearing up to 3 substituents independently selected from C$_{1-6}$alkyl, polyfluoroC$_{1-6}$alkyl, C$_{2-7}$acyl, —OH and —CONH$_2$.

Preferably, the condition is a neurological disorder having associated β-amyloid deposition, such as Alzheimer's disease.

Also disclosed is a method of treatment of a subject suffering from or prone to Alzheimer's disease which comprises administering to that subject an effective amount of a compound of formula I or a pharmaceutically acceptable salt thereof.

The invention also provides a compound of formula I as defined above, or a pharmaceutically acceptable salt thereof, with the further proviso that when n is 0, and X represents O, and R$^1$ represents H or methyl, and R$^{2a}$ represents H, and R$^3$ represents phenyl, and A-B represents —C(R$^4$)=N— where R$^4$ represents phenyl, R$^2$ does not represent amino or t-butoxycarbonylamino.

The invention further provides a compound as defined in the preceding paragraph, or a pharmaceutically acceptable salt thereof, for use in treatment of the human or animal body, in particular for use in treatment of a condition associated with deposition of β-amyloid. Preferably, the condition is a neurological disorder having associated β-amyloid deposition, such as Alzheimer's disease.

The invention also provides a pharmaceutical composition comprising one or more compounds of the invention or pharmaceutically acceptable salts thereof and a pharmaceutically acceptable carrier.

Where a variable occurs more than once in formula I or in a substituent thereof, the individual occurrences of that variable are independent of each other, unless otherwise specified.

As used herein, the expression "C$_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "polyfluoro$C_{1-6}$alkyl" as used herein refers to alkyl groups as defined above comprising at least one —$CF_2$— and/or —$CF_3$ group.

The expression "$C_{2-7}$acyl" as used herein refers to aromatic or linear, branched or cyclic aliphatic keto groups of up to 7 carbon atoms including the carbonyl group. Halogenated derivatives are encompassed. Examples include acetyl, trifluoroacetyl, benzoyl, n-propanoyl, isopropanoyl and cyclopentanoyl.

As used herein, the expression "$C_{3-x}$cycloalkyl" where x is an integer greater than 3 refers to nonaromatic hydrocarbon ring systems comprising from 3 to x ring atoms. Where the specified number of ring atoms permits, the definition includes polycyclic systems, including spirocyclic, ortho-fused (including benzo-fused, provided attachment of the cycloalkyl group is via the non-aromatic ring) and bridged bicyclic systems. "Spirocyclic" refers to a pair of rings having a single atom in common. "Ortho-fused" refers to a pair of rings having two adjacent atoms in common. "Bridged bicyclic" refers to a pair of rings having at least three adjacent atoms in common. Examples of cycloalkyl groups therefore include cyclopropyl, cyclobutyl, cyclopentyl, cyclohexyl, cyclohexenyl, indanyl, decalinyl, and bicyclo[2,2,1]hept-1-yl.

As used herein, the expression "heterocyclic ring system" refers to monocyclic or condensed ring systems comprising ring atoms selected from carbon, oxygen, nitrogen and sulphur, at least one ring being nonaromatic and comprising at least one ring atom which is other than carbon. The condensed ring systems include spirocyclic, ortho-fused and bridged bicyclic systems. Benzo-fused systems are included, provided attachment of the heterocyclic ring system is via the nonaromatic ring. Examples include azetidine, pyrrolidine, piperidine, piperazine, morpholine, thiomorpholine, tetrahydrofuran, tetrahydrothiophene, indoline and 3-azabicyclo[3,2,2]nonane.

As used herein, the expression "aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents as described previously. The definition thus includes substituted and unsubstituted phenyl and naphthyl groups, and also groups comprising a phenyl ring which is fused to a saturated or unsaturated carbocyclic or heterocyclic ring, provided attachment of the aryl group is via the phenyl ring. The fused ring may be oxo-substituted, and henc may be a cyclic lactone or lactam. Examples of aryl groups therefore also include methylenedioxyphenyl, quinolinyl, 1,2,3,4-tetrahydroquinolinyl, benzofuranyl, indolyl and 1-oxoisoindolyl.

As used herein, the expression "heteroaryl" refers to a heteroaromatic zing of 5 or 6 members, at least one member being nitrogen, oxygen or sulphur and the remainder carbon, said ring optionally being fused to a 5–7 membered saturated or unsaturated zing which may be carbocyclic or may comprise up to 3 heteroatoms selected from nitrogen, oxygen and sulphur, and which may be oxo-substituted, the heteroaromatic ring and optional fused ring together bearing 0–3 substituents as described previously. Generally, not more than 4, and preferably not more than 3 atoms of the heteroaromatic ring are other than carbon. Where a heteroaromatic ring comprises two or more atoms which are not carbon, not more than one of said atoms may be other than nitrogen. Examples of heteroaromatic rings include pyridine, pyridazine, pyrimidine, pyrazine, pyrrole, furan, thiophene, pyrazole, oxazole, isoxazole, thiazole, isothiazole, imidazole, oxadiazole, triazole, thiadiazole, tetrazole, 1,2,4-triazine and 1,3,5-triazine. The optional fused ring may be saturated or unsaturated, including rings which are themselves (hetero)aromatic. Thus, for example, benzo-fused derivatives of the above-listed heteroaromatic rings (where they are possible) are included within the definition, provided attachment of the heteroaryl group is via the heteroaromatic ring.

When a hydroxy substituent is present on a heteroaromatic ring and keto-enol tautomerism is possible, both tautomers are to be considered as falling within the scope of the invention.

The term "halogen" as used herein includes fluorine, chlorine, bromine and iodine.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention. However, the stereochemistry at the position marked with an asterisk (*) in formula I is preferably as shown in formula Ia:

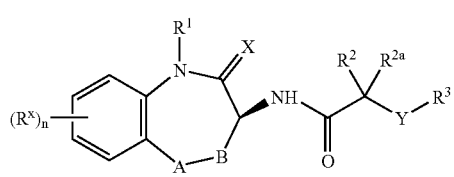

Ia

In the compounds of formula I, n is preferably 0–2, most preferably 0 or 1.

$R^x$ is preferably halogen or $C_{1-6}$alkyl, most preferably halogen, especially chlorine. When n is 1, the substituent $R^x$ is preferably in the 7-position (i.e. para with respect to the nitrogen atom bonded to $R^1$).

Preferably, -A-B- represents

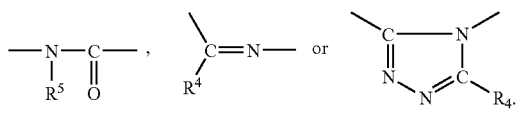

Most preferably, -A-B- represents —C(R$^4$)=N— or —N(R$^5$)—CO—.

X represents O, S or N—R$^a$ where R$^a$ combines with R$^1$ to complete a fused imidazole or 4,5-dihydroimidazole ring. Typically, X is O or N—R$^a$, and preferably X is O.

Y represents —CH(R$^b$)—, —(CH$_2$)$_x$—CH(OR$^c$)—, —CH(CH$_2$OCOR$^b$)—, —CH(NHC(O)R$^b$)—, —(CH$_2$)$_x$—C(O)—, —(CH$_2$)$_x$—C(NOR$^b$)—, —CH(OSO$_2$NH$_2$)—, —O— or —S—; where x is 0 or 1, R$^b$ represents H or C$_{1-6}$alkyl or C$_{2-6}$alkenyl, either of which is optionally substituted with halogen, CN, NO$_2$, CF$_3$, OH, CO$_2$H, C$_{1-4}$alkoxy or C$_{1-4}$alkoxycarbonyl, and R$^c$ represents R$^b$ or tris(C$_{1-6}$alkyl)silyl. Typically, R$^b$ represents H, C$_{1-4}$alkyl (such as methyl, ethyl or propyl), C$_{2-4}$alkenyl (such as vinyl or allyl) or substituted alkyl (such as bromomethyl, hydroxymethyl or carboxyethyl). Typically, R$^c$ represents H, C$_{1-4}$alkyl (such as methyl) or tris(C$_{1-6}$alkyl)silyl (especially t-butyldimethylsilyl). Examples of groups represented by Y include —CH$_2$—, —CH(OH)—, —O—, —CH$_2$CH(OH)—, —CH$_2$C(O)—, —C(O)—, —CH(OCH$_3$)—, —CH[OSi(Me)$_2$$^t$Bu]—, —CH(CH$_2$OH)—, —CH(CH$_2$OCOCH$_2$CH$_2$CO$_2$H)—, —CH(CH$_2$CH$_3$)—, —CH(CH$_2$Br)—, —CH(CH=CH$_2$)—, —C(=NOH)—, —CH(NHCHO)— and —CH(OSO$_2$NH$_2$)—. Preferred embodiments of Y include —CH$_2$—, —CH(OH)—, —O—, —CH(CH$_2$OH)—, —CH(CH$_2$OCOCH$_2$CH$_2$CO$_2$H)—, —CH(OCH$_3$)—, —CH(CH$_2$Br)—, —CH[OSi(Me)$_2$$^t$Bu]— and —C(=NOH)—.

Typically, R$^1$ represents H, polyfluoroC$_{1-6}$alkyl or C$_{1-6}$alkyl which is optionally substituted with halogen, CN, heteroaryl, —CO$_2$R$^6$, —CON(R$^6$)$_2$, —OR$^7$ or —N(R$^6$)$_2$ where heteroaryl, R$^6$ and R$^7$ are as defined above, or R$^1$ combines with X to complete a fused imidazole or 4,5-dihydroimidazole ring. Preferably, R$^1$ represents H, polyfluoroC$_{1-6}$alkyl or C$_{1-4}$alkyl which is optionally substituted with —CN, —OH, halogen, aryl, heteroaryl, —N(R$^6$)$_2$, —CON(R$^6$)$_2$, —CO$_2$R$^6$, —COR$^6$, —OCOR$^6$, C$_{1-6}$alkoxy or di(C$_{1-6}$alkyl)amino, or R$^1$ combines with X to complete a fused imidazole or 4,5-dihydroimidazole ring. Specific embodiments of R$^1$ include H, methyl, isopropyl, 2,2,2-trifluoroethyl, cyanomethyl, carbamoylmethyl, N-methylcarbamoylmethyl, N,N-dimethylcarbamoylmethyl, N-ethylcarbamoylmethyl, N-isopropylcarbamoylmethyl, N-t-butylcarbamoylmethyl, pyrrolidin-1-ylcarbonylmethyl, morpholin-4-ylcarbonylmethyl, 2-carbamoylethyl, pyridylmethyl, 5-chloro-1,2,3-thiadiazol-4-ylmethyl, 4-methoxybenzyl, 2-oxopropyl, 3-hydroxypropyl, 2-hydroxy-2-methylpropyl, 2-bromo-2-methylpropyl, 2-hydroxyethyl, 2-acetoxyethyl, methoxycarbonylmethyl, 3-(morpholin-4-yl)propyl and 3-dimethylaminopropyl. Preferred embodiments of R$^1$ include H, methyl, carbamoylmethyl, pyridylmethyl and 2,2,2-trifluoroethyl.

R$^2$ represents C$_{1-6}$alkyl, C$_{3-6}$cycloalkyl, C$_{2-6}$alkenyl, C$_{2-6}$alkynyl, polyfluoroC$_{1-6}$alkyl, aryl, heteroaryl, —OR$^7$, —Oaryl, —N(R$^8$)$_2$ or —NR$^6$COR$^9$, wherein the alkyl, cycloalkyl, alkenyl and alkynyl groups optionally bear a substituent selected from halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$, where R$^6$, R$^7$, R$^8$ and R$^9$ are as defined above. Typically, R$^2$ represents C$_{1-6}$alkyl (which is optionally substituted by halogen, CN, —CO$_2$R$_6$, —OR$^6$ or —N(R$^6$)$_2$), C$_{3-6}$cycloalkyl, C$_{2-6}$alkenyl, aryl, heteroaryl, —OR$^7$, phenoxy, —N(R$^6$)$_2$ or —NHCOR$^9$. Preferably, R$^2$ represents C$_{1-6}$alkyl, di(C$_{1-6}$alkyl)aminoC$_{1-6}$alkyl, C$_{3-6}$cycloalkyl, C$_{2-6}$alkenyl, aryl, heteroaryl, C$_{1-6}$alkoxy, —N(R$^6$)$_2$ or C$_{1-6}$alkoxycarbonylamino.

Examples of alkyl and substituted alkyl groups represented by R$^2$ include methyl, ethyl, isopropyl, isobutyl and dimethylaminomethyl.

Examples of cycloalkyl groups represented by R$^2$ include cyclopropyl, cyclopentyl and cyclohexyl.

Examples of alkenyl groups represented by R$^2$ include allyl.

Examples of alkynyl groups represented by R$^2$ include propargyl.

Examples of polyfluoroC$_{1-6}$alkyl groups represented by R$^2$ include trifluoromethyl and 2,2,2-trifluoroethyl.

Typical aryl groups represented by R$^2$ include phenyl bearing 0–3 (preferably 0–2) substituents selected from halogen, C$_{1-6}$alkyl, CN, methoxy, trifluoromethyl and —OH. Preferred examples include phenyl, chlorophenyl, bromophenyl and fluorophenyl, the substituent occupying any of the available positions, but the para-position being preferred, and difluorophenyl, especially 2,5-difluorophenyl.

Typical heteroaryl groups represented by R$^2$ include optionally substituted pyridyl, thienyl, furyl, thiazolyl, oxazolyl and isoxazolyl. Typical substituents (where present) include halogen, C$_{1-6}$alkyl, CN, methoxy and trifluoromethyl. Preferred examples of heteroaryl groups represented by R$^2$ include 4-pyridyl, 2-thienyl, 3-thienyl and 2-methylthiazol-4-yl.

Examples of C$_{1-6}$alkoxy groups represented by R$^2$ include methoxy, ethoxy and n-butoxy. A preferred example is methoxy.

When R$^2$ represents —N(R$^6$)$_2$, each R$^6$ independently represents H, polyfluoroC$_{1-6}$alkyl or optionally substituted C$_{1-6}$alkyl, or the R$^6$ groups together with the nitrogen to which they are attached form a heterocyclic ring or condensed ring system. Typically, the R$^6$ groups represent H or C$_{1-6}$alkyl, or together complete a heterocyclic ring or condensed ring system. Examples of —N(R$^6$)$_2$ groups represented by R$^2$ include amino, dimethylamino, pyrrolidinyl and 1,3-dihydroisoindol-2-yl.

When R$^2$ represents —NHCOR$^9$, R$^9$ preferably represents —OR$^7$ and R$^7$ preferably represents t-butyl or benzyl.

Preferred values of R$^2$ include methyl, isopropyl, isobutyl, cyclopropyl, allyl, phenyl, fluorophenyl, bromophenyl, difluorophenyl, pyridyl, thienyl, 2-methylthiazol-4-yl, amino, dimethylamino, dimethylaminomethyl, pyrrolidinyl, 1,3-dihydroisoindol-2-yl, t-butoxycarbonylamino and methoxy, and in particular methyl, phenyl, thienyl, 4-fluorophenyl and 2,5-difluorophenyl.

R$^{2a}$ represents H or C$_{1-6}$alkyl, preferably H or C$_{1-4}$alkyl, and in particular H or methyl. Most preferably, R$^{2a}$ represents H.

Alternatively, R$^2$ and R$^2$a together may complete a cycloalkyl ring such as cyclopropyl, cyclopentyl or cyclohexyl.

R$^3$ may represent aryl, heteroaryl, C$_{1-6}$alkyl, polyfluoroC$_{1-6}$alkyl, C$_{3-8}$cycloalkyl or C$_{3-8}$cycloallylC$_{1-6}$alkyl, and typically represents C$_{1-6}$alkyl (such as n-propyl), polyfluoroC$_{1-6}$alkyl (such as CF$_3$), aryl or heteroaryl. In particular, R$^3$ represents phenyl which optionally bears up to 3, but preferably not more than 2, substituents selected from halogen atoms and trifluoromethyl. Preferred embodiments of $R^3$ include phenyl, chlorophenyl, fluorophenyl, (trifluoromethyl)phenyl, fluoro(trifluoromethyl)phenyl, dichlorophenyl and difluorophenyl. Particularly preferred embodiments include 2,4-dichlorophenyl, 2,4-difluorophenyl, 3,4-dichlorophenyl, 3,4-difluorophenyl, 4-(trifluoromethyl)phenyl, 3-fluoro-4-(trifluoromethyl)phenyl and 4-fluoro-3-(trifluoromethyl)phenyl.

$R^4$ represents H, halogen, —CN, $C_{1-10}$alkyl, $C_{3-10}$cycloalkyl, $C_{2-10}$alkenyl, $C_{2-10}$alkynyl, aryl, heteroaryl, —$OR^8$ or —$N(R^8)_2$, said alkyl, cycloalkyl, alkenyl and alkynyl groups being optionally substituted as described previously. Typically, $R^4$ represents halogen (especially Cl), optionally substituted alkyl, optionally substituted cycloalkyl, aryl, heteroaryl or —$N(R^8)_2$.

Alkyl groups represented by $R^4$ are typically unsubstituted or substituted by a carbamoyl group. Examples include methyl, ethyl, isopropyl and t-butyl.

Cycloalkyl groups represented by $R^4$ include cyclopropyl, cyclobutyl, cyclopentyl, cyclohexyl, cycloheptyl and bicyclo[2,2,1]heptyl.

Aryl groups represented by $R^4$ are typically phenyl groups, optionally substituted with up to 3 halogen atoms or with up to 2 substituents selected from $C_{1-6}$alkyl, $C_{1-6}$alkoxy, polyfluoro$C_{1-6}$alkyl, polyfluoro$C_{1-6}$alkoxy, a carbamoyl group, an aminosulphonyl group and a heteroaryl group. Alternatively or additionally, a phenyl group embodying $R^4$ may have a saturated or unsaturated ring fused thereto. Examples of suitable fused rings include 1,3-dioxolane, 2,2-difluoro-1,3-dioxolane, pyridine, cyclopentanone, cyclohexanone, cyclopentene, 1,4-dioxan, pyranone and 5- or 6-membered cyclic lactams. Typical heteroaryl substituents include pyrazolyl, triazolyl, thiazolyl and isoxazolyl, especially pyrazolyl. Particular examples of aryl groups represented by $R^4$ include phenyl, bromophenyl, chlorophenyl, fluorophenyl, methoxyphenyl, aminosulphonylphenyl, trifluoromethylphenyl, trifluoromethoxyphenyl, carbamoylphenyl, 3,4-dichlorophenyl, 3-chloro4-methoxyphenyl, 3,4-methylenedioxyphenyl, 3,4-(difluoromethylene)dioxyphenyl, quinolin-5-yl, 4oxo-4H-chromen-7-yl, 1-indanone-5-yl, 3-methyl-1H-indene-6-yl, 5-oxo-5,6,7,8-tetrahydronaphthalen-2-yl 1,4-benzodioxan-6-yl, 1-oxo-2,3-dihydro-1H-isoindol-5-yl, 1-oxo-1,2,3,4-tetrahydroisoquinolin-6-yl, 2-oxo-1,2,3,4-tetrahydroquinolin-6-yl, 2-methyl-1-oxo-1,2,3,4-tetrahydroisoquinolin-6-yl, and 1-oxo-1,2-dihydroisoquinolin-6-yl.

Typical heteroaryl groups represented by $R^4$ include pyridyl, pyrimidinyl, pyrrolyl, pyrazolyl, furyl, thienyl and benzo-fused derivatives thereof, optionally substituted with halogen, carbamoyl, methoxy or $C_{1-6}$alkyl. Specific examples include pyrazol-3-yl, benzothiophene-2-yl, 4-pyridyl, 2-methoxy-4-pyridyl and pyrimidin-5-yl.

When $R^4$ represents —$N(R^8)_2$, each $R^8$ typically is independently selected from H, optionally substituted $C_{1-6}$alkyl, aryl or heteroaryl, or the two $R^8$ groups together with the nitrogen to which they are attached complete an optionally substituted heterocyclic ring or condensed ring system. Examples of —$N(R^8)_2$ represented by $R^4$ therefore include amino, methylamino, dimethylamino, benzylamino, carbamoylbenzylamino, anilino and carbamoylphenylamino. Very aptly, the two $R^8$ groups complete a heterocyclic ring or condensed ring system of 3–12 members including the nitrogen to which the $R^8$ groups are attached, the remaining atoms being selected from C, O, N and S, and the ring or condensed ring system optionally bearing up to 3 substituents selected from $C_{1-6}$alkyl, polyfluoro$C_{1-6}$alkyl, —OH, $C_{2-7}$acyl and —$CONH_2$. Examples of suitable heterocyclic rings include aziridine, azetidine, pyrrolidine, piperidine, piperazine, morpholine and thiomorpholine. Examples of suitable heterocyclic condensed ring systems include 3-azabicyclo[3,2,2]nonane and 1,4-dioxa-8-azaspiro[4,5]decane. Typical optional substituents include methyl, trifluoromethyl, acetyl, hydroxyl and carbamoyl. Preferred heterocyclic groups represented by $R^4$ include azetidinyl, pyrrolidinyl, piperidinyl, morpholinyl, 2,6-dimethylmorpholin-4-yl, 4-methylpiperidin-1-yl, 4-carbamoylpiperidin-1-yl, 4-trifluoromethylpiperidinyl, 2,4,6-trimethylpiperidinyl, 3-azabicyclo[3,2,2]nonan-3-yl and 1,4-dioxa-8-azaspiro [4,5]decan-8-yl.

Particular embodiments of $R^4$ include isopropyl, cyclopropyl, cyclobutyl, cycloheptyl, phenyl, 4-bromophenyl, 4-methoxyphenyl, 4-carbamoylphenyl, 3,4-methylenedioxyphenyl, 3,4-(difluoromethylene)dioxyphenyl, 1,4-dioxa-8-azaspiro[4,5]decan-8-yl, 4-oxo-4H-chromen-7-yl, 1-indanone-5-yl, 3-methyl-1H-indene-6-yl, 5-oxo-5,6,7,8-tetrahydronaphthalen-2yl, 1,4-benzodioxan-6-yl, 1-oxo-2,3-dihydro-1H-isoindol-5-yl, 1-oxo-1,2,3,4-tetrahydroisoquinolin-6-yl and 1-oxo-1,2dihydroisoquinolin-6-yl.

Typically, $R^5$ represents H, $C_{1-6}$alkyl or optionally substituted benzyl. Particular embodiments of $R^5$ include H, methyl, isopropyl, benzyl and trimethoxybenzyl.

A subset of the compounds of formula I are in accordance with formula II:

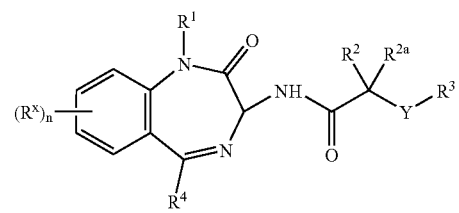

wherein n, Y, $R^x$, $R^1$, $R^2$, $R^{2a}$, $R^3$ and $R^4$ have the same meanings as before.

A subclass of the compounds of formula II are in accordance with formula IIa:

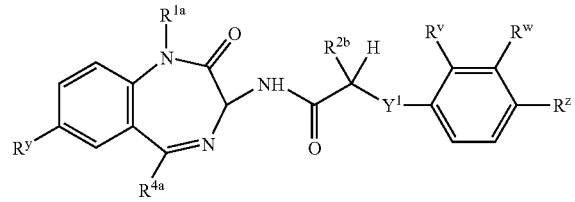

wherein:
$R^y$, $R^z$, $R^v$ and $R^w$ are independently H, $CF_3$ or halogen;
$Y^1$ is —$CH(R^b)$—, —$CH(OR^c)$—, —$CH(CH_2OCOR^b)$—, —$CH(NHC(O)R^b)$—, —$C(O)$—, —$C(NOR^b)$— or —O—;
$R^{1a}$ is H, polyfluoro$C_{1-4}$alkyl, or $C_{1-4}$alkyl which is optionally substituted by —OH, —CN, halogen, aryl, heteroaryl, carbamoyl, N—($C_{1-4}$alkyl)carbamoyl, N,N-di($C_{1-4}$alkyl)carbamoyl or dimethylamino;
$R^{2b}$ is selected from $C_{1-6}$alkyl, $C_{3-6}$cycloalkyl, polyfluoro$C_{1-6}$alkyl, $(R^{6a})_2N$—$C_{1-6}$alkyl, $C_{2-6}$alkenyl, heteroaryl, $C_{1-6}$alkoxy, $-N(R^{6a})_2$, $-NHCO_2R^{7a}$, and phenyl which is optionally substituted by halogen;

$R^{4a}$ is selected from $C_{1-10}$alkyl, $C_{3-10}$cycloalkyl, $-N(R^{6a})_2$, pyridyl which is optionally substituted by methoxy; or phenyl which is optionally substituted by up to 2 groups selected from halogen, methoxy, $CF_3$, $OCF_3$ and carbamoyl or which is fused to a heterocyclic ring or to an oxo-substituted carbocyclic ring;

each $R^{6a}$ independently represents H or $C_{1-6}$alkyl which is optionally substituted with $-CONH_2$, or two $R^{6a}$ groups together with a nitrogen atom to which they are commonly attached complete a heterocyclic ring or condensed ring system of 3–12 members including the said nitrogen, the remaining atoms being selected from C, O, N and S, and the ring or condensed ring system optionally bearing up to 3 substituents selected from $C_{1-6}$alkyl, polyfluoro$C_{1-6}$alkyl, $-OH$, and $-CONH_2$; and $R^{7a}$ represents t-butyl or benzyl.

Typically, $Y^1$ is $-CH_2-$, $-CH(OH)-$, $-O-$, $-CH(CH_2OH)-$, $-CH(CH_2OCOCH_2CH_2CO_2H)-$, $-CH(OCH_3)-$, $-CH(CH=CH_2)-$, $-CH(CH_2Br)-$ or $-C(=NOH)-$.

Typically, $R^{4a}$ is $C_{1-6}$alkyl, $C_{3-7}$cycloalkyl, $-N(R^{6a})_2$, pyridyl which is optionally substituted by methoxy; or phenyl which is optionally substituted by up to 2 groups selected from halogen, methoxy, $CF_3$, $OCF_3$ and carbamoyl or which is fused to a ring selected from 1,3-dioxolane, 2,2-difluoro-1,3-dioxolane, pyridine, cyclopentanone, cyclohexanone, cyclopentene, 1,4-dioxan, pyranone and 5- or 6-membered cyclic lactams.

In a subset of the compounds of formula IIa,
$R^y$, $R^z$, $R^v$ and $R^w$ are independently H or halogen;
$Y^1$ is $-CH_2-$, $-CH(OH)-$ or $-O-$;
$R^{1a}$ is H, polyfluoro$C_{1-4}$alkyl, or $C_{1-4}$alkyl which is optionally substituted by $-OH$, $-CN$, carbamoyl or dimethylamino;
$R^{2b}$ is selected from $C_{1-6}$alkyl, $(R^{6a})_2N-C_{1-6}$alkyl, $C_{2-6}$alkenyl, heteroaryl, $C_{1-6}$alkoxy, $-N(R^{6a})_2$, $-NHCO_2R^{7a}$, and phenyl which is optionally substituted by halogen; and
$R^{4a}$ is selected from $-N(R^{6a})_2$; phenyl which is optionally substituted by halogen or carbamoyl or which is optionally fused to a 5- or 6-membered cyclic lactam; or pyridyl which is optionally substituted by methoxy.

Another subset of the compounds of formula IIa is defined by formula IIb:

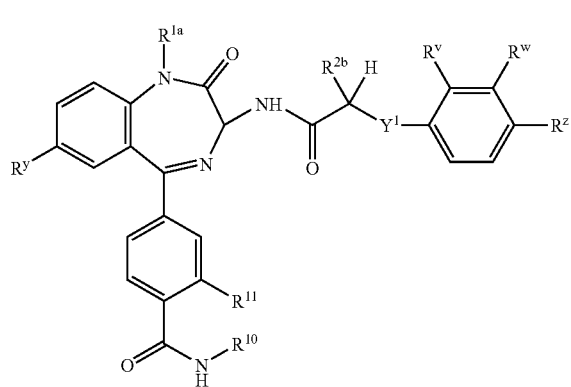

IIb wherein $R^{10}$ and $R^{11}$ are both H, or $R^{10}$ and $R^{11}$ together complete a 5- or 6-membered cyclic lactam; and $R^y$, $R^z$, $R^v$, $R^w$, $Y^1$, $R^{1a}$ and $R^{2b}$ have the same meanings as before.

A further subset of the compounds of formula I are in accordance with formula IIc:

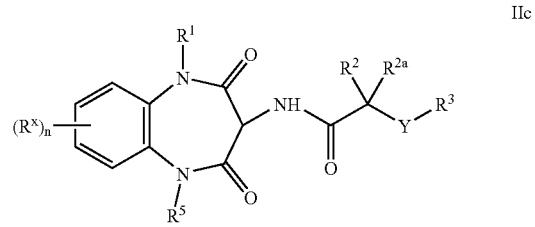

IIc where n, $R^x$, Y, $R^1$, $R^2$, $R^{2a}$, $R^3$ and $R^5$ have the same meanings as before.

Preferred compounds of formula IIc are in accordance with formula IId:

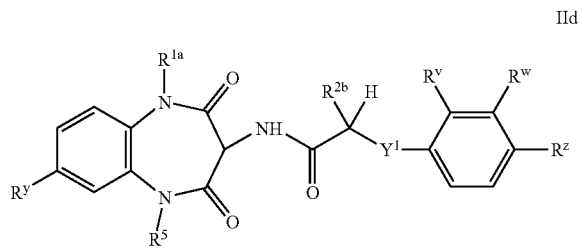

IId where $R^y$, $R^z$, $R^v$, $R^w$, $Y^1$, $R^{1a}$, $R^{2b}$ and $R^5$ have the same meanings as before.

In the compounds of formulae IIa, IIb and IId, preferably $R^z$ is halogen or $CF_3$ and one of $R^v$ and $R^w$ is H while the other is halogen or $CF_3$. Preferably, not more than 1 of $R^z$, $R^v$ and $R^w$ represents $CF_3$. In one preferred embodiment, $R^z$ and $R^w$ are both chlorine or both fluorine and $R^v$ is H. In another preferred embodiment, one of $R^z$ and $R^w$ is $CF_3$ while the other is fluorine and $R^v$ is H. $R^y$ is preferably H or chlorine, most preferably H.

In particular embodiments of the compounds of formulae IIa, IIb and IId, $Y^1$ represents $-CH(CH_2OH)-$.

Examples of compounds useful in the invention include those disclosed in the Examples appended hereto, and pharmaceutically acceptable salts thereof.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

Synthesis of the compounds of formula I typically involves the coupling of a 3-aminobenzodiazepine derivative with a carboxylic acid as described below. Suitable routes to the relevant aminobenzodiazepines are disclosed, for example, in *J. Org. Chem.* 1987, 52, 3232; *J. Org. Chem.* 1995, 60, 730; *J. Med. Chem.* 1993, 36, 4276; *J. Med. Chem.* 1994, 37, 719; *Bioorg. & Med. Chem. Letts.* 1993, 3, 1919; *J. Chem. Soc., Perkin Trans* 1 1995, 203; *Synthesis,* 1994, 505; *Synthesis,* 1980, 677; WO93/07131; WO94/03437; WO95/14471; WO95/14473; WO96/40655; WO97/48686 and EP284256.

Key intermediates in the synthesis of many of the compounds of the invention are the compounds in accordance with formula III:

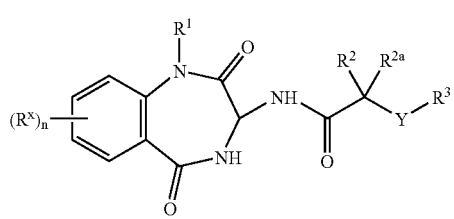

III wherein $R^x$, n, $R^1$, $R^2$, $R^{2a}$, $R^3$ and Y have the same meanings as before. The compounds of formula III are themselves compounds of the invention, being compounds of formula I in which X is O, -A-B- represents —C(O)—N($R^5$)— and $R^5$ is H.

Compounds of formula III may be prepared by reaction of a compound of formula IV with a compound of formula V:

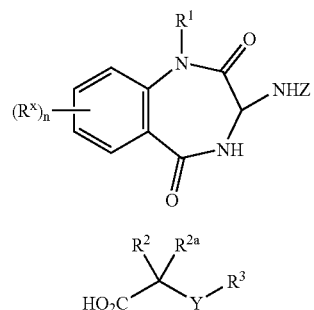

IV

V wherein Z represents benzyloxycarbonyl and $R^x$, n, $R^1$, $R^2$, $R^{2a}$, $R^3$ and Y have the same meanings as before. The compound of formula IV is first treated with acid (e.g. HBr in acetic acid) to remove the protecting group Z, and the resulting primary amine is coupled with the carboxylic acid V to form amide III. Any of the standard coupling methods may be used, such as treatment with 1-(3-dimethylaminopropyl)-3-ethylcarbodiimide hydrochloride (EDC), hydroxybenzotriazole hydrate (HOBt) and triethylamine in dichloromethane, or treatment with O-benzotliazol-1-yl-N, N,N',N'-tetramethyluronium hexafluorophosphate (HBTU) and triethylamine in acetonitrile.

Compounds of formula IV are obtainable by cyclising compounds of formula VI:

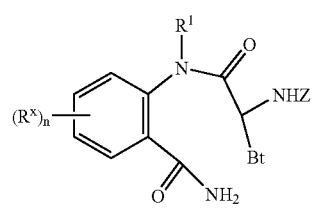

VI wherein Bt represents benzotriazol-1-yl and Z, $R^x$, n and $R^1$ have the same meanings as before. The cyclisation may be effected by heating at about 180° C. in a solvent such as DMSO for about 20 minutes.

Compounds of formula VI are obtainable by coupling of a compound of formula VII with compound VIII:

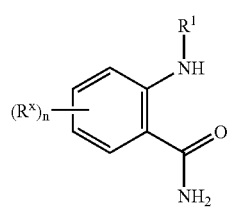

VII

-continued

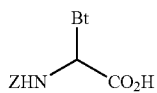

VIII wherein Bt, Z, $R^x$, n and $R^1$ have the same meanings as before. The carboxylic acid group of VIII is first converted to the acid chloride (e.g. by treatment with oxalyl chloride in an aprotic solvent at 0° C.), and may then be reacted with the amine VII in situ, preferably in the presence of a tertiary amine. The synthesis of 2-(benzotriazol-1-yl)-N-(benzyloxycarbonyl)glycine (compound VIII) is described by Katritzky et al in *J. Org. Chem.*, 1990, 55, 2206.

Treatment of compounds III with excess phosphoryl chloride (e.g. at 100° C. for about 10 minutes) provides compounds of formula IX:

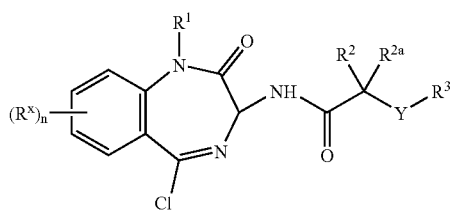

IX wherein $R^x$, n, $R^1$, $R^2$, $R^{2a}$, $R^3$ and Y have the same meanings as before, which are equivalent to compounds of formula II in which $R^4$ is chlorine.

Treatment of the compounds IX with a boronic acid $R^{4b}$—B(OH)$_2$ or diester thereof where $R^{4b}$ represents aryl or heteroaryl, in the presence of a Pd(0) catalyst, provides compounds of formula II in which $R^4$ is aryl or heteroaryl. A preferred Pd(0) catalyst is Pd(PPh$_3$)$_4$ and the reaction is typically carried out in a sealed vessel under nitrogen in the presence of mild base.

Alternatively, the chlorine atom of the compounds IX may be displaced by reaction with cyanide ion, $R^8$OH or $(R^8)_2$NH, providing compounds of formula II in which $R^4$ represents CN, —OR$^8$ or —N(R$^8$)$_2$, where $R^8$ has the same meaning as before. The reactions are typically carried out at elevated temperature, e.g. at 60° C. in a sealed tube.

In a further alternative, the compounds of formula IX may be reacted with $R^4$CONHNH$_2$ to provide compounds of formula X:

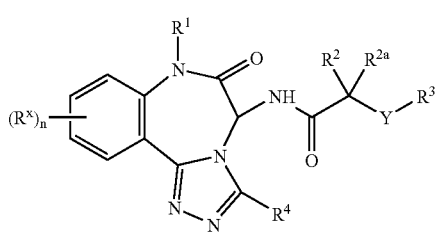

X wherein $R^x$, n, $R^1$, $R^2$, $R^{2a}$, $R^3$, $R^4$ and Y have the same meanings as before. The reaction may be carried out at high temperature (e.g. about 190° C.) in an inert solvent such as Dowtherm™ A.

An alternative synthetic route to the compounds of formula II involves reaction of a carboxylic acid V with a compound of formula XI:

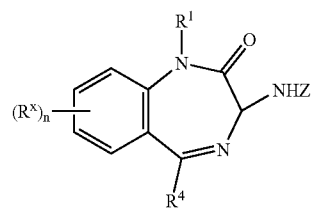

XI

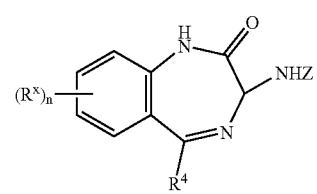

XII where Z, $R^x$, n, $R^1$ and $R^4$ have the same meanings as before. After removal of the protecting group Z by treatment with acid, any of the standard coupling techniques may be used, notably those described in connection with compounds III above. If $R^1$ is other than H, the compounds XI may be prepared by reaction of compounds of formula XII with $R^1$-G, where G represents a leaving group such as tosylate or halide, especially iodide. The reaction may be carried out at ambient temperature in the presence of a strong base such as sodium hydride in an aprotic solvent such as DMF.

The compounds of formula XII in which $R^4$ is other than halogen, CN, —OR$^8$ or —N(R$^8$)$_2$ are available from the reaction of compound VIII with a compound of formula XIII:

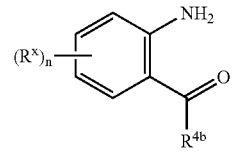

XIII where $R^x$ and n have the same meanings as before and $R^{4b}$ is $R^4$ as defined previously which is other than halogen, CN, —OR$^8$ or —N(R$^8$)$_2$. The process involves conversion of the carboxylic acid VIII to the corresponding acid chloride and coupling with the amine XIII using similar methods as used in the reaction of VII with VIII. Thereafter, treatment with ammonia under the conditions described in *J. Org. Chem.*, 1995, 60, 730–4 affords the compounds XII.

An alternative route to the compounds of formula XI involves introduction of an azide group to a compound of formula XIV, followed by reduction of the azide to the corresponding primary amine and protection of same as the benzyloxycarbonyl derivative:

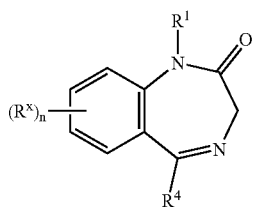

XIV where $R^x$, n, $R^1$ and $R^4$ have the same meanings as before. Introduction of the azide group may be achieved by treatment of XIV with strong base (e.g. potassium hexamethyldisilazide) at low temperature (e.g. −78° C.) under aprotic conditions, followed by reaction with triisopropylbenzenesulfonyl azide. Reduction of the azide group is readily achieved by standard methods, such as hydrogenation over Pd/C, as is protection of the resulting amine by treatment with benzyl chloroformate or with di-t-butyl dicarbonate.

The compounds of formula XIV in which $R^4$ is other than H, halogen, CN, —$OR^8$ or —$N(R^8)_2$ are obtained by reaction of a compound of formula XV with $R^{4b}$MgBr followed by treatment with acid:

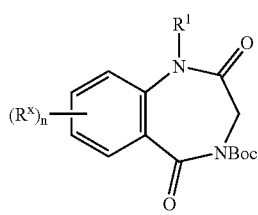

XV where $R^x$, n, $R^1$ and $R^{4b}$ have the same meanings as before and Boc represents t-butoxycarbonyl. The Grignard reagent $R^{4b}$MgBr is prepared from $R^{4b}$Br under standard conditions and is typically reacted with XV at low temperature (e.g. −78° C.) under aprotic conditions. The resulting adduct is treated with acid (e.g. by bubbling with HCl gas in a cooled ethyl acetate solution) to remove the Boc protecting group and enable conversion to XIV. The synthesis of compounds of formula XV is described in WO97/49690.

In an alternative synthetic route to compounds of formula III, an isatoic anhydride derivative XVI is reacted with 2,4,6-trimethoxybenzylamine to provide the amide XVII

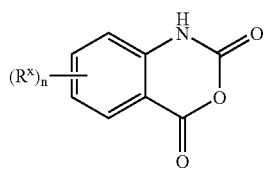

XVI

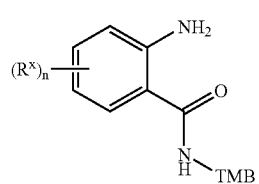

XVII where $R^x$ and n have the same meanings as before, and TMB represents 2,4,6-trimethoxybenzyl. The reaction occurs at moderately elevated temperature, for example by refluxing in ethyl acetate overnight. Reaction of XVII with bromoacetyl bromide provides the corresponding bromoacetamide, which may be cyclised to the benzodiazepinedione XVIII by treatment with alkoxide ion:

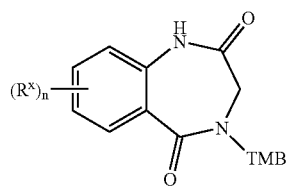

XVIII where $R^x$, n and TMB have the same meanings as before. Preparation of the bromoacetamide may be carried out in a two phase system ($CH_2Cl_2$/10N NaOH) and cyclisation of the crude product may be effected by refluxing in a solution of sodium hydride in isopropanol. If desired, the compounds XVIII may be alkylated in the 1-position by reaction with $R^1$-G in the presence of base, as described above for the conversion of XII to XI, and thereafter are converted to the azides XIX by treatment with triisopropylbenzenesulfonyl azide in the presence of strong base:

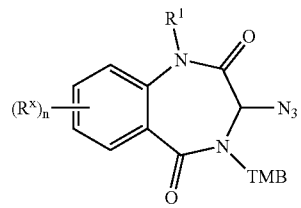

XIX where $R^1$, $R^x$, n and TMB have the same meanings as before. The reaction is conveniently carried out at −78° C. under anhydrous conditions using potassium t-butoxide as base. The azide may be reduced using standard methods (e.g. treatment with triphenylphosphine at ambient temperature in aqueous-organic solution), and the resulting primary amine is coupled with a carboxylic acid V as described above in connection with formation of III from IV. The resulting compounds are in accordance with the invention (formula I, A-B represents —C(O)—$NR^5$—, $R^5$ is trimethoxybenzyl), but if desired, the TMB group may be cleaved by treatment with trifluoroacetic acid and dimethyl sulfide under aqueous conditions to provide the compounds III. Other compounds of this class wherein $R^5$ is other than H or TMB may be prepared by the same route, substituting $R^5NH_2$ for trimethoxybenzylamine in the reaction with XVI.

Compounds of formula I wherein A-B represents —$NR^5$—C(O)— may be prepared by coupling a carboxylic acid V with an amine XX:

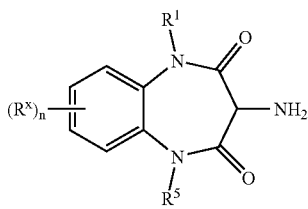

where $R^x$, n, $R^1$ and $R^5$ have the same meanings as before. The amines XX may be prepared by the methods described in WO96/40655, and the coupling reaction with V is carried out as described previously for the coupling of V with IV.

Compounds of formula I in which X represents S may be prepared by treatment with Lawesson's reagent of the corresponding compounds in which X represents O. Alternatively, and advantageously, this reaction may be carried out on the synthetic precursors of such compounds, such as the compounds of formula XI. The reaction may be carried out as described in WO95/14693. The compounds of formula I, or the precursors thereof, wherein X represents N—$R^a$, where $R^a$ has the same meaning as before, may be prepared from the corresponding compounds in which X represents S using the methods disclosed in WO95/14693.

It will be appreciated that a given compound in accordance with formula I may be converted to another compound of formula I by the application of known synthetic techniques (see, for example, the transformations of compounds III and IX outlined above). As a further illustration of this principle, compounds of formula I in which $R^4$ is aryl or heteroaryl may undergo reactions which introduce one or more substituents to the aryl or heteroaryl ring, or which convert substituents already present thereon into different substituents.

Alternatively, it may be more convenient to effect such transformations on the intermediates XI prior to their coupling with V. As an illustration of this protocol, a compound XI in which $R^4$ is 4-(4,4-dimethyl-4,5-dihydrooxazol-3-yl)phenyl may be converted to the corresponding benzoic acid ($R^4$ is 4-carboxyphenyl) and thence to the corresponding benzamide ($R^4$ is 4-carbamoylphenyl). Conversion of the dihydrooxazole to the carboxylic acid may be effected by successive treatments with dilute hydrochloric acid, acetyl chloride and dilute sodium hydroxide, while conversion of the carboxylic acid to the carboxamide may be achieved by any of the well known means, such as reaction with EDC and ammonium chloride. As a further illustration, a compound of formula XI in which $R^4$ is 4-bromophenyl may be converted to the corresponding compound in which $R^4$ is 4-carbamoylphenyl by reaction with carbon monoxide and hexamethyldisilazane in the presence of bis(diphenylphosphino)propane, Pd(II) acetate and a tertiary amine.

Also, compounds XI in which $R^4$ is Cl (or their BOC-protected counterparts) may be prepared as described in Scheme 8 of the Examples, and subjected to the same chemical transformations as the compounds III, prior to coupling with acids V.

Similarly, transformations involving the Y group may be carried out before or after coupling of the acids V with the relevant benzodiazepine derivatives. Examples of such transformations include oxidation of the compounds wherein Y comprises a —CHOH— group to give the corresponding ketones, which in turn may be converted to the oximes by treatment with hydroxylamine. Hydroxyl groups forming part of Y may be converted to ether, ester or silyl ether groups, respectively, by standard methods of alkylation, acylation or silylation. Ketone groups forming part of Y may b reduced to —CHOH— by standard methods, e.g. reaction with sodium borohydride. When Y comprises an alkenyl group (e.g. when Y is —CH(CH=CH₂)—), standard procedures such as hydrogenation and electrophilic addition may be carried out on the olefinic group. A particularly useful process, when Y is —CH(CH=CH₂)—, involves ozonolysis followed by reduction of the resulting aldehyde with borohydride to provide compounds in which Y is —CH(CH₂OH)—. The primary alcohol group may be alkylated or acylated by standard methods, or displaced by bromine by treatment with carbon tetrabromide and triphenylphosphine. The resulting bromomethyl derivative may be reduced to the corresponding methyl derivative by treatment with tributyltin hydride, these processes being described in greater detail in Scheme 5 of the Examples.

The starting materials V, VII, VIII, XIII and XV, where they are not commercially available, may be prepared by standard procedures well known from the art, or by methods analogous to those described in detail hereinafter. For example, the carboxylic acids V, where they are not commercially available, may be prepared by methods similar to those described in *Pure Appl. Chem.*, 1981, 53, 1109, *Org. Synth.* 1990, 68, 83–90; *J. Org. Chem.* 1992, 57, 2768; *Aldrichimica Acta*, 1982, 53, 23; *J. Am. Chem. Soc.* 1991, 113, 4026; and *J. Chem. Soc., Perkin Trans.* 1, 1994, 1141–7.

Carboxylic acids V in which $R^{2a}$ is H and Y represents —CH(CH=CH₂)— may be prepared by rearrangement of allylic esters XXI:

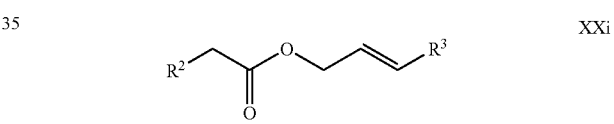

where $R^2$ and $R^3$ have the same meanings as before. The rearrangement can be performed with a high degree of enantioselectivity in the presence of a chiral boron reagent, as described in Scheme 5 of the Examples.

It will be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:
(1) Mouse neuroblastoma neuro 2a cells expressing human app695 are cultured at 50–70% confluency in the presence of sterile 10 mM sodium butyrate.
(2) Cells are placed in 96-well plates at 30,000/well/100 μL in minimal essential medium (MEM) (phenol red-free)+ 10% foetal bovine serum (FBS), 50 mM HEPES buffer (pH7.3), 1% glutamine, 0.2 mg/ml G418 antibiotic, 10 mM sodium butyrate.
(3) Make dilutions of the compound plate. Dilute stock solution to 5.5% DMSO/110μM compound. Mix compounds vigorously and store at 4° C. until use.
(4) Add 10 μL compound/well. Mix plate briefly, and leave for 18 h in 37° C. incubator.
(5) Remove 90 μL of culture supernatant and dilute 1:1 with ice-cold 25 mM HEPES (pH0.3), 0.1% BSA, 1.0 mM EDTA (+ broad spectrum protease inhibitor cocktail; pre-aliquotted into a 96-well plate). Mix and keep on ice or freeze at −80° C.
(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.
(7) Prepare reagents necessary to determine amyloid peptide levels, for example by ELISA assay.
(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 μL/well MTS/PES solution to the cells; mix and leave at 37° C.
(11) Read plate when the absorbance values are approximately 1.0 (mix briefly before reading to disperse the reduced formazan product).

Alternative assays are described in *Biochemistry*, 2000, 39(30), 8698–8704.

The Examples of the present invention all had an $ED_{50}$ of less than 10 μM, in preferred cases less than 1 μM, and in most preferred cases less than 100 nM in at least one of the above assays.

EXAMPLES

The following schemes are representative of the methods used to prepare the compounds of the invention.

Scheme 1

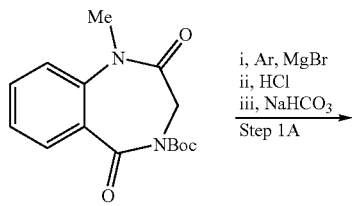

i, Ar, MgBr
ii, HCl
iii, NaHCO₃
Step 1A

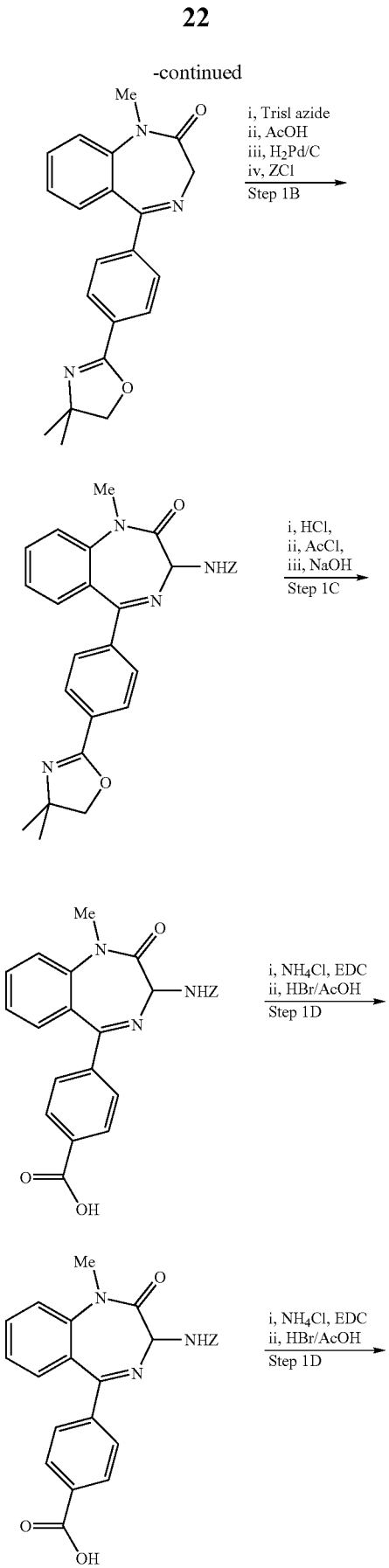

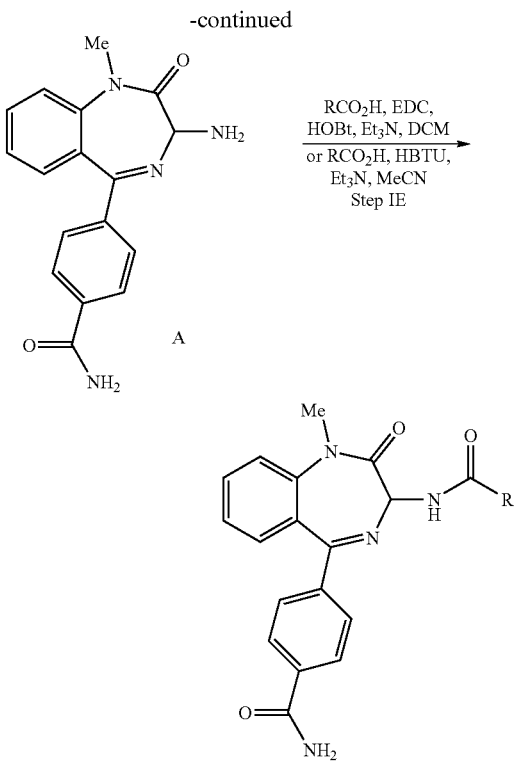

Step 1A.

To a stirred solution of 2-(4bromophenyl)-4,4-dimethyl-4,5-dihydrooxazole (*J. Org. Chem.* 1974, 39, 2790) (9.15 g, 36.0 mmol.) in THF (100 ml) under nitrogen was added magnesium turnings (950 mg, 43.2 mmol.) and several crystals of iodine. The vigorously stirred mixture was gently warmed until the reaction had initiated. The mixture was allowed to self-reflux for 20 minutes and stirred a further 1 hour at room temperature. The resulting deep brown solution was added via cannula to a −78° C. solution of tert-butyl 1-methyl-2,5-dioxo-1,2,3,5-tetrahydro-4H-1,4-benzodiazepine-4-carboxylate (WO 97/49690) (9.50 g, 32.8 mmol.) in THF (100 ml) and stirred at −78° C. for 20 minutes. The cooling bath was removed and the reaction stirred for a further 2 hours after which time a saturated solution of $NH_4Cl$ (100 ml) was added. The mixture was extracted into ethyl acetate (2×150 ml) and the combined organics dried ($MgSO_4$), evaporated and purified by column chromatography ($SiO_2$; Ether) to afford the adduct 12.05 g, (79%) as an off-white solid. ($^1H$, $CDCl_3$) [exists as a ca. 4:1 mixture of rotamers—data for major rotamer only reported] 8.03 (2H, d, J=7 Hz), 7.79 (2H, d, J=8.5 Hz), 7.62 (1H, m), 7.47 (1H, m), 7.36 (1H, d, J=8 Hz), 5.36 (1H, br s), 4.14 (2H, s), 3.81 (1H, dd, J=18, 6 Hz), 3.60 (1H, dd, J=18,4 Hz), 3.08 (3H, s), 1.40 (9H, s) and 1.39 (6H, s). Into a stirred solution of the Boc-protected amine (12.0 g, 26 mmol.) in ethyl acetate (600 ml) cooled to −5° C. was bubbled HCl gas for 2.5 hours. After this time the solvent was evaporated to give a solid which was redissolved in a mixture of THF (200 ml) and saturated aqueous $NaHCO_3$ (300 ml). The mixture was vigorously stirred for 1 hour and extracted into ethyl acetate (2×300 ml). Drying ($MgSO_4$) and evaporation afforded the product as a solid (8.9 g, 99%). ($^1H$, $CDCl_3$) 7.96 (2H, d, J=8 Hz), 7.65 (2H, d, J=8 Hz), 7.56 (1H, t, J=8 Hz), 7.36 (1H, d, J=8 Hz), 7.25 (1H, d, J=8 Hz), 7.18 (1H, t, J=8 Hz), 4.83 (1H, d, J=10.5 Hz), 4.13 (2H, s), 3.79 (1H, d, J=10.5 Hz), 3.43 (3H, s) and 1.40 (6H, s).

Step 1B.

To a stirred solution of the benzodiazepinone from Step 1A(10.6 g, 30 mmol.) in THF (300 ml) at −78° C. was added potassium hexamethyldisilazide (0.5M solution in toluene, 86 ml, 43 mmol.) portionwise over 15 minutes and the mixture stirred for 10 minutes at −78° C. After this time, 2,4,6-triisopropylbenzenesulfonyl azide (10.86 g, 35 mmol.) as a solution in THF (75 ml) was added via cannula and the reaction stirred a further 10 minutes. A mixture of glacial acetic acid (4 ml) and THF (75 ml) was then added, the cooling bath removed and the mixture stirred for 90 minutes. Saturated $NaHCO_3$ solution (200 ml) was added and the mixture extracted into ethyl acetate (3×150 ml). The combined organics were dried ($MgSO_4$) and evaporated to give a solid which was triturated with ether to afford the desired azide as a colourless solid (9.1 g, 77%). ($^1H$, $CDCl_3$) 7.99 (2H, d, J=8.5 Hz), 7.72 (2H, d, J=8.5 Hz), 7.62 (1H, t, J=8 Hz), 7.40 (1H, d, J=8 Hz), 7.32 (1H, d, J=8 Hz), 7.25 (1H, t, J=8 Hz), 4.56 (1H, s), 4.14 (2H, s), 3.49 (3H, s) and 1.40 (6H, s). A solution of the azide (5.95 g, 15 mmol.) in ethanol (150 ml) was degassed with nitrogen bubbling for 10 minutes and then 5% palladium on charcoal (100 mg) added and the mixture hydrogenated at 35 psi $H_2$ for 1 hour. The mixture was filtered through a pad of Celite washing well with ethanol and the combined organics evaporated to afford the amine (5.5 g, 99%). ($^1H$, $CDCl_3$) 7.96 (2H, d, J=8 Hz), 7.66 (2H, d, J=8 Hz), 7.58 (1H, t, J=8 Hz), 7.37 (1H, d, J=8 Hz), 7.27 (1H, d, J=8 Hz), 7.20 (1H, t, J=8 Hz), 4.49 (1H, s), 4.13 (2H, s), 3.48 (3H, s) and 1.40 (6H, s). To a stirred solution of the amine (5.6 g, 15.4 mmol.) and sodium carbonate (1.97 g, 18.6 mmol.) in a mixture of dioxan (200 ml) and water (100 ml) at 0° C. was added benzyl chloroformate (2.4 ml, 16.8 mmol.) dropwise. The mixture was stirred for 75 minutes at 0° C., quenched with saturated ammonium chloride solution (200 ml) and extracted into ethyl acetate (2×200 ml). The combined organics were dried ($MgSO_4$) and evaporated to afford the product as a foam (7.7 g, 99%). ($^1H$, $CDCl_3$) 7.95 (2H, d, J=8 Hz), 7.65–7.59 (3H, m), 7.39–7.23 (8H, m), 6.72 (1H, d, J=8 Hz), 5.32 (1H, d, J=8 Hz), 5.15 (2H, ABq), 4.14 (2H, s), 3.48 (3H, s) and 1.40 (6H, s).

Step 1C.

The oxazoline from Step 1B (7.7 g, 15.5 mmol.) was dissolved in a mixture of dioxan (50 ml) and 1M HCl (150 ml) and stirred at ambient temperature for 24 hours. After this time, the mixture was cautiously basified with sodium carbonate solution and extracted into ethyl acetate (3×150 ml) and dichloromethane (2×100 ml). The combined organic extracts were dried ($MgSO_4$), evaporated and then redissolved in dichloromethane (100 ml). The solution was cooled to 0° C., triethylamine (1.4 ml, 10 mmol.) and acetyl chloride (0.66 ml, 9.2 mmol.) added and the mixture stirred at ambient temperature for 1 hour. The solvent was evaporated and the residue taken up in a mixture of THF (100 ml) and 1N NaOH (30 ml) and the mixture stirred for a further 18 hours. After this time, the solution was washed with ether (100 ml) and the aqueous layer acidified to pH 2 with 1N HCl and extracted into ethyl acetate (3×100 ml). The combined ethyl acetate layers were dried ($MgSO_4$) and evaporated to afford the product as an oil (3.5 g, 51%). ($^1H$, $CDCl_3$) 8.09 (2H, d, J=8.5 Hz), 7.75–7.59 (4H, m), 7.41–7.24 (7H, m), 6.74 (1H, d, J=8 Hz), 5.34 (1H, d, J=8 Hz), 5.15 (2H, ABq) and 3.48 (3H, s).

Step 1D.

To a stirred solution of the carboxylic acid from Step 1C (4.25 g, 9.6 mmol.) in DMF (75 ml) was added ammonium chloride (5.0 g, 95 mmol.), EDC (2.21 g, 11.5 mmol.), HOBt (1.56 g, 11.5 mmol.) and triethylamine (20 ml) and the mixture stirred at ambient temperature for 18 hours. The solvent was evaporated and the residue taken up in ethyl acetate (100 ml), washed with 1N HCl (100 ml), saturated NaHCO$_3$ solution (100 ml) and water (3×100 ml). The organic layer was dried (MgSO$_4$) and evaporated to give a yellow powder which was triturated with ether to afford an off-white powder (2.7 g, 64%). ($^1$H, CDCl$_3$) 7.82 (2H, d, J=8.5 Hz), 7.75–7.59 (4H, m), 7.41–7.23 (7H, m), 6.72 (1H, d, J=8 Hz), 6.1 (1H, br s), 5.65 (1H, br s), 5.33 (1H, d, J=8 Hz), 5.15 (2H, ABq) and 3.48 (3H, s). To this benzyl carbamate (1.45 g, 3.3 mmol.) was added HBr (45% in acetic acid, 9 ml) and the mixture stirred at ambient temperature until all the starting material had dissolved (35 minutes). The resulting bright orange solution was poured into ice cold ether (150 ml) and vigorously stirred for 10 minutes at 0° C. and filtered. The resulting pale yellow solid was partitioned between 4N NaOH (75 ml) and dichloromethane (100 ml), the layers separated and the aqueous layer extracted with further dichloromethane (3×100 ml) and 10% v/v methanol/dichloromethane (2×100 ml). The combined organic layers were dried (MgSO$_4$) and evaporated to give a yellow semi-solid which was triturated with ether to afford the product as an off-white powder (850 mg, 84%).

($^1$H, CDCl$_3$) 7.83 (2H, d, J=8 Hz), 7.72 (2H, d, J=8 Hz), 7.60 (1H, t, J=8 Hz), 7.38 (1H, d, J=8 Hz), 7.28 (1H, d, J=8 Hz), 7.22 (1H, t, J=8 Hz), 6.72 (1H, d, J=8 Hz), 6.15 (1H, br s), 5.65 (1H, br s), 4.49 (1H, s) and 3.48 (3H, s).

Step 1E Representative Procedures.

i, To a stirred solution of the amine from Step 1D (0.3 mmol.) in dichloromethane or DMF (5 ml) under nitrogen was added the carboxylic acid (0.33 mmol.), EDC (0.33 mmol.), HOBt (0.33 mmol.) and triethylamine (0.6 mmol.) and the mixture stirred at ambient temperature for 12–24 h. The mixture was diluted with further dichloromethane (25 ml), washed successively with 1N HCl (25 ml) [this washing omitted for products bearing basic centres], 1N NaOH (25 ml) and brine, dried (MgSO$_4$) and evaporated. The residue was purified by HPLC, column chromatography or preparative thin layer chromatography on silica using an appropriate eluent.

ii, To a stirred solution of the amine from Step 1D (0.3 mmol.) in acetonitrile (5 ml) under nitrogen was added the carboxylic acid (0.33 mmol.), HBTU (0.33 mmol.) and triethylamine (0.6 mmol.) and the mixture stirred at ambient temperature for 12–24 h. Water (1 ml) was added, the mixture was lyophilized and the residue purified by HPLC using an appropriate eluent.

The product from Step 1D (designated A) could alternatively be prepared by the route shown in Scheme 2.

Scheme 2

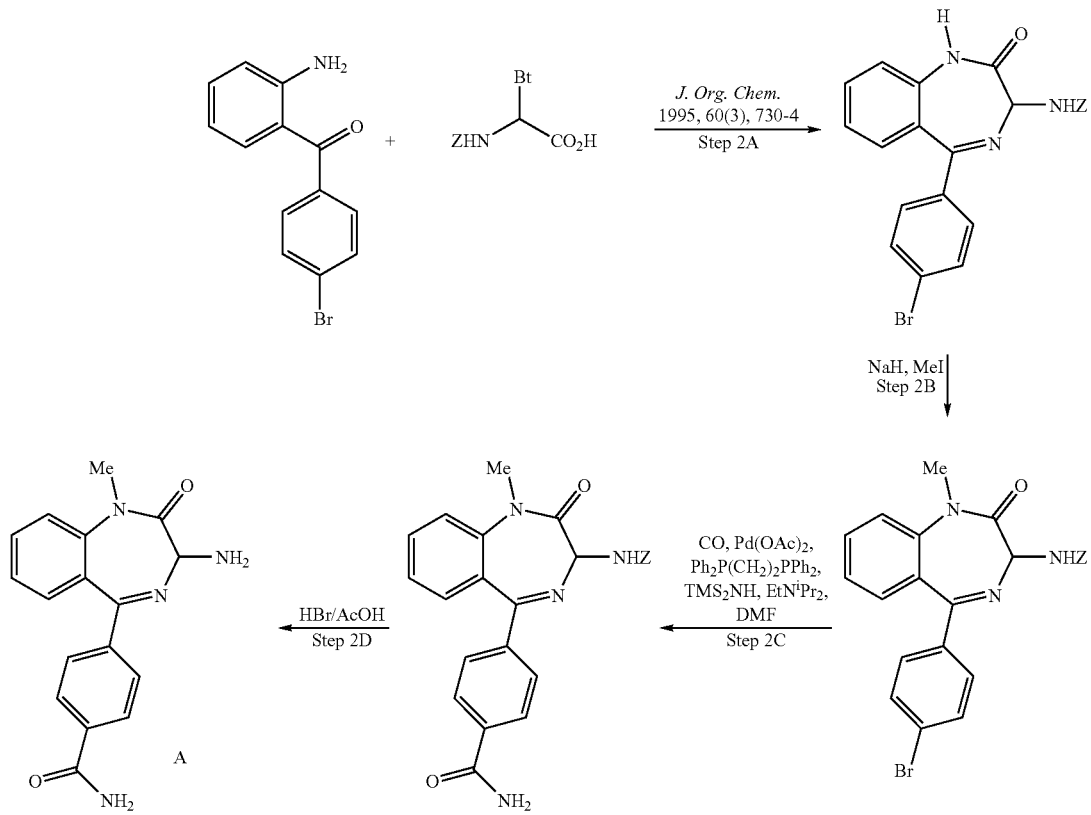

Step 2A.

[5-(4bromophenyl)-2-oxo-2,3-dihydro-1H-benzo[e][1,4]-diazepin-3-yl]-carbamic acid benzyl ester.

2-Amino-4'-bromobenzophenone (*J. Chem. Soc, Perkin Trans.* 1, 1995, 203–212) and the 2-(benzotriazol-1-yl)-N-(benzyloxycarbonyl)glycine (A. R. Katritzky et al, *J. Org. Chem.*, 1990, 55, 2206) were reacted in an analagous fashion to that described in *J. Org. Chem.* 1995, 60, 730–4 to give the title compound. $^1$H NMR (DMSO) 5.02–5.07 (3H, m), 7.25–7.67 (14H, m), 8.45 (1H, d).

Step 2B.

[5-(4-bromophenyl)-1-methyl-2-oxo-2,3-dihydro-1H-benzo[e][1,4]-diazepin-3-yl]-carbamic acid benzyl ester.

The product from Step 2A (8 g, 0.0172 moles) was dissolved in DMF (120 ml) and treated with a 60% dispersion of sodium hydride in mineral oil (760 mg, 0.019 moles) followed by iodomethane (2.94 g, 0.021 moles) and allowed to stir at ambient temperature for 16 hours. The reaction was quenched with water (100 ml) and extracted into ethyl acetate (2×100 ml). The combined organic layers were washed with water (100 ml) and brine (100 ml), dried (MgSO$_4$) and evaporated in vacuo. Purification by chromatography (SiO$_2$, 1% diethylether/dichloromethane) followed by trituration with ether afforded the title compound (3.5 g, 43%). $^1$H NMR (DMSO) 3.38 (3H, s), 5.06 (2H, s), 5.09 (1H, d, J=8.5 Hz), 7.34–7.68 (13H, m), 8.50 (1H, d).

Step 2C.

[5-(4-carbamoyl-phenyl)-1-methyl-2-oxo-2,3-dihydro-1H-benzo[e][1,4]-diazepin-3-yl-]carbamic acid benzyl ester.

A solution of the product from Step 2B (3.5 g, 0.0073 moles), 1,3-bis(diphenylphosphino)propane (305 mg, 0.0073 moles), hexamethyldisilazane (10.8 ml, 0.0146 moles), and N,N-diisopropylethylamine (2.5 ml, 0.0146) in DMF were degassed with nitrogen bubbling for ten minutes. Palladium (II) acetate (162 mg, 0.00073 moles) was added and the mixture degassed for a further five minutes. Carbon monoxide gas was bubbled through the reaction mixture for 5 minutes at room temperature and then for 6 hours at 110° C. After this time, the reaction mixture was cooled and partitioned between dichloromethane (50 ml) and water (50 ml). The aqueous layer was extracted with further dichloromethane (3×50 ml) and the combined organic layers washed with water (100 ml) and brine (100 ml), dried (MgSO$_4$) and vaporated in vacuo. The residue was taken up in a mixture of THF (150 ml) and 2M HCl (30 ml) and stirred at ambient temperature for one hour. The THF was then evaporated in vacuo and the residue partitioned between dichloromethane (50 ml) and 2M NaOH (50 ml). The aqueous layer was extracted with dichloromethane (2×50 ml) and the combined organic layers washed (H$_2$O, brine), dried (MgSO$_4$) and evaporated in vacuo. Purification by chromatography (SiO$_2$, 1% MeOH/CHCl$_3$) gave the title compound. $^1$H NMR (DMSO-d$^6$) 3.31 (3H, s), 5.07 (2H, s), 5.12 (1H, d), 7.30–7.80 (12H, m), 7.93 (2H, d, J=8.4 Hz), 8.08 (1H, br s), 8.50 (1H, d). MS (ES+) MH$^+$=443

Step 2D.

4(3-amino-1-methyl-2-oxo-2,3-dihydro-1H-benzo[e][1,4]diazepin-5-yl)-benzamide.

To the product from Step 2C (400 mg, 0.9 mmol.) was added hydrogen bromide (45 wt % in acetic acid, 2 ml) and the mixture stirred until dissolution was complete (30 minutes). After this time, the orange solution was poured into ice cold ether (20 ml) and vigorously stirred for 10 minutes. The resulting precipitate was filtered and washed with cold ether to give the title compound (220 mg, 80%) as the hydrobromide salt.

$^1$H NMR (CDCl$_3$) 3.08 (3H, s), 4.50 (1H, s), 5.70 (1H, v br s), 6.15 (1H, v br s), 7.20–7.42 (5H, m), 7.57–7.85 (5H, m). MS (ES+) MH$^+$=309.

Scheme 3

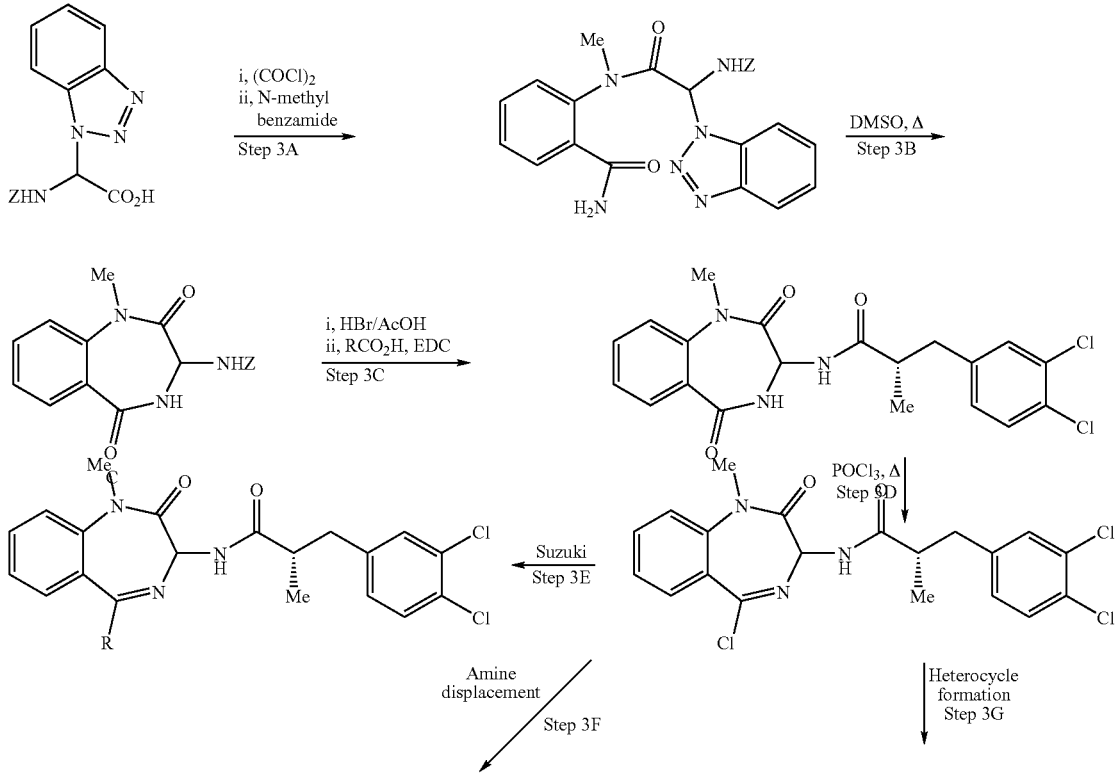

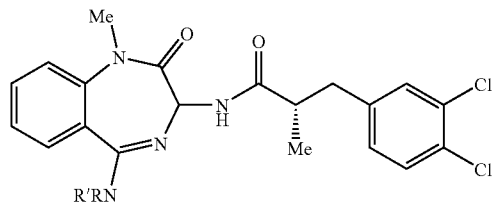
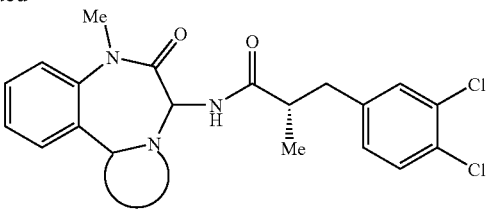

Step 3A.

Benzotriazol-2yl-[(2-carbamoyl-phenyl)-methyl-carbamoyl]-methyl}-carbamic acid benzyl ester A solution of 2(benzotriazol-1-yl)-N-(benzyloxycarbonyl)glycine (A. R. Katritzky et al, *J. Org. Chem.*, 1990, 55, 2206) (50 g, 0.15 mol) in THF (300 ml) at 0° C. was treated slowly with oxalyl chloride (2.0 M in $CH_2Cl_2$, 81 ml, 0.16 mol) and DMF (1 ml). The reaction mixture was stirred at 0° C. for 2 h, then treated with a solution of 2-(methylamino)benzamide (23 g, 0.15 mol) and 4-methylmorpholine (38 ml, 0.35 mol) in THF (100 ml). The reaction mixture was stirred overnight at 40° C., then filtered. The residue was partitioned between water and warm ethyl acetate. The aqueous layer was extracted three times with ethyl acetate and the combined extracts combined with the original filtrate, dried (MgSO4), filtered and evaporated in vacuo. Trituration with ethyl acetate gave the product as a white powder (23 g, 33%). The mother liquors were evaporated and purified by column chromatography to give a further quantity of the product (21 g, 30%). ($^1$H NMR, DMSO-d$^6$) 9.3 (1H, d), 8.8 (1H, d), 8.15–6.90 (15H, m), 4.92–4.75 (2H, m), 3.12 (3H, d, J=4.2 Hz).

Step 3B.

(1-Methyl-2,5-dioxo-2,3,4,5-tetrahydro-1H-benzo[e][1,4]diazepin-3-yl)-carbamic acid benzyl ester The product from Step 3A (23 g, 0.05 mol) was added to DMSO (500 ml) at 180° C. The reaction mixture was stirred at 180° C. for 20 min, cooled and diluted with 1 M NaOH (aq) and ether. The aqueous phase was extracted with ethyl acetate (five times) and the combined organic phases were washed with brine, dried, filtered and evaporated. Purification by column chromatography gave the product (5.8 g, 34%) as a yellow solid.

($^1$H NMR, DMSO-d$^6$) 9.30 (1H, d, J=4.0 Hz), 9.0 (3H, br s), 7.75–7.68 (2H, m), 7.56 (1H, d, J=8.1 Hz), 7.45–7.41 (1H, m), 5.20 (1H, d, J=4.2 Hz), 3.4 (3H, s).

Step 3C.

3-(3,4-Dichloro-phenyl)-2R-methyl-N-(1-methyl-2,5-dioxo-2,3,4,5-tetrahydro-1H-benzo[e][1,4]diazepin-3-yl)-propionamide.

The product from Step 3B (3.27 g, 9.64 mmol) was dissolved in 48% HBr-AcOH, stirred for 35 min. and poured into a large volume of ice-cold ether. The resulting precipitate was collected by filtration, washed with ether and dried in vacuo. The product was obtained as a white solid (2.65 g, 96%). ($^1$H NMR, DMSO) 8.73 (1H, br d, J=3.6 Hz), 7.74–7.32 (10H, m), 5.21 (1H, dd, J=4.6, 7.8 Hz), 5.06 (2H, s), 3.31 (3H, s). MH+=340, MNa+=352. This product was coupled to (2R)-2-methyl-3-(3,4-dichlorophenyl)propionic acid under standard conditions (c.f Step 1E) to yield the desired product. $^1$H NMR (CDCl$_3$) δ 1.18 (1.5H, d, J=6.6 Hz), 1.24 (1.5H, d, J=6.6 Hz), 2.58–2.67 (2H, m), 2.86–2.97 (1H, m), 3.44 (3H, s), 5.42–5.53 (1H, m), 5.82 (0.5H, br s), 6.18 (0.5H, br s), 6.90–7.04 (3H, m), 7.18–7.40 (4H, m), 7.57–7.61 (1H, m), 7.90–7.93 (1H, m).

Step 3D.

N-(5-Chloro-1-methyl-2-oxo-2,3dihydro-1H-benzo[e][1,4]diazepin-3-yl)-3-(2,4-dichloro-phenyl)-2R-methyl-propionamide.

A solution of the product from step 3C (1.0 g, 2.38 mmol) in POCl$_3$ (15 ml) was heated at 100° C. for 10 min. The reaction mixture was cooled, diluted with ethyl acetate and poured into ice-cold NaHCO$_3$ solution. The organic phase was washed with brine (twice), dried, filtered and evaporated in vacuo. The resulting material was combined with similar material obtained by performing the foregoing procedure on further product from step 3C (1.5 g, 3.57 mmol), and the whole was purified by column chromatography to give the imidoyl chloride product (2.03 g, 79%) as a pale yellow foam. $^1$H NMR, (1:1 mixture of diastereomers, CDCl$_3$) δ 1.18–1.28 (3H, m), 2.58–2.67 (2H, m), 2.93–3.04 (1H, m), 3.44 (1.5H, s), 3.47 (1.5H, s), 5.34 (0.5H, d, J=8.1 Hz), 5.41 (0.5H, d, J=8.3 Hz), 7.00–7.38 (6H, m), 7.60–7.65 (1H, m), 7.83–7.87 (1H, m).

Step 3E Representative Procedure.

The product from step 3D (100 mg, 0.23 mmoles), tripotassium phosphate (84 mg, 0.4 mmoles), 4-pyridyl boronic acid (43 mg, 0.35 mmoles) and DMF (4 ml) in a thick-walled flask were degassed with nitrogen. Pd(PPh$_3$)$_4$ was added and the vessel sealed and heated at 90° C. for 2 hours. The mixture was cooled and taken up in water/ethyl acetate. The organic layer was washed (water, brine), dried (MgSO$_4$) and evaporated in vacuo. Purification by flash silica column eluting with ethyl acetate gave the title compound as a 1:1 mixture of diastereomers.

Step 3F. Representative Procedure.

3-(3,4-Dichlorophenyl)-2-methyl-N-(1-methyl-2-oxo-5-pyrrolidin-1-yl-2,3-dihydro-1H-benzo[e][1,4]diazepin-3-yl)-propionamide.

The product from step 3D (100 mg, 0.22 mmol.) and pyrrolidine (2 ml) were heated together in a sealed tube at 60° C. for 30 mins. Evaporation in vacuo and purification by chromatography (SiO$_2$, Ethyl acetate) afforded the product.

Step 3G Representative Procedure.

3-(3,4Dichlorophenyl)-2-methyl-N-(6,7-dihydro-7-methyl-6-oxo-5H-1,2,4-triazolo[4,3d][1,4]benzodiazepin-5-yl)-propionamide.

A suspension of the product from Step 3D (50 mg) and formic acid hydrazide (50 mg) in Dowtherm A (2 ml) was heated at 190° C. for 1 h. The reaction mixture was cooled and purified directly by flash column chromatography to yield the title compound (32 mg, 63%) as a mixture of diastereomers.

Scheme 4

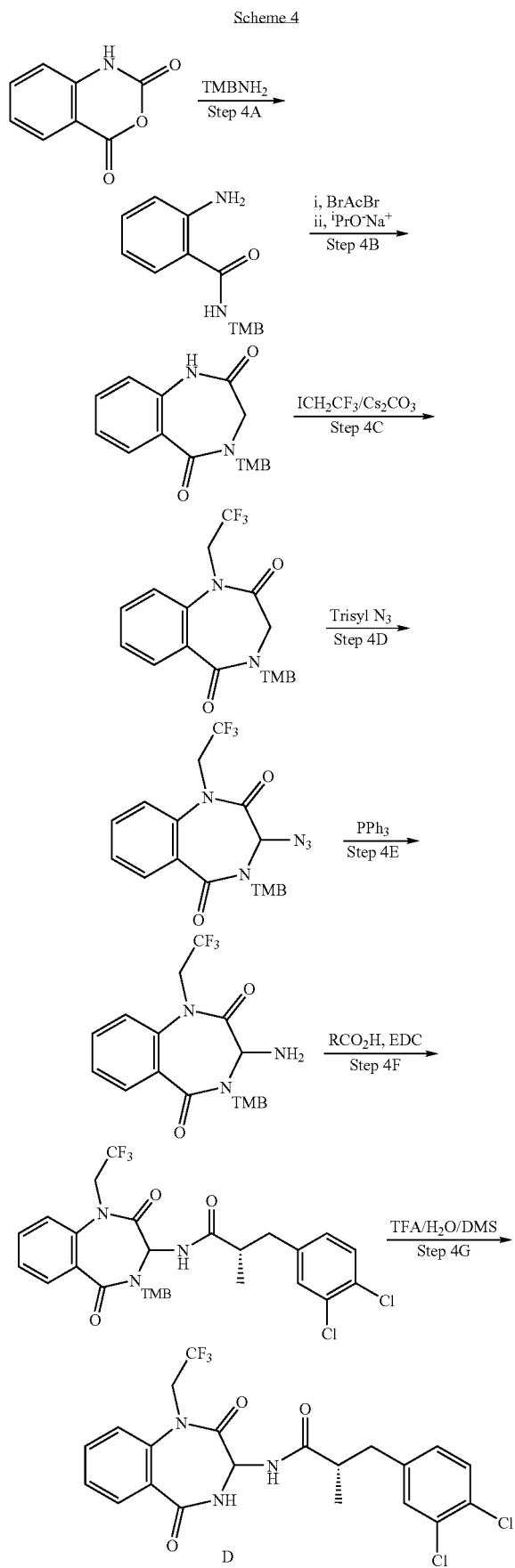

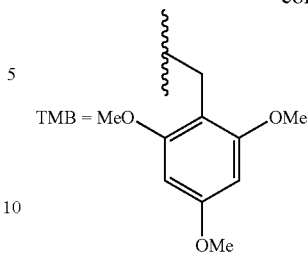

Step 4A.

2-amino-N-(2,4,6-trimethoxybenzyl)benzamide.

Isatoic anhydride (4.6 g, 0.028 mol), 2,4,6-trimethoxybenzyl hydrochloride (6 g, 0.026 mol) and triethylamine (2.6 g, 0.026 mol) in ethyl acetate (50 ml) w re heated to 85° C. for 16 hr. The reaction mite was washed (water, brine), dried (MgSO$_4$) and evaporated in vacuo, then triturated with diethyl ether and dried to give the product as a solid (6.8 g, 77%). ($^1$H NMR DMSO) δ 3.75–3.78 (9H, m), 4.31–4.32 (2H, m), 6.23 (1H, s), 6.30 (2H, bs), 6.45 (1H, m), 6.65 (1H, d, J=8.1Hz), 7.08 (1H, m), 7.39 (1H, m), 7.68 (1H, m).

Step 4B.

4-(2,4,6-trimethoxybenzyl)-3,4-dihydro-1H-1,4benzodiazepine-2,5-dione.

The product from Step 4A (16.2 g, 0.051 mol) was dissolved in dichloromethane (200 ml) and cooled to 0° C. under nitrogen. Bromoacetyl bromide (11.3 g, 0.0562 mol) was added dropwise followed by 10M NaOH (7.7 ml, 0.077 mol). The reaction was allowed to attain room temperature and left for 30 minutes, then diluted (water/dichloromethane). The organic layer was washed (water, brine), dried (MgSO$_4$) and evaporated in vacuo, then triturated with diethyl ether to give the desired condensation product. This was added to a solution of sodium hydride (60% dispersion in mineral oil) (6.1 g, 0.153 mol) in isopropanol (200 ml), and refluxed for 30 minutes. Following evaporation in vacuo, the residue was taken up in water/ethyl acetate. The organic layer was then washed (brine), dried (MgSO$_4$), evaporated in vacuo, and triturated (ethyl acetate/diethyl ether), to give the product as a solid (8 g, 44%). ($^1$H NMR DMSO-d$^6$) 3.54 (2H, s), 3.74 (6H, s), 3.79 (3H, s), 4.65 (2H, s), 6.23 (2H, s), 7.03 (1H, d, J=8.1 Hz) 7.19 (1H, m), 7.45 (1H, m), 7.77 (1H, d, J=8.1 Hz), 10.23 (1H, s).

Step 4C.

1-(2,2,2-trifluoroethyl)4-(2,4,6-trimethoxybenzyl)-3,4-dihydro-1H-1,4benzodiazepine-2,5-dione.

The product from Step 4B (6 g, 0.017 mol) was dissolved in DMF (40 ml) at room temperature under nitrogen. Caesium carbonate (8.2 g, 0.025 mol) was added followed by trifluoroethyl iodide (8.8 g, 0.025 mol) and the mixture stirred at 55° C. for 16 hr. The reaction mixture was taken up in ethyl acetate/water, the organic layer washed (water, brine), dried (MgSO$_4$) and evaporated in vacuo. Purification by chromatography (SiO$_2$, ethyl acetate/dichloromethane) afforded the product as a white solid (2.6 g, 35%). ($^1$H NMR, CDCl$_3$) δ 3.68–3.83 (11H, m), 4.13–4.17 (1H, m), 4.72 (1H, S d, J=13.6 Hz), 4.84–4.88 (1H, m) 5.04 (1H, d, J=13.6Hz), 6.13 (2H, s), 7.18 (1H, d, J=8.3 Hz), 7.32–7.50 (2H, m), 7.96 (1H, m).

Step 4D.

3-azido-1-(2,2,2-trifluoroethyl)-4-(2,4,6-trimethoxybenzyl)-3,4-dihydro-1H-1,4-benzodiazepine-2,5dione.

The product from Step 4C (1 g, 0.0023 mol) was dissolved in THF (30 ml) under nitrogen, cooled to −78° C. and potassium tert butoxide (0.28 g, 0.0025 mol) as a solution in THF (5 ml) added over 10 minutes. 2,4,6-Triisopropylbenzenesulfonyl azide (1.65 g, 0.005 mol) in THF (5 ml) was added dropwise and the mixture stirred for 10 minutes. Glacial acetic acid (0.6 ml) was added and the reaction mixture allowed to attain room temperature and left to stir for 4 hours. The reaction mixture was poured into sodium hydrogen carbonate solution and extracted (ethyl acetate ×2). The combined organic layers were washed (brine), dried ($MgSO_4$) and evaporated in vacuo to give the desired azide which was used without further purification.

Step 4E.

3-amino-1-(2,2,2-trifluoroethyl)-4-(2,4,6-trimethoxybenzyl)-3,4-dihydro-1H-1,4-benzodiazepine-2,5-dione.

The product from 4D was dissolved in THF (15 ml) and triphenylphosphine (1.2 g, 0.0046 mol) and water (2 ml) were added. The reaction mixture was allowed to stir at room temperature overnight and then evaporated in vacuo. The residue was taken up in 1N HCl and washed twice with ether The aqueous layer was basified with 1N NaOH, extracted with ethyl acetate (×2) and dichloromethane (×2) and the combined organic layers washed with brine, dried ($MgSO_4$) and evaporated in vacuo. Trituration with diethyl ether gave the product as a solid (0.35 g, 35%).

Step 4F and 4G.

(2S)-3-(3,4-dichlorophenyl)-N-[2,5-dioxo-1-(2,2,2-trifluoroethyl)-2,3,4,5-tetrahydro-1H-1,4-benzodiazene-3-yl]-2-methylpropanamide.

The product from Step 4E (0.35 g, 0.00077 mol) was reacted in an analogous fashion to that described in Step 1E using (2S)-3-(3,4-dichlorophenyl)-2-methyl-propionic acid. The crude product from this reaction was treated with a 95/5/5 v/w mixture of trifluoroacetic acid/water/dimethyl sulfide (8 ml) for 5 hours at room temperature under nitrogen. Evaporation in vacuo and purification by chromatography ($SiO_2$, ethyl acetate/dichloromethane) afforded the product (0.175 g, 50%). ($^1$H NMR, DMSO-d$^6$) [1:1 mixture of diastereomers] δ 8.80 (0.5H, d, J=4.8), 8.85 (0.5H, d, J=4.7), 8.73 (0.5H, d, J=7.9), 8.60 (0.5H, d, J=7.8), 7.73–7.44 (5H, m), 7.32–7.14 (2H, m), 5.44 (0.5H, dd, J=4.8, 7.9), 5.38 (0.5H, dd, J=4.7, 7.8), 5.16–5.09 (1H, m), 4.74–4.68 (1H, m), 3.04–2.74 (3H, m), 1.00 (1.5H, d, J=6.8), 0.86 (1.5H, d, J=6.8). m/z: Found 488 (MH$^+$), $C_{21}H_{18}N_3O_3Cl_2F_3$+H$^+$ requires 488.

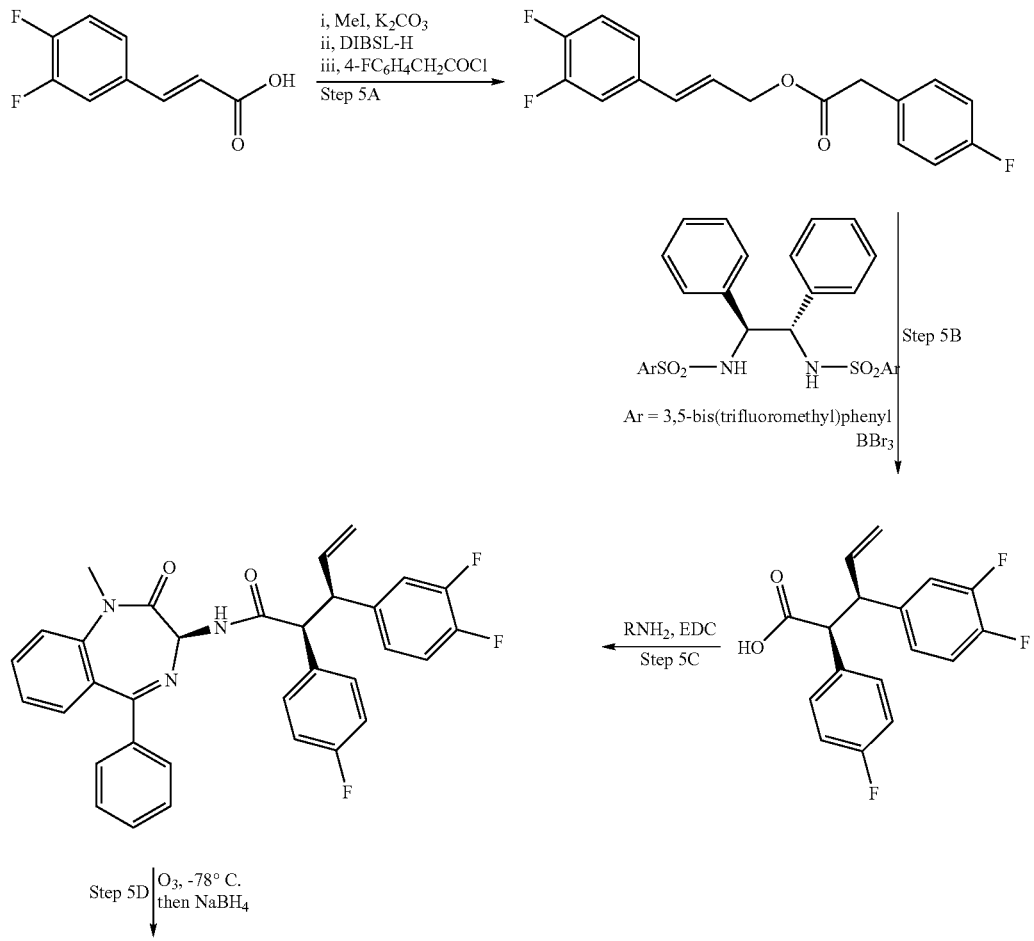

Scheme 5

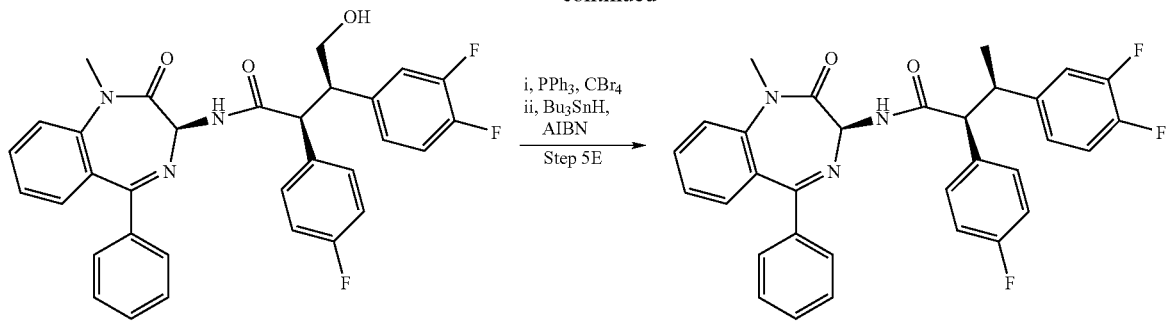

Step 5A

To a stirred solution of 3,4-difluorocinnamic acid (20.0 g, 109 mmol.) in DMF (80 ml) was added potassium carbonate (16.5 g, 120 mmol.) and methyl iodide (7.45 ml, 210 mmol.) and the resulting suspension stirred at room temperature for 2 hours. Water (100 ml) was added and the mixture extracted into ether (2×200 ml). The combined ether layers were washed with 1N NaOH (100 ml) and satd. brine (100 ml) then dried (MgSO$_4$) and evaporated to afford the crude methyl ester (13.7 g) as a colourless powder.

$^1$H NMR (CDCl$_3$) 7.59 (1H, d, J=16.0 Hz), 7.33 (1H, m), 7.21 (1H, m), 7.19 (1H, m), 6.35 (1H, d, J=16.0 Hz) and 3.81 (3H, s).

A one litre flask was charged with the crude methyl ester (15.2 g, 77 mmol.) and anhydrous THF (100 ml) was added under nitrogen. The mixture was cooled to −10° C. and a solution of DIBAL-H (1M in toluene, 180 ml, 180 mmol.) added portionwise over one hour. At the end of the addition the reaction was stirred a further one hour at −10° C. then cooled to −78° C. Methanol (50 ml) was cautiously added dropwise over 10 minutes then the cooling bath removed and a satd. solution of NH$_4$Cl (100 ml) added dropwise over 10 minutes. As the internal temperature of the mixture approached 0° C., a vigorous exotherm initiated which began to boil the solvent and form a thick gel. Once the exotherm had subsided, the mixture was diluted with toluene (100 ml) and stirred vigorously for one hour after which time the gel had become granular in nature. The mixture was filtered through a pad of Celite® and the pad washed well with ether then ether:methanol (1:1 v/v). The combined filtrates were combined, dried (MgSO$_4$) and evaporated to afford the alcohol (12.8 g). $^1$H NMR (CDCl$_3$) 7.22–7.04 (3H, m), 6.54 (1H, d, J=17.7 Hz), 6.29 (1H, dt, J=17.7, 6.1 Hz) and 4.32 (2H, d, J=6.1 Hz).

To a solution of 4-fluorophenylacetic acid (12.2 g, 79 mmol.) in dry DCM (200 ml) at 0° C. was added oxalyl chloride (7.8 ml, 89 mmol.) and DMF (0.3 ml) and the resulting effervescing mixture stirred at 0° C. for 30 minutes then at ambient temperature for a further 45 minutes. The effervescence had ceased after this time and the solvent was evaporated. To the residue was added toluene (50 ml) and the solvent evaporated. The addition of toluene and evaporation was repeated to leave a residue of 4-fluorophenylacetyl chloride.

This acid chloride was dissolved in DCM (100 ml) and added via cannula to a pre-cooled (0° C.) solution of 3-(3,4difluorophenyl)-prop-2-enol (prepared above, 12.8 g, 75 mmol.) and triethylamine (14 ml, 100 mmol.) in DCM (300 ml). The reaction was stirred for 30 minutes at 0° C. then 2 hours at ambient temperature. After this time the mixture was washed with 1N HCl (200 ml), 1N NaOH (200 ml) and brine (200 ml), dried (MgSO$_4$) and evaporated to leave a residue which was purified by flash chromatography (SiO$_2$; ether:DCM:hexane; 1:1:6 v/v/v). Recrystallization from hexane afforded the desired ester (15.0 g, 45% over 3 steps). $^1$H NMR (CDCl$_3$) 7.28–7.25 (2H, m), 7.20–7.14 (1H, m), 7.12–6.99 (4H, m), 6.48 (1H, d, J=16.0 Hz), 6.17 (1H, dt, J=16.0, 6.2 Hz), 4.73 (2H, d, J=6.2 Hz) and 3.64 (2H, s).

Step 5B

To a stirred solution of (S,S)-1,2-bis[[3,5-bis(trifluoromethyl)phenyl] sulfonylamino]-1,2diphenylethane (15.6 g, 20.4 mmol.) in dry DCM (700 ml) under nitrogen was added boron tribromide (41 ml of a 1M solution in DCM, 41 mmol.) and the resulting pale brown solution stirred at ambient temperature for 21 hours. The solvent was removed in vacuo scrupulously avoiding contact of the residual brown powder with the air. To this powder was added further dry DCM (700 ml) under nitrogen and the solvent evaporated again, the flask being filled with nitrogen. Dry toluene (600 ml) was added via cannula and the flask heated gently in an oil bath to 60° C. until all of the solid had dissolved. The flask was then cooled to −78° C. and a solution of the product from Step 5A (5.67 g, 18.5 mmol.) in dry toluene (100 ml) was added slowly via cannula. This mixture was allowed to slowly warm to room temperature over 18 hours then 2N HCl (200 ml) added and the reaction stirred for 30 minutes. The layers were separated and the aqueous phase extracted with ethyl acetate (2×200 ml). The combined organics were washed with 2N HCl (400 ml), dried (MgSO$_4$) and evaporated to leave 21 g of an oily residue. This was chromatographed (SiO$_2$; ether:DCM:hexane; 1:0:3 to 1:1:3 gradient) to afford recovered (S,S)-1,2-bis[[3,5-bis (trifluoromethyl)phenyl] sulfonylamino]-1,2-diphenylethane (13.2 g after recrystallisation from DCM:hexane) and product vinyl acid (4.5 g, 79%). $^1$H NMR (CDCl) 7.36–7.31 (211, m), 7.11–6.96 (5H, m), 5.62 (1H, ddd, J=17.5, 10.5, 7.5 Hz), 4.90 (1H, dd, J=10.5, 1.0 Hz), 4.75 (1H, dd, J=17.5, 1.0 Hz), 3.94 (1H, dd, J=11.5, 7.5 Hz) and 3.84 (1H, d, J=11.5 Hz). [subsequent coupling to a homochiral amine gave a single isomer only and implied the e.e. of this product vinyl acid to be >95%].

Step 5C

To a solution of the product from Step 5B (167 mg, 0.55 mmol.) in dry DCM (20 ml) was added aminobenzodiazepine B (145 mg, 0.55 mmol.), EDC (115 mg, 0.60 mmol.) and HOBt (81 mg, 0.60 mmol.) and the resulting mixture stirred at ambient temperature for 18 hours. The solution was washed with 1N HCl (20 ml), 1N NaOH (20 ml), dried (MgSO$_4$) and evaporated. The residue was triturated with ether:hexane (2:1 v/v) to afford the product as a colourless solid (271 mg, 90%). $^1$H NMR (CDCl$_3$) 7.54–7.10 (15H, m), 7.03–6.98 (2H, m), 5.72 (1H, ddd, J=17.5, 10.5, 8.0), 5.24 (1H, d, J=8.0 Hz), 4.93 (1H, d, J=10.5 Hz), 4.79 (1H, d, J=17.5 Hz), 4.11 (1H, dd, J=11.0, 8.0 Hz), 3.77 (1H, d, J=11 Hz) and 3.36 (3H, s).

Step 5D

A solution of the product from Step 5C (270 mg, 0.49 mmol.) in MeOH (4 ml)/DCM (20 ml) was cooled to −78° C. under nitrogen. Using an ozonizer, oxygen was bubbled through the mixture for 5 minutes then ozone bubbled through for a further 20 minutes. After this time a blue colour had appeared. Ozone bubbling was stopped, but nitrogen bubbling continued at −78° C. until the blue colour had dissipated. Sodium borohydride (185 mg, 4.9 mmol.) was added, the cooling bath removed and the reaction stirred at ambient temperature for 2 hours. After this time, the solvent was removed in vacuo, MeOH (10 ml) added and the solvent removed again. The residue was taken up in ethyl acetate (50 ml) and washed with satd. aq. NR$_4$Cl (25 ml), dried (MgSO$_4$) and evaporated. Purification by chromatography. (SiO$_2$; ether:DCM; 1:1 v/v) afforded the product as a colourless powder (180 mg, 66%). $^1$H NMR (CDCl$_3$) 7.54–7.17 (15H, m), 7.05–7.00 (2H, m), 5.24 (1H, d, J=8.0 Hz), 3.95 (1H, d, J=9.5 Hz), 3.61–3.56 (3H, m) and 3.36 (3H, s).

Step 5E

To a stirred solution of the product from Step 5D (37 mg, 0.7 mmol.) in dry DCM (5 ml) was added carbon tetrabromide (26 mg, 0.08 mmol.) then triphenylphosphine (21 mg, 0.08 mmol.) and the resulting yellow solution stirred at ambient temperature for 2 hours. TLC analysis showed starting material to remain so further carbon tetrabromide (26 mg, 0.08 mmol.) then triphenylphosphine (21 mg, 0.08 mmol.) were added and the mixture gently refluxed for 90 minutes. The mixture was cooled, evaporated and chromatographed (SiO$_2$; ether:DCM; 1:1 then EtOAc:DCM 1:1 v/v) to afford the desired bromide (35 mg, 85%). $^1$H NMR (CDCl$_3$) 7.52–7.16 (15H, m), 7.07–7.03 (2H, m), 5.21 (1H, d, J=8.0 Hz), 3.94 (1H, d, J=11.0 Hz), 3.82–377 (1H, m), 3.43 (1H, dd, J=10.5, 3.0 Hz), 3.36 (3H, s) and 3.30 (1H, dd, J=10.5, 7.5 Hz).

The bromide (prepared as above, 28 mg, 0.05 mmol.) was dissolved in dry benzene (5 ml) and tributyl tin hydride (0.018 ml, 0.07 mmol.) and AIBN (5 mg, 0.03 mmol.) added. The mixture was then refluxed under nitrogen for 2.5 hours then cooled and evaporated. Purification by preparative TLC (SiO$_2$; ether:DCM:hexane; 1:1:2 v/v) gave the product. $^1$H NMR (CDCl$_3$) 7.51–7.10 (15H, m), 7.04–7.00 (2H, m), 5.23 (1H, d, J=8.0 Hz), 3.52 (2H, m), 3.35 (3H, s) and 1.04 (3H, m).

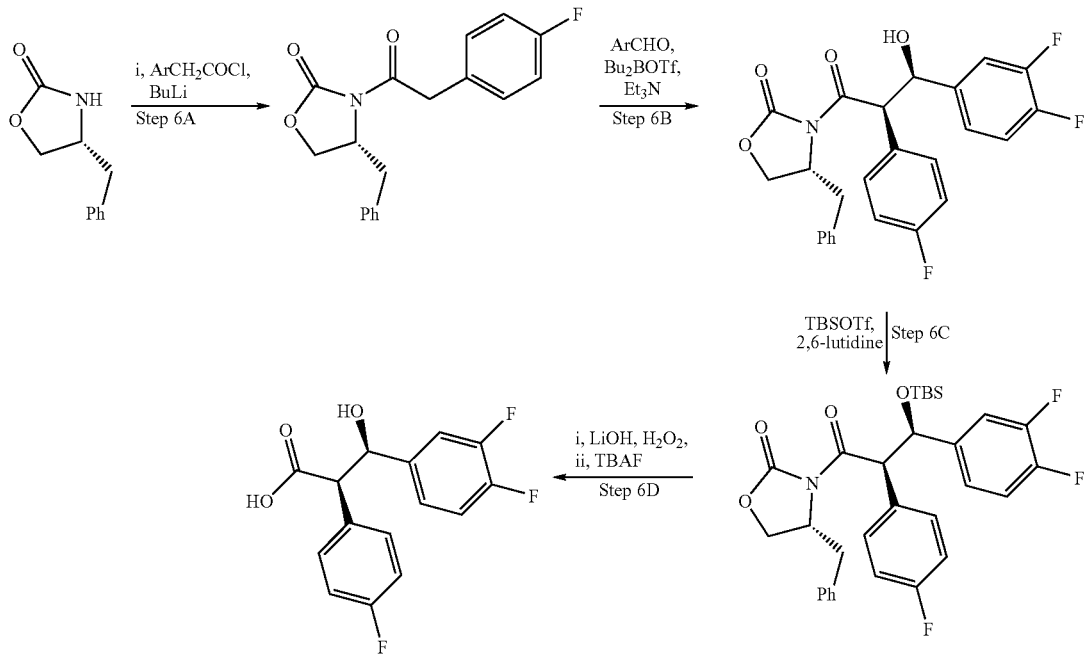

Scheme 6

Step 6A

To a stirred solution of 4-fluorophenylacetic acid (11.2 g, 73 mmol.) in THF (125 ml) at 0° C. under nitrogen was added oxalyl chloride (7.1 ml, 82 mmol.) then DMF (4 drops) and the resulting effervescing mixture stirred at 0° C. for 30 minutes then at ambient temperature for a further 1 hour. The effervescence had ceased after this time and the solvent was evaporated. To the residue was added toluene (50 ml) and the solvent evaporated. The addition of toluene and evaporation was repeated to leave a residue of 4fluorophenylacetyl chloride.

(R)-(+)4-Benzyl-2-oxazolidinone (11.7 g, 66 mmol.) was dissolved in THF (250 ml) and cooled to −78° C. under nitrogen. n-BuLi (46 ml of a 1.6M solution in hexane, 74 mmol.) was added dropwise over 15 minutes and the resultant pale orange solution stirred at −78° C. a further 15 minutes. After this time, the acid chloride (prepared above) as a solution in THF (50 ml) was added via cannula and the mixture stirred at −78° C. for 45 minutes then at room temperature for 1 hour. The reaction was quenched by the addition of satd. aq. NH$_4$Cl (200 ml) and the organics evaporated. The residue was extracted with DCM (2×200 ml) and the combined organic layers dried (MgSO$_4$) and evaporated to leave a residue which was purified by chromatography (SiO$_2$; ether:hexane; 1:1 (v/v)) to afford the product as colourless crystals (16.5 g, 80%). $^1$H NMR (CDCl$_3$) 7.33–7.22 (5H, m), 7.15–7.11 (2H, m), 7.07–7.01 (2H, m), 4.71–4.64 (1H, m), 4.32 (1H, d, J=16.0 Hz), 4.25–4.16 (3H, m), 3.25 (1H, dd, J=13.5, 3.5 Hz) and 2.76 (1H, dd, J=13.5, 9.5 Hz).

Step 6B

To a stirred solution of the product from Step 6A (10.28 g, 33 mmol.) in DCM (200 ml) at 0° C. under nitrogen was added dibutylboron triflate (39 ml of a 1.0M solution in DCM, 39 mmol.) then triethylamine (6.0 ml, 43 mmol.). The solution was stirred at 0° C. for 15 minutes then cooled to −78° C. and 3,4-diiluorobenzaldehyde (5.36 g, 38 mmol.) as a solution in DCM (20 ml) added via cannula. Stirring was continued for a further 30 minutes at −78° C. then the cooling bath removed and the reaction aged for 2.5 hours. The reaction was quenched by the addition of pH 7 buffer (50 ml) followed by the cautious, slow addition of 100 ml of 2:1 v/v MeOH:28% aq. H$_2$O$_2$ solution [CAUTION—very exothermic]. The mixture was stirred at room temperature for 1 hour then the organic layer evaporated and the residue extracted into ether (2×100 ml). The combined organic layers were washed with satd. aq. NaHCO$_3$ solution (100 ml), dried (MgSO$_4$) and evaporated to afford a solid which was triturated with ether:hexane (1:2 v/v, 100 ml) and filtered to afford the desired product as a colourless powder (12.0 g, 80%). $^1$H NMR (CDCl$_3$) 7.37–7.32 (2H, m), 7.25–7.18 (3H, m), 7.12–6.94 (7H, m), 5.34 (1H, d, J=6.0 Hz), 5.24 (1H, d, J=6.0 Hz), 4.67–4.61 (1H, m), 4.14–4.05 (2H, m), 3.1 (1H, br s), 3.08 (1H, dd, J=13.5, 3.5 Hz) and 2.58 (1H, dd, J=13.5, 9.0 Hz).

Step 6C

To a stirred solution of the product from Step 6B (13.2 g, 29 mmol.) in DCM (75 ml) at 0° C. under nitrogen was added 2,6-lutidine (8.4 ml, 73 mmol.) then TBSOTf (13.3 ml, 58 mmol.) and the mixture stirred at 0° C. for 3 hours. The reaction was diluted with ether (150 ml) and washed with 10% KHSO$_4$ solution (2×100 ml), satd. aq. NaHCO$_3$ solution (100 ml), dried (MgSO$_4$) and evaporated to afford a solid (20.3 g). The solid contained silyl residues but was used without further purification.

Step 6D

The crude product from Step 6C (20.3 g, 29 mmol. [theory]) was dissolved in TBF (130 ml) and cooled to 0° C. under nitrogen. To this was added hydrogen peroxide (14.1 ml of a 28% aq. solution, 116 mmol.) then LIOH (904 mg, 38 mmol. as a solution in water, 30 ml) and the resulting biphasic mixture vigorously stirred and allowed to attain room temperature over 3 hours. After this time, sodium sulfite (14.6 g, 116 mmol. as a solution in water, 50 ml) was added and the organics removed in vacuo. The aqueous residue was acidified to pH 1 with 2N HCl then extracted into DCM (3×100 ml) and the combined organics dried (MgSO$_4$) and evaporated to leave a residue (19.6 g) which was purified by chromatography (SiO$_2$; ether:DCM:hexane; 1:1:2 v/v) to afford the product 11.3 g (95% over 2 steps). $^1$H NMR (CDCl$_3$) 7.33–7.28 (2H, m), 7.02–6.98 (5H, m), 5.10 (1H, d, J=8.0 Hz), 3.73 (1H, d, J=8.0 Hz), 0.69 (9H, s) and 0.00 (6H, s).

To the carboxylic acid from above (11.3 g, 27.5 mmol.) was added TBAF (1.0M solution in THF, 140 ml, 140 mmol.) and the mixture stirred at ambient temperature for 18 hours then evaporated. The residue was partitioned between ether (200 ml) and 2N HCl (100 ml), the layers separated and the aqueous further extracted with ether (100 ml). The combined organic layers were washed with water (2×200 ml) and brine (100 ml), dried (MgSO$_4$) and evaporated to afford a residue (9.47 g) which was purified by chromatography (SiO$_2$; ether:DCM:hexane:acetic acid; 25:25:50:1 v/v). After removal of solvent, the resulting solid was co-evaporated with toluene (3×100 ml) to remove acetic acid residues affording the product as a white solid (6.2 g, 76%). $^1$H NMR (CDCl$_3$) 7.28–6.96 (7H, m), 5.28 (1H, d, J=6.5 Hz) and 3.81 (1H, d, J=6.5 Hz).

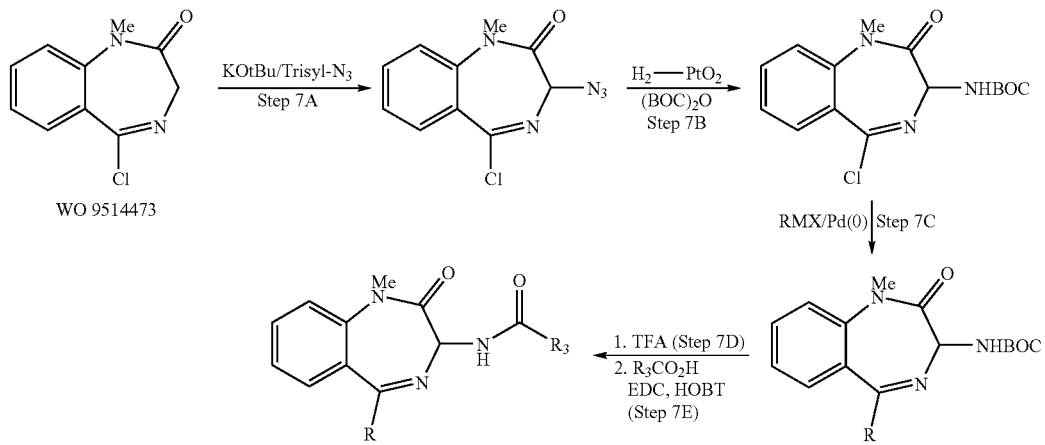

Scheme 7

Step 7A

A solution of 1-methyl-2-oxo-5-chloro-2,3-dihydro-1H-1,4-benzodiazepine (WO 9514473) (3.4 g) was dissolved in dry THF (120 ml) and cooled to −78° C. A solution of KOtBu (19 ml, 1.0 M in THF) was added dropwise. The solution was warmed to −30° C., held at that temperature for 5 mins, then re-cooled to −78° C. The reaction mixture was treated with a solution of trisyl azide (5.56 g) in THF (60 ml). After 5 min, glacial acetic acid (8.5 ml) was added and the reaction mixture was left to warm to room temperature overnight. The solvent was partially removed in vacuo and the residue was taken up in ethyl acetate-brine-water. The organic layer was separated, washed with brine, dried, filtered and evaporated. Purification by flash column chromatography gave the azide (2.3 g, 57%).

Step 7B

A solution of the foregoing azide (0.67 g) in dioxane (20 ml) was treated with $BOC_2O$ (0.63 g) and $PtO_2$ (20.6 mg) and hydrogenated at 40 psi at room temperature for 4 h. The reaction mixture was filtered through Celite®, washing with ethyl acetate. The reaction mixture was evaporated in vacuo and purified by column chromatography to give the BOC carbamate (0.58 g, 67%).

Step 7C (Representative Procedure)

A mixture of the foregoing BOC carbamate (230 mg) was treated with 2-(1-oxo-1,2-dihydroisoquinolin-6-yl)4,4,5,5-tetramethyl-1,3,2-dioxa-borolane (cf. N. Miyaura et al, *J. Org. Chem.*, 1995, 60, 7508–7510) (193 mg), $Pd(PPh_3)_4$ (82 mg), 2N aqueous $Na_2CO_3$ (1.06 ml) and DME (2 ml), degassed and heated at 100° C. for 10 minutes. The reaction mixture was cooled, extracted with ethyl acetate, washed with brine, dried, filtered and evaporated. The crude reaction product was purified by column chromatography to give the coupled product (320 mg, 100%).

Step 7D (Representative Procedure)

A solution of the foregoing coupled product (304 mg) in 20% TFA-DCM was stirred at room temperature for 1 h, evaporated in vacuo, azeotroped with toluene and purified by column chromatography to give the amine (154 mg, 68%).

Step 7E (Representative Procedure)

A solution of the foregoing amine (70 mg) in DMF (4 ml) was treated with EDC (56 mg), HOBT (39 mg) and (2R)-2-methyl-3-(3,4-difluorophenyl)propionic acid (46 mg) and stirred at room temperature for 2 h. The reaction mixture was diluted with ethyl acetate, washed with acid, base, brine and dried. Evaporation and purification by column chromatography gave the product (40 mg, 37%) as a mixture of diastereomers.

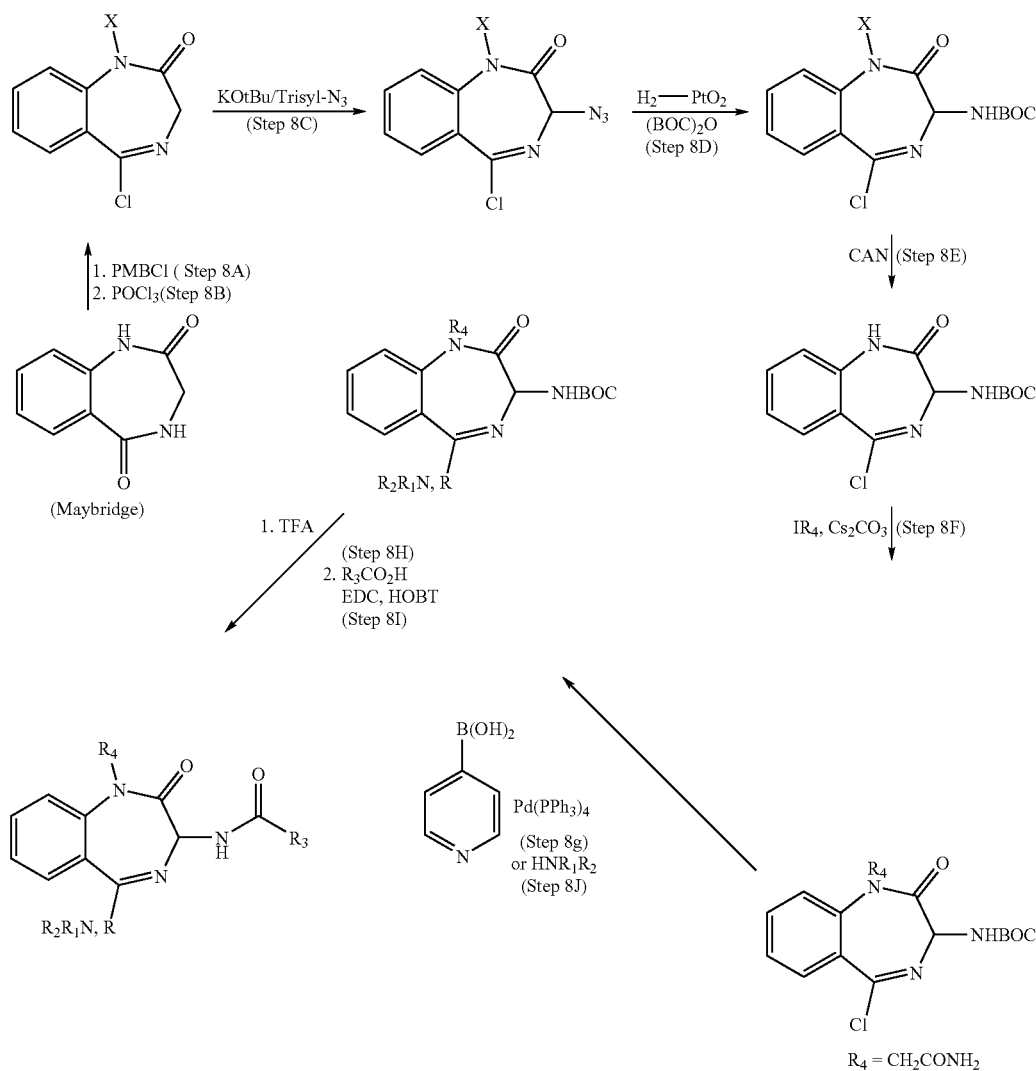

Step 8A

A suspension of 3,4-dihydro-1H-1,4-benzodiazepine-2,5-dione (commercially available), PMBCl (23 ml), $Cs_2CO_3$ (165 g) in DMF (750 ml) was stirred overnight at room temperature. The reaction mixture was filtered, evaporated in vacuo and partitioned between water and ethyl acetate. The aqueous layer was extracted with ethyl acetate, and the combined organic layers were dried, filtered and evaporated in vacuo. Trituration with hexane gave the alkylated lactam (25 g). Further product was obtained by column chromatography to give a total yield of 35 g (69%).

Step 8B

A solution of the foregoing alkylated lactam (4 g), N-N-dimethylaniline (3.7 ml), $POCl_3$ (1.35 ml) and benzene was refluxed for 7 h, then allowed to cool overnight. The reaction mixture was cooled to 0° C., treated with water (15 ml) and stirred for 30 min until the reaction mixture reached room temperature. The reaction mixture was poured into more water and ether. The organic layer was separated, washed, dried, filtered and evaporated. Purification by chromatography gave the chloroimidate (3.5 g, 77%). (360 MHz NMR, d6-DMSO) 7.73 (1H, d, J=7.5), 7.61–7.57 (2H, m), 7.34–7.30 (1H, m), 6.99 (2H, d, J=8.6), 6.81 (2H, d, J=8.6), 5.3 (1H, brd), 4.9 (1H, brd), 4.45 (1H, brd), 3.85 (1H, brd), 3.68 (3H,s).

Step 8C

A solution of the foregoing chloroimidate (24 g) was dissolved in TIF (500 ml), cooled to −78° C. and treated with a solution of KOtBu (122 ml, 1.0 M in THF). The reaction mixture was stirred for 30 min at −78° C., then treated with a solution of trisyl azide (28 g) in THF (100 ml) and stirred at −78° C. for 40 min. The reaction mixture was treated with acetic acid (70 ml), warmed to room temperature and stirred overnight. The reaction mixture was evaporated partially in vacuo, taken up in ethyl acetate-water, washed, dried, filtered and evaporated in vacuo. Purification by chromatography gave the azide (25 g, 92%).

Step 8D

A solution of the foregoing azide (25 g) in dioxane (300 ml) was treated with $BOC_2O$ (25 g), $PtO_2$ (2.5 g) and hydrogenated at 40 psi at room temperature for 3.5 h. The reaction mixture was filtered and purified by column chromatography to give the BOC-carbamate (22 g, 73%). (360 MHz NMR, d6-DMSO) 7.95 (1H, d, J=8.7), 7.78–7.68 (3H, m), 7.41–7.36 (1H, m), 6.93 (2H, d, J=8.6), 6.78 (2H, d, J=8.6), 5.37 (1H, d, J=15.5), 5.10 (1H, d, J=8.7), 4.89 (1H, d, J=15.5), 3.67 (3H, s), 1.39 (9H, s).

Step 8E (Representative Procedure)

A solution of the foregoing BOC carbamate (1 g) was dissolved in acetonitrile (45 ml) and water (15 ml) and cooled to −15° C. A solution of ceric ammonium nitrate (10 g) in water was added in one portion and the reaction mixture was stirred for 1 h, then diluted with ethyl acetate and water. The organic layer was washed with water and brine. Purification by a combination of trituration and chromatography gave the deprotected chloroimidate (360 mg, 51%), together with unchanged starting material (330 mg, 33%). (400 MHz NMR, d6-DMSO) 11.03 (1H, s), 7.85–7.82 (2H, m), 7.68–7.64 (1H, m), 7.37–7.33 (1H, m), 7.247.22 (1H, m), 4.98 (1H, d, J=8.7), 1.39 (9H, s).

Step 8F (Representative Procedure)

A solution of the foregoing deprotected chloroimidate (600 mg) in DMF (10 ml) was treated with iodoacetamaide (394 mg) and cesium carbonate (1.9 g) and stirred at room temperature for 1 h. The reaction mixture was diluted with ethyl acetate and brine, washed dried, filtered and evaporated. Purification by column chromatography gave the alkylated chloroimidate (620 mg, 87%).

(400 MHz NAR, d6-DMSO) 7.91–7.83 (2H, m), 7.77–7.72 (1H, m), 7.65 (1H, s), 7.48–7.43 (2H, m), 7.20 (1H, s), 5.08 (1H, d), 4.46 (1H, d), 4.33 (1H, d) 1.38 (9H, s).

Step 8G (Representative Procedure)

A mixture of the foregoing alkylated chloroimidate (200 mg) was treated with 4pyridyl boronic acid (101 mg), $Pd(PPh_3)_4$ (50 mg), 2 N aqueous $Na_2CO_3$ (1 ml) and DME (2 ml), degassed and heated at 80° C. for 120 minutes. The reaction mixture was cooled, extracted with ethyl acetate, washed with brine, dried, filtered and evaporated to give the crude coupled carbamate (100 mg).

Step 8H (Representative Procedure)

A solution of the foregoing coupled carbamate (100 mg) in TFA (10 ml) was stirred at room temperature for 10 min, evaporated in vacuo, azeotroped with toluene and purified by column chromatography to give the amine (40 mg, 24%).

Step 8I (Representative Procedure)

A solution of the foregoing amine (40 mg) in DMF (4 ml) was treated with EDC (30 mg), HOBT (21 mg) and (2S)-3-[3-fluoro-4-(trifiuoromethyl)phenyl]-2-methylpropanoic acid (35 mg) and stirred at room temperature for 2 h. The reaction mixture was diluted with ethyl acetate, washed with base, brine and dried. Evaporation and purification by column chromatography gave the title compound (35 mg, 51%) as a mixture of diastereomers. (360 MHz NMR, d6-DMSO) 9.3 (0.5H, d), 9.2 (0.5H, d), 8.68–8.64 (2H, m), 7.76–7.26 (11H, m), 5.40 (0.5H, d, J=8.4), 5.39 (0.5H, d, J=8.4), 4.654.39 (2H, m), 3.10–2.91 (2H, m), 2.75–2.63 (1H, m), 1.06 (1.5H, d, J=6.7), 1.02 (1.5 H, d, J=6.7).

Step 8J (Representative Procedure)

A mixture of the foregoing alkylated chloroimidate (150 mg) was treated with morpholine (5 ml), and heated in a sealed tube at 100° C. for 3 h. The reaction mixture was evaporated in vacuo and purified by column chromatography to give the title compound (110 mg, 64%).

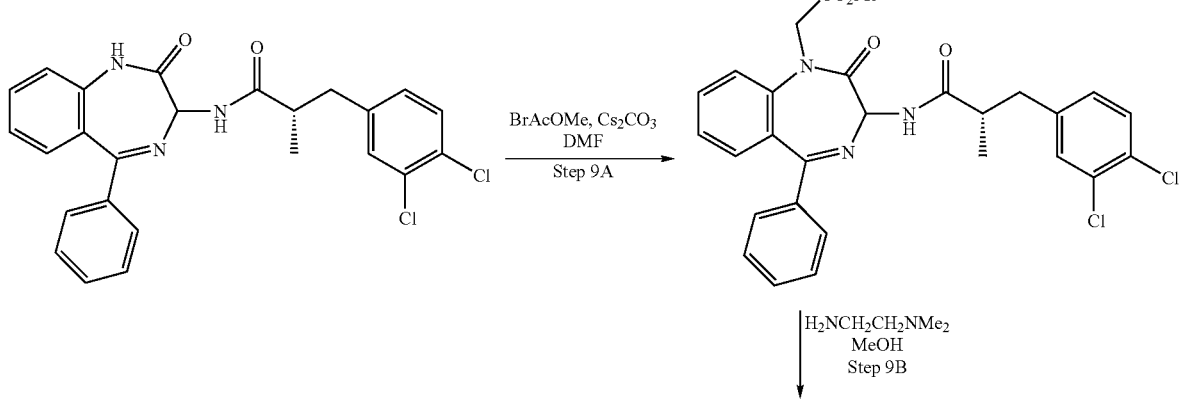

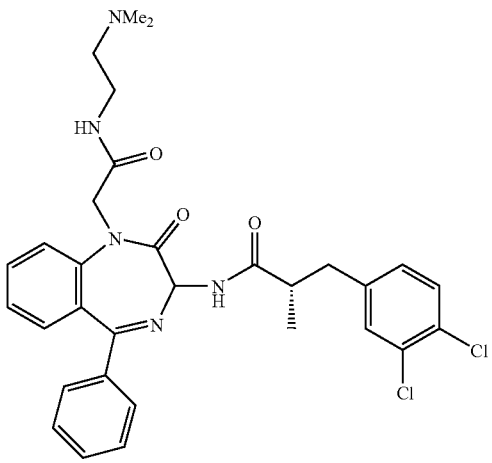

Step 9A.

(2S)-3-(3,4-dichlorophenyl)-2-methyl-N-(2-oxo-5-phenyl-2,3-dihydro-1H-1,4benzodiazepin-3-yl)propanamide (1.0 g) was dissolved in DMF and treated with cesium carbonate (2.1 g) and bromoacetic acid methyl ester (200□l), then left to stir at room temperature for 16 h. The mixture was partitioned between ethyl acetate and water and the organic layer washed (water, brine), dried (magnesium sulphate) and evaporated in vacuo. Purification by flash silica chromatography afforded {3-[3-(3,4-Dichlorophenyl)-2-methyl-propionylamino]-2-oxo-5-phenyl-2,3-dihydro-benzo[e][1,4]diazepin-1-yl}-acetic acid methyl ester.

Step 9B

The product from Step 9A (200 mg) was dissolved in methanol (5 ml) and treated with N,N-dimethylethylenediamine (2 ml). The reaction mixture was heated in a sealed tube at 70° C. for 5 hrs. The mixture was evaporated in vacuo and purified by flash silica chromatography to afford 3-(3,4-dichloro-phenyl)-N-[1-[(2-dimethylamino-ethylcarbamoyl)-methyl]-2-oxo-5-phenyl-2,3-dihydro-1H-benzo[e][1,4]diazepin-3-yl]-2-methyl-propionamide.

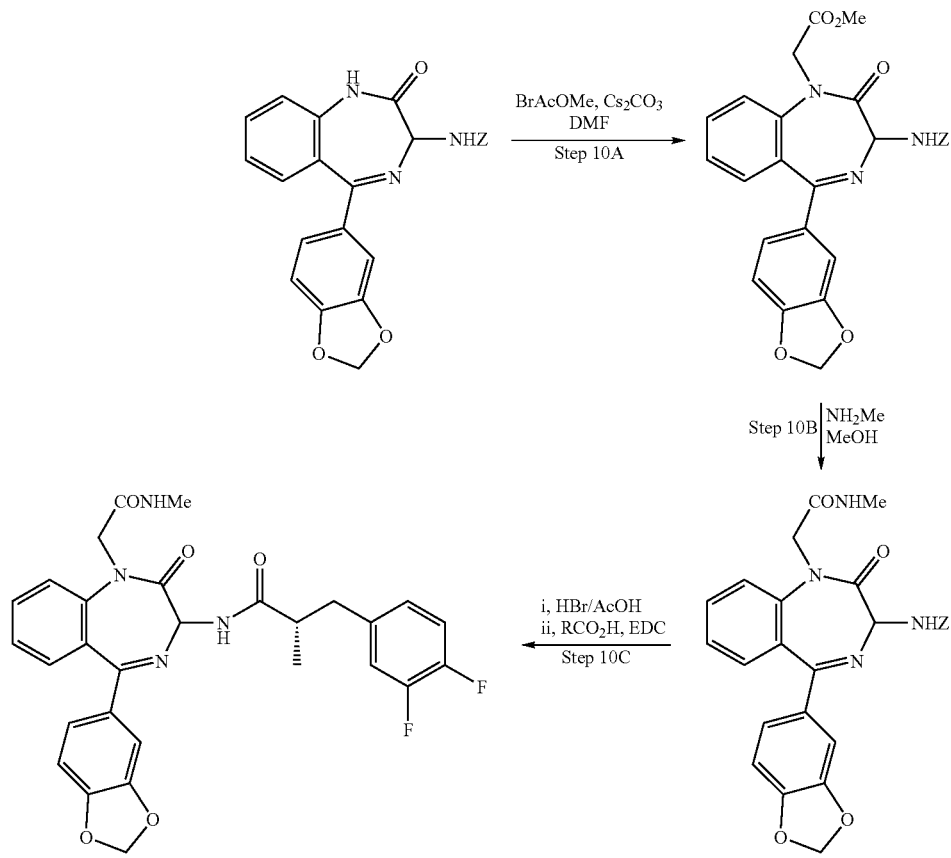

Step 10A (5-Benzo[1,3]dioxol-5-yl-2-oxo-2,3-dihydro-1H-benzo[e][1,4]diazepin-3-yl)-carbamic acid benzyl ester (prepared from 4-bromo-1,2-(methylene dioxy)benzene using methods analogous to *J. Chem. Soc., Perkin Trans* 1 1995, 203 and *J. Org. Chem.* 1995, 60, 730), (4 g) was converted to (5-benzo[1,3]dioxol-5-yl-3-benzyloxycarbonylamino-2-oxo-2,3-dihydro-benzo[e][1,4]diazepin-1-yl)-acetic acid methyl ester in an analogous fashion to Step 9A.

Step 10B

The product from Step 10A was dissolved in dioxane (4 ml) and treated with methylamine (1 ml). The reaction mixture was heated in a sealed tube at 50° C. until complete consumption of starting material. The mixture was evaporated in vacuo and purified by flash silica chromatography to afford (5-benzo[1,3]dioxol-5-yl-1-methylcarbamoylmethyl-2-oxo-2,3-dihydro-1H-benzo[e][1,4]diazepin-3-yl)-carbamic acid benzyl ester.

Step 10C

The product from Step 10B was deprotected with HBr as in Step 2D (Scheme 2) and coupled to a carboxylic acid as in Step 1E (Scheme 1).

Abbreviations:

EDC—1-(3-Dimethylaminopropyl)-3-ethylcarbodiimide hydrochloride
HOBt—Hydroxybenzotriazole hydrate
HBTU—O-(Benzotriazol-1-yl)-N,N,N',N'-tetramethyluronium hexafluorophosphate
TMB—2,4,6-Trimethoxybenzyl
Trisyl—2,4,6-Triisopropylbenzenesulfonyl
DMS—dimethyl sulphide
THF—tetrahydrofuran
DMF—N,N-dimethylformamide
AIBN—azaisobutyronitrile
DCM—dichloromethane
TBAF—tetrabutylammonium fluoride
TBS—tertbutyldimethylsilyl
PMB—para methoxybenzyl
CAN—ceric ammonium nitrate
TFA—trifluoroacetic acid
DME—dimethoxyethane
BOC—tertbutoxycarbonyl
OTf—triflate (trifluoromethanesulphonate)

Using the procedures described for Schemes 1–4, the following compounds were prepared.

Note:

(S)-3-amino-1-methyl-5-phenyl-1,3-dihydro-2H-benzo[e][1,4]diazepin-2-one, referred to as B in the examples, was prepared as described in *J. Org. Chem.* 1987, 52, 955 and 3232.

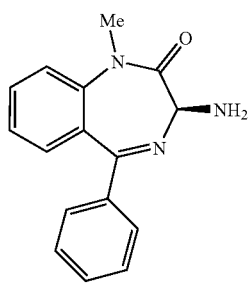

B

Carboxylic acids used in amide forming reactions (e.g. Step 1E, Step 3C) were prepared using methods well known in the literature (e.g. *Pure Appl. Chem.*, 1981, 53, 1109.)

Example 1

(±)-4-[3-(2,3-Diphenylpropionylanmino)-1-methyl-2-oxo-2,3-dihydro-1H-benzo[e][1,4]diazepin-5-yl]-benzamide Prepared by reaction of amine A and 2,3-diphenylpropionic acid using the procedure of Step 1E shown in Scheme 1.

($^1$H, CDCl$_3$) [ca. 3:1 mixture of diastereomers] 7.80 (2H, m), 7.60 (3H, m), 7.4–7.1 (14H, m), 6.18 (1H, br s), 5.72 (1H, br s), 5.47 (1H, d, J=8 Hz, major diast.), 5.44 (1H, d, J=8 Hz, minor diast.), 3.86 (1H, m), 3.67–3.49 (1H, m), 3.42 (3H, s, major diast.), 3.40 (3H, s, minor diast.) and 3.08 (1H, m); MS (ES+), MH$^+$=517.

Example 2

(±)-4-{3-[3-(2,4-Dichlorophenyl)-2-phenylpropionylamino]-1-methyl-2-oxo-2,3-dihydro-1H-benzo[e][1,4]diazepin-5-yl}-benzamide Prepared by reaction of amine A and 3-(2,4-dichlorophenyl)-2-phenylpropionic acid using the procedure of Step 1E shown in Scheme 1.

($^1$H, CDCl$_3$) [ca. 1.2:1 mixture of diastereomers] 7.82 (2H, d, J=7 Hz, minor diast.), 7.78 (2H, d, J=7 Hz, major diast.), 7.60 (3H, m), 7.41–7.22 (10H, m), 7.09 (1H, s), 7.00 (1H, m), 6.18 (1H, br s), 5.76 (1H, br s), 5.46 (1H, d, J=8 Hz major diast.), 5.43 (1H, d, J=8 Hz minor diast.), 3.97 (1H, t, J=7.5 Hz), 3.65–3.52 (1H, m), 3.43 (3H, s, major diast.), 3.40 (3H,. s, minor diast.) and 3.12 (1H, m); (ES+) MH$^+$=585.

Example 3

(±)-4-{3-[3-(3,4-Dichlorophenyl)-2-phenylpropionylamino]-1-methyl-2-oxo-2,3-dihydro-1H-benzo[e][1,4]diazepin-5-yl}-benzamide Prepared by reaction of amine A and 3-(3,4-dichlorophenyl)-2-phenylpropionic acid using the procedure of Step 1E shown in Scheme 1.

($^1$H, CDCl$_3$) [1:1 mixture of diastereomers] 7.82 and 7.79 (2H, d, J=7 Hz, diastereomers), 7.60 (3H, m), 7.49–7.20 (11H, m), 7.00–6.92 (1H, m), 6.16 (1H, br s), 5.80 (1H, br s), 5.44 and 5.42 (1H, d, J=8 Hz diastereomers), 3.79 (1H, m), 3.60–3.42 (1H, m), 3.43 and 3.40 (3H, s, diastereomers) and 3.04–2.96 (1H, m); (ES+) MH$^+$=585.

Example 4

(R)-{1-[5-(4Carbamoyl-phenyl)-1-methyl-2-oxo-2,3-dihydro-1H-benzo[e][1,4]diazepin-3-ylcarbamoyl]-2-phenylethyl}-carbamic acid tert-butyl ester Prepared by reaction of amine A and D-N-Boc-phenylalanine using the procedure of Step 1E shown in Scheme 1.

($^1$H, CDCl$_3$) [ca. 1:1 mixture of diastereomers) 7.85 (2H, m), 7.73–7.59 (3H, m), 7.41–7.24 (9H, m), 6.17 (1H, br s), 5.71 (1H, br s), 5.50 (1H, d, J=8 Hz), 5.05 (1H, m), 4.61 (1H, br m), 3.46 (3H, s), 3.27–3.05 (2H, m) and 1.42, 1.41 (9H, 2×s, diastereomers). MS (ES+) MH$^+$=556.

Example 5

(2S)-[1-[5-(4-Carbamoyl-phenyl)-1-methyl-2-oxo-2,3-dihydro-1H-benzo[e][1,4]diazepin-3-ylcarbamoyl]-2-(3,4-dichlorophenyl)-ethyl]-carbamic acid tert-butyl ester Prepared by reaction of amine A and L-N-Boc-3,4-dichlorophenylalanine using the procedure of Step 1E shown in Scheme 1.

($^1$H, CDCl$_3$) [ca. 1:1 mixture of diastereomers] 7.85–7.77 (3H, m), 7.68–7.60 (3H, m), 7.43–7.24 (5H, m), 7.18–7.10 (1H, m), 6.19 (1H, br s), 5.83 (1H, br s), 5.48 and 5.43 (1H, 2×d, J=8 Hz, diastereomers), 5.12 (1H, m), 4.59 (1H, br m), 3.48, 3.47 (3H, 2×s, diastereomers), 3.25–3.0 (2H, m) and 1.44, 1.42 (9H, 2×s, diastereomers); MS (ES+) MH$^+$=625.

Example 6

(2R)-1-[5-(4-Carbamoyl-phenyl)-1-methyl-2-oxo-2,3-dihydro-1H-benzo[e][1,4]diazepin-3-ylcarbamoyl]-2-(3,4-dichlorophenyl)-ethyl]-carbamic acid tert-butyl ester Prepared by reaction of amine A and D-N-Boc-3,4-dichlorophenylalanine using the procedure of Step 1E shown in Scheme 1.

($^1$H, CDCl$_3$) [ca. 1:1 mixture of diastereomers] 7.85–7.81 (3H, m), 7.68–7.60 (3H, m), 7.43–7.24 (5H, m), 7.16–7.12 (1H, m), 6.24 (1H, br s), 5.90 (1H, br s), 5.48 and 5.43 (1H. 2×d, J=8 Hz, diastereomers), 5.16 (1H, m), 4.60 (1H, br m), 3.47, 3.46 (3H, 2×s, diastereomers), 3.28–3.0 (2H, m) and 1.44, 1.42 (9H, 2×s, diastereomers); MS (ES+) MH$^+$=625.

Example 7

(±)-4-[1-Methyl-2-oxo-3-(2-phenoxypropionylamino)-2,3-dihydro-1H-benzo[e][1,4]diazepin-5-yl]-benzamide Prepared by reaction of amine A and (±)-2-phenoxypropionic acid using the procedure of Step 1E shown in Scheme 1.

($^1$H, CDCl$_3$) [ca. 2:1 mixture of diastereomers] 8.38 (1H, d, J=8 Hz, minor diast.), 8.30 (1H, d, J=8Hz, major diast.), 7.85–7.79 (2H, m), 7.72–7.59 (3H, m), 7.42–7.23 (5H, m), 7.05–7.00 (3H, m), 6.19 (1H, br s), 5.86 (1H, br s), 5.54 (1H, d, J=8 Hz, major diast.), 5.51 (1H, d, J=8 Hz, minor diast.), 4.86–4.78 (1H, m), 3.48 (3H, s, major diast.), 3.45 (3H, s, minor diast.), 1.69 (3H, d, J=7 Hz, minor diast.), 1.63 (3H, d, J=7 Hz, major diast.); MS (ES+), MH$^+$=457.

Example 8

4-[3-((2S)-2-Amino-3-(3,4-dichlorophenyl)propionylamino)-1-methyl-2-oxo-2,3-dihydro-1H-benzo[e][1,4]diazepin-5-yl]-benzamide (more polar diastereomer)

Prepared by reaction of amine A and L-N-Boc-3,4-dichlorophenylalanine using the procedure of Step 1E shown in Scheme 1 and subsequent deprotection.

($^1$H, CDCl$_3$) 7.85 (2H, m), 7.69 (2H, m), 7.63 (1H, m), 7.43–7.15 (6H, m), 7.15 (1H, m), 6.25 (1H, br s), 6.78 (1H, br s), 5.53 (1H, d, J=8 Hz), 3.71 (1H, dd, J=9,4 Hz), 3.49 (3H, s), 3.20 (1H, dd, J=14, 4 Hz), 2.90 (1H, dd, J=14,9 Hz); MS (ES+) MH$^+$=524.

Example 9

4-[3-((2R)-2-Amino-3-(3,4dichlorophenyl)propionylamino)-1-methyl-2-oxo-2,3-dihydro-1H-benzo[e][1,4]diazepin-5-yl]-benzamide (more polar diastereomer)

Prepared by reaction of amine A and D-N-Boc-3,4-dichlorophenylalanine using the procedure of Step 1E shown in Scheme 1 and subsequent deprotection.

($^1$H, CDCl$_3$) 7.85 (2H, m), 7.69 (2H, m), 7.63 (1H, m), 7.43–7.15 (6H, m), 7.11 (1H, m), 6.25 (1H, br s), 6.78 (1H, br s), 5.50 (1H, d, J=8 Hz), 3.74 (1H, d, J=9,4 Hz), 3.49 (3H, s), 3.24 (1H, dd, J=14, 4 Hz), 2.75 (1H, dd, J=14,9 Hz), MS (ES+) MH$^+$=524.

Example 10

4-{3-[(2R)-2-(1,3-Dihydroisoindol-2-yl)-3-phenyl-propionylamino]-1-methyl-2-oxo-2,3-dihydro-1H-[e][1,4]diazepin-5-yl}-benzamide Prepared by reaction of amine A and 2-(1,3-dihydroisoindol-2-yl)-3-phenyl-propionic acid using the procedure of Step 1E shown in Scheme 1.

MS (ES+) MH$^+$=558.

Example 11

4-[3-((2R)-2-Dimethylamino3-phenyl-propionylamino)-1-methyl-2-oxo-2,3-dihydro-1H-benzo[e][1,4]diazepin-5-yl]-benzamide Prepared by reaction of amine A and 2-dimethylamino-3-phenyl-propionic acid using the procedure of Step 1E shown in Scheme 1.

MS (ES+) MH$^+$=484.

Example 12

(±)-4-[1-Methyl-2-oxo-3-(4,4,4-trifluoro-2-methyl-butyrylamino)-2,3-dihydro-1H-benzo[e][1,4]diazepin-5-yl]-benzamide (1:1 mixture of diastereomers)

Prepared by reaction of amine A and 4,4,4-trifluoro-2-methyl-butyric acid using the procedure of Step 1E shown in Scheme 1.

($^1$H, d$_6$-DMSO) 9.40 (1H, d, J=10 Hz), 8.1 (1H, br s), 7.94 (2H, dd, J=1.4, 8.5 Hz), 7.73 (1H, m), 7.67 (1H, br d, J=9 Hz), 7.61 (2H, d, J=8.1 Hz), 7.45 (1H, br s), 7.30–7.37 (2H, m), 5.29 (1H, d, J=8.1 Hz), 3.39 (3H, s), 3.00–3.07 (1H, m), 2.55–2.68 (1H, m), 2.21–2.42 (1H, m), 1.17 (3H, d, J=6.9 Hz). MS (ES$^+$) MH$^+$=447.

Example 13

(±)-4-[1-Methyl-3-(2-methyl-3-phenyl-propionylamino)-2-oxo-2,3-dihydro-1H-benzo[e][1,4]diazepin-5-yl]-benzamide (3:2 mixture of diastereomers)

Prepared by reaction of amine A and 2-methyl-3-phenyl-propionic acid using the procedure of Step 1E shown in Scheme 1.

($^1$H, CDCl$_3$) 1.22 (3H, d, J=6.4 Hz, minor diast.), 1.26 (3H, d, J=6.5 Hz, major diast.), 2.72 (2H, m) 3.12 (1H, m,), 3.47 (3H, s, minor diast.), 3.49 (3H, s, major diast.), 5.50 (1H, d, J=8.1 Hz, minor diast.), 5.52 (1H, d, J=8.3 Hz, major diast.), 5.68 (1H, br s), 6.14 (1H, br s), 7.22 (1H, m,), 7.31

(2H, m,), 7.33 (1H, m,), 7.36 (2H, m,), 7.38 (2H, m), 7.40 (1H, m), 7.58–7.69 (3H, m), 7.83 (2H, m); MS(ES+): MH$^+$=455.

Example 14

(±)-4-{3-[3-(2,4-Dichloro-phenyl)-2-methyl-propionylamino]-1-methyl-2-oxo-2,3dihydro-1H-benzo[e][1,4]diazepin-5-yl}-benzamide Prepared by reaction of amine A and 3-(2,4-dichlorophenyl)-2-methyl-propionic acid using the procedure of Step 1E shown in Scheme 1.

Less polar diastereomer ($^1$H, CDCl$_3$): 1.26 (3H, m), 2.87 (2H, m), 3.12 (1H, m), 3.46 (3H, s), 5.49 (1H, d, J=8.2 Hz), 5.63 (1H, br s), 6.09 (1H, br s), 7.20 (3H, m), 7.26 (2H, m), 7.41 (2H, m), 7.63 (3H, m), 7.84 (2H, m) More polar diastereomer ($^1$H, CDCl$_3$): 1.29 (3H, d, J=6.3 Hz), 2.83 (2H, m), 3.11 (1H, dd, J=9.9 and 16.1 Hz), 3.47 (3H, s), 5.44 (1H, d, J=7.8 Hz), 5.65 (1H, br s), 6.10 (1H, br s), 7.13 (2H, m), 7.31 (3H, m), 7.39 (2H, m), 7.67 (1H, m), 7.68 (2H, d, J=8.4 Hz), 7.83 (2H, d, J=8.4 Hz).

Example 15

(±)-4-{3-[3-(2,4-Dichlorophenyl)-2,2-dimethyl-propionylamino]-1-methyl-2-oxo-2,3-dihydro-1H-benzo[e][1,4]diazepin-5-yl}-benzamide Prepared by reaction of amine A and 3-(2,4dichlorophenyl)-2,2-dimethyl-propionic acid using the procedure of Step 1E shown in Scheme 1.

($^1$H, CDCl$_3$): 1.32 (3H, s), 1.35 (3H, s), 3.13 (2H, m), 3.49 (3H, s), 5.51 (1H, d, J=7.6 Hz), 5.60 (1H, br s), 6.0 (1H, br s), 7.15 (1H, m), 7.32 (3H, m), 7.39 (2H, m), 7.43 (1H, m), 7.63 (1H, m), 7.70 (2H, d, J=8.4 Hz), 7.85 (2H, d, J=8.3 Hz); MS(ES+); MH$^+$=537.

Example 16

4-{3-[(2S)-3-(2,4-Dichlorophenyl)-2-dimethylaminopropionylamino]-1-methyl-2-oxo-2,3-dihydro-1H-benzo[e][1,4]diazepin-5-yl}-benzamide Prepared by reaction of amine A and (S)-(2,4-dichlorophenyl)-2-dimethylaminopropionic acid using the procedure of Step 1E shown in Scheme 1.

Less polar diastereomer ($^1$H, CDCl$_3$): 2.45 (6H, s), 2.99 (1H, dd, J=5.4 and 13.9 Hz), 3.18 (1H, dd, J=7.7 and 13.9 Hz), 3.43 (1H, dd, J=5.4 and 7.7 Hz), 3.45 (3H, s), 5.52 (1H, d, J=8.6 Hz), 5.63 (1H, br s), 6.08 (1H, br s), 7.17–7.31 (7H, m), 7.37 (1H, m), 7.59 (1H, m), 7.70 (2H, m), 7.84 (2H, m), 8.54 (1H, d, J=8.6 Hz); MS(ES+): MH$^+$=484. More polar diastereomer ($^1$H, CDCl$_3$): 2.43 (6H, s), 2.92 (1H, dd, J=5.4 and 13.9 Hz), 3.19 (1H, dd, J=7.4 and 13.8 Hz), 3.46 (1H, dd, J=5.4 and 7.4 Hz), 3.49 (3H, s), 5.55 (1H, d, J=8.7 Hz), 5.64 (1H, br s), 6.10 (1H, br s), 7.17–7.32 (7H, m), 7.39 (1H, m), 7.60 (1H, m), 7.66 (2H, m), 7.82 (2H, m), 8.72 (1H, d, J=8.6 Hz); MS(ES+): MH$^+$=484.

Example 17

(±)-4-{3-[2–2,4-Dichlorobenzyl)-pent-4-enoylamino]-1-methyl-2-oxo-2,3-dihydro-1H-benzo[e][1,4]diazepin-5-yl}-benzamide Prepared by reaction of amine A and 2-(2,4-dichlorobenzyl)-pent-4-enoic acid using the procedure of Step 1E shown in Scheme 1.

Less polar diastereomer ($^1$H, CDCl$_3$): 2.33 (1H, m), 2.52 (1H, m), 2.78 (1H, m), 3.03 (2H, m), 3.45 (3H, s), 5.11 (2H, m), 5.46 (1H, d, J=8.1 Hz), 5.61 (1H, br s), 5.86 (1H, m), 6.15 (1H, br s), 7.15–7.28 (3H, m), 7.32 (2H, m), 7.40 (2H, m), 7.61 (3H, m), 7.84 (2H, dd, J=1.7 and 6.7 Hz); MS(ES+):MH$^+$=549. More polar diastereomer ($^1$H, CDCl$_3$): 2.35 (1H, m), 2.57 (1H, m), 2.79 (1H, m), 2.94 (1H, dd, J=8.6 and 13.7 Hz), 3.02 (1H, dd, J=6.0 and 13.7 Hz), 3.45 (3H, s), 5.17 (2H, m), 5.40 (1H, d, J=7.8 Hz), 5.65 (1H, br 6), 5.91 (1H, m), 6.09 (1H, br s), 7.09 (2H, dd, J=2.1 and 8.2 Hz), 7.15 (2H, d, J=8.2 Hz), 7.26–7.31 (2H, m), 7.38 (2H, m), 7.61 (1H, m), 7.66 (2H, d, J=8.4 Hz), 7.82 (2H, d, J=8.4 Hz); MS(ES+): MH$^+$=549.

Example 18

(±)-4-{3-[3-(3,4-Dichlorophenyl)-2-(2-methylpropyl)-propionylamino]-1-methyl-2-oxo-2,3-dihydro-1H-benzo[e][1,4]diazepin-5-yl}-benzamide (5:4 mixture of diastereomers)

Prepared by reaction of amine A and 3-(3,4-dichlorophenyl)-2-(2-methylpropyl)-propionic acid using the procedure of Step 1E shown in Scheme 1.

($^1$H, CDCl$_3$) 0.92 (6H, d, J=5.6 Hz, minor diast.), 0.95 (6H, d, J=5.6 Hz, major diast.), 1.34 (2H, m), 1.76 (1H, m), 2.61 (1H, m), 2.72 (1H, m), 2.88 (1H, ddd, J=8.5, 12.7 and 13.3 Hz, minor diast.), 2.97 (1H, ddd, J=9.0, 13.4 and 13.6, major diast.), 3.45 (3H, s), 5.40 (1H, d, J=7.7, minor diast.), 5.48 (1H, d, J=8.4, major diast.), 5.60 (1H, br s), 6.05 (1H, br s) 7.15 (2H, m), 7.26–7.42 (5H, m), 7.62 (3H, m), 7.83 (2H, m); MS(ES+), MH$^+$:565.

Example 19

(±)-4-{3-[3-(3,4-Dichlorophenyl)-2-thiophen-3-yl-propionylamino]-1-methyl-2-oxo-2,3-dihydro-1H-benzo[e][1,4]diazepin-5-yl}-benzamide (5:4 mixture of diastereomers)

Prepared by reaction of amine A and 3-(3,4-dichlorophenyl) 2-thiophen-3-yl-propionic acid using the procedure of Step 1E shown in Scheme 1.

($^1$H, CDCl$_3$) 3.02 (1H, m), 3.40 (1H, m), 3.43 (3H, S, major diast.), 3.45 (3H, s, minor diast.), 3.90 (1H, dd, J=7.6 Hz), 5.45 (1H, d, J=8.0 Hz), 6.94–7.16 (3H, m), 7.22–7.41 (6H, m), 7.62 (4H, m), 7.82 (2H, dd, J=8.4 and 10.2 Hz); MS (ES+): MH$^+$: 591.

Example 20

(±)-4-{3-[3-(3,4-Dichlorophenyl)-2-dimethylaminomethyl-propionylamino]-1-methyl-2-oxo-2,3-dihydro-1H-benzo[e][1,4]diazepin-5-yl}-benzamide (2:1 mixture of diastereomers)

Prepared by reaction of amine A and 3-(3,4dichlorophenyl)-2-dimethylaminomethyl-propionic acid using the procedure of Step 1E shown in Scheme 1.

($^1$H, CDCl$_3$): 2.32 (1H, m), 2.36 (7H, m), 2.77 (2H, m), 3.09 (1H, m), 3.46 (3H1, s), 5.50 (1H, d, J=7.5 Hz, major diast.), 5.53 (1H, d, J=7.5 Hz, minor diast.), 5.70 (1H, br s), 6.17 (1H, br s), 7.07 (1H, m), 7.24 (1H, m), 7.26–7.40 (5H, m), 7.58–7.69 (3H, m), 7.83 (2H, m); MS(ES+); MH$^+$:566.

Example 21

(±)-4-{3-[3-(3,4-Dichlorophenyl)-2-methoxy-propionylamino]-1-methyl-2-oxo-2,3-dihydro-1H-benzo[e][1,4]diazepin-5-yl}-benzamide Prepared by reaction of amine A and 3-(3,4-dichlorophenyl)-2-methoxy-propionic acid using the procedure of Step 1E shown in Scheme 1.

Less polar diastereomer ($^1$H, CDCl$_3$) 3.03 (1H, dd, J=7.2 and 14.3 Hz), 3.14 (1H, dd, J=4.0 and 14.3 Hz), 3.47 (3H, s), 3.51 (3H, s), 3.91 (1H, dd, J=4.0 and 7.2 Hz), 5.51 (1H, d, J=8.6 Hz), 5.68 (1H, br s), 6.09 (1H, br s), 7.16 (1H, dd, J=2.0 and 8.2 Hz), 7.24–7.42 (5H, m), 7.63 (3H, m), 7.85 (2H, d, J=8.5 Hz), 8.14 (1H, d, J=8.5 Hz); MS(ES+): MH$^+$=539. More polar diastereomer ($^1$H, CDCl$_3$) 2.94 (1H, dd, J=7.7 and 14.2 Hz), 3.10 (1H, dd, J=3.7 and 14.2), 3.47 (3H, s), 3.48 (3H, s), 3.95 (1H, dd, J=3.7 and 7.7 Hz), 5.43 (1H, d, J=8.1 Hz), 5.62 (1H, br s), 6.08 (1H, br s), 7.11 (1H, dd, J=2.0 and 8.2 Hz), 7.24–7.36 (4H, m), 7.43 (1H, d, J=8.2 Hz), 7.62 (1H, m), 7.69 (1H, d, J=8.3 Hz), 7.83 (2H, d, J=8.3 Hz), 8.23 (2H, d, J=8.0 Hz); MS(ES+): MH$^+$=539.

Example 22

(±)-4-[1-Methyl-2-oxo-3-(2-phenyl-2-phenylsulfanyl-acetylamino)-2,3-dihydro-1H-benzo[e][1,4]diazepin-5-yl]-benzamide (1:1 mixture of diastereomers)

Prepared by reaction of amine A and 2-phenyl-2-phenylsulfanyl-acetic acid using the procedure of Step 1E shown in Scheme 1.

($^1$H, CDCl$_3$) 3.41 (3H, s), 5.25 (1H, d, J=9.0 Hz), 5.58 (1H, s), 7.19–7.58 (15H, m), 7.66–7.78 (2H, m), 7.91 (2H, d, J=8.5 Hz); MS (ES+), MH$^+$=535.

Example 23

(±)-4-{3-[2-(3,4-Dichlorophenoxy)-propionylamino]-1-methyl-2-oxo-2,3-dihydro-1H-benzo[e][1,4]diazepin-5-yl}-benzamide (1:1 mixture of diastereomers)

Prepared by reaction of amine A and 2-(3,4-dichlorophenoxy)-propionic acid using the procedure of Step 1E shown in Scheme 1.

($^1$H, d$_6$-DMSO) 9.52 (1H, s), 9.49 (1H, s), 9.47 (1H, s), 9.45 (1H, s), 8.09 (1+1H, brs), 7.95 (2+2H, d, J=8.2 Hz), 7.76–7.26 (1H, m), 7.01 (1+1H, m), 5.32 (1H, d, J=7.7 Hz), 5.29 (1H, d, J=7.7 Hz), 5.12 (1H, m), 5.07 (1H, m), 3.01 (3+3H, s (coincident)), 1.49 (3+3H, d (coincident), J=6.4 Hz); MS (ES+) MH$^+$=525.

Example 24

4-{3-[3-(3,4-Dichlorophenyl)-2-methyl-propionylamino]-1-methyl-2-oxo-2,3-dihydro-1H-benzo[e][1,4]diazepin-5-yl}-benzamide Prepared by reaction of amine A and 3-(3,4-dichlorophenyl)-2-methyl-propionic acid using the procedure of Step 1E shown in Scheme 1.

$^1$H NMR (DMSO) (1:1 mixture of diastereomers) 0.99–1.05 (3H, m), 2.56–2.63 (1H, m), 2.82–2.99 (2H,m), 3.38 (3H, m), 5.26–5.31 (1H, m), 7.21–7.38 (3H, m), 7.48–7.77 (8H, m), 7.92 (2H, m), 8.10 (1H, vbs). MS (ES+), MH$^+$=522.

Example 25

4-{3-[3-(3,4Difluorophenyl)-2-methyl-propionylamino]-1-methyl-2-oxo-2,3-dihydro-1H-benzo[e][1,4]diazepin-5-yl}-benzamide Prepared by reaction of amine A and 3,4-(difluorophenyl)-2-methyl-propionic acid using the procedure of Step 1E shown in Scheme 1.

$^1$H NMR (CDCl$_3$)= (1:1 mixture of diastereomers) 1.23–1.29 (3H, m), 2.64–2.71 (2H, m), 2.96–3.07 (1H, m), 3.46 (3H, s), 5.45–5.51 (1H, m), 5.60–5.90 (1H, v br s), 5.90–6.20 (1H, v br s), 6.90–7.13 (3H, m), 7.26–7.42 (4H, m), 7.59–7.64 (3H, m), 7.80–7.88 (2H, m).

Example 26

(±)-4-[3-[3-(2,4-Dichlorophenyl)-2-phenyl-propionylamino]-1-(3-hydroxypropyl)-2-oxo-2,3-dihydro-1H-benzo[e][1,4]diazepin-5-yl]-benzamide tert-butyl 1-(3-{[tert-butyl(dimethyl)silyl]oxy}propyl)-2,5-dioxo-1,2,3,5-tetrahydro-4H-benzo[e][1,4]diazepin-4-carboxylate was prepared analogously to tert-butyl 1-methyl-2,5-dioxo-1,2,3,5-tetrahydro-4H-benzo[e][1,4]diazepine4carboxylate (Scheme 1) i.e. WO 97/49690. This was subjected to procedures analogous to Steps 1A, 1B, 1C, 1D and finally reacted with 3-[3-(2,4-dichlorophenyl)-2-phenyl-propionic acid using the procedure of Step 1E shown in Scheme 1.

($^1$H, CDCl$_3$) (1:1 mixture of diastereomers) 7.82 (1H, d, J=8.1 Hz), 7.60–6.97 (16H, m), 6.12 (1H, brs), 5.67 (1H, brs), 5.45 (1H, d, J=8.1 Hz), 4.43 (1H, m), 3.96 (1H, m), 3.80 (1H, m), 3.58 (1H, m), 3.36 (1H, m), 3.27 (1H, m), 3.12 (1H, m), 1.73 (1H, m), 1.52 (1H, m); MS (ES+) MH$^+$=629.

Example 27

(±)-4-[3-[3-(2,4Dichlorophenyl)-2-phenyl-propionylamino]-1-(3-dimethylamino-propyl)-2-oxo-2,3-dihydro-1H-benco[e][1,4]diazepin-5-yl]-benzamide hydrochloride salt Prepared from (±)-4-[3-[3-(2,4-dichlorophenyl)-2-phenyl-propionylamino]-1-(3-hydroxypropyl)2-oxo-2,3-dihydro-1H-benzo[e][1,4]diazepin-5-yl]-benzamide via the mesylate using methods well known in the literature.

($^1$H, CDCl$_3$) (1:1 mixture of diastereomers) 7.84 (1H, d, J=8.2 Hz), 7.78 (1H, d, J=8.2 Hz), 7.47–6.99 (16+16H, m), 6.25 (1+1H, brs), 5.90 (1+1H, brs), 5.45 (1H, d, J=8.0 Hz), 5.42 (1H, d, J=8.0 Hz), 4.36 (1+1H, m), 3.97 (1+1H, m), 3.76–3.52 (2+2H, m), 3.12 (1+1H, m), 2.06 (2+2H, m), 2.03 (3+3H, s) 2.01 (3+3H, s), 1.61 (2+2H, m); MS (ES+), MH$^+$=656.

Example 28

(2S)-3-(3,4-Dichlorophenyl)-2-methyl-N-[1-methyl-2-oxo-5-(2,4,6-trimethyl-1-piperidinyl)-2,3-dihydro-1H-benzo[e][1,4]diazepin-3-yl]-propionamide Prepared from 3-amino-1-methyl-5-(2,4,6-trimethyl-1-piperidinyl)-1,3-dihydro-2H-benzo[e][1,4]diazepin-2-one (WO94/03437) and 3-(3,4-dichlorophenyl)-2-methyl propionic acid using the procedure of Step 1E shown in Scheme 1.

Less polar diastereomer ($^1$H, CDCl$_3$) 7.66 (1H, br s), 7.49 (1H, t, 8.5 Hz), 7.31 (1H, d, J=8 Hz), 7.28–7.21 (2H, m), 7.02 (2H, d, J=8 Hz), 6.91 (1H, br), 5.17 (1H, d, J=8 Hz), 3.68 (1H, br m), 3.39 (3H, s), 2.96 (1H, m), 2.67–2.55 (2H, m), 1.81 (1H, br in), 1.7–1.5 (4H, br m), 1.19 (3H, d, J=6.5 Hz), 1.15–0.8 (7H, br m) and 0.93 (3H, d, J=6.5 Hz); MS (ES+) MH$^+$=529. More polar diastereomer ($^1$H, CDCl$_3$) 7.68 (1H, br), 7.48 (1H, t, 8.5 Hz), 7.31–7.21 (3H, m), 7.04 (2H, d, J=8 Hz), 6.93 (1H, br), 5.20 (1H, d, J=8 Hz), 3.64 (1H, br m), 3.39 (3H, s), 3.00 (1H, m), 2.62–2.57 (2H, m), 1.82 (1H, br m), 1.75–1.5 (4H, br m), 1.20 (3H, d, J=6.5 Hz) and 1.15–0.8 (10H, br m); MS (ES+) MH+=529.

Example 29

N-(7-Chloro-2-oxo-5-phenyl-2,3dihydro-1H-benzo[e][1,4]diazepin-3-yl)-(2R)-3-(3,4-dichlorophenyl)-2-thiopen-2-yl-propionamide Prepared from 3-amino-7-chloro-5-phenyl-1,3-dihydro-2H-benzo[e][1,4]diazepin-2-one (commercially available) and (2R)-3-(3,4-dichlorophenyl)-2-thiophen-2-yl-propionic acid using the procedure of Step 1E shown in Scheme 1.

Less polar diastereomer ($^1$H, CDCl$_3$) 3.11 (1H, dd, J=7.6 and 13.8 Hz), 3.47 (1H, dd, J=7.4 and 16.7 Hz), 4.11 (1H, dd, J=7.6 Hz), 5.47 (1H, d, J=7.9 Hz), 6.97 (3H, m), 7.08 (1H, d, J=8.6 Hz), 7.22 (1H, d, J=7.9 Hz), 7.26–7.39 (4H, m), 7.46–7.55 (5H, m), 7.98 (1H, m); MS(ES+): MH+=568. More polar diastereomer (1H, CDCl$_3$) 3.08 (1H, dd, J=7.4 and 13.7 Hz), 3.52 (1H, dd, J=7.7 and 13.8 Hz), 4.10 (1H, dd, J=7.6 Hz), 5.47 (1H, d, J=7.8 Hz), 6.95 (2H, m), 7.02 (2H, m), 7.17–7.52 (10H, m), 8.22 (1H, d, J=9.1 Hz); MS(ES+): MH+=568.

Example 30

(2S)-3-(3,4-Dichlorophenyl)-2-methyl-N-(7-chloro-2-oxo-5-phenyl-2,3-dihydro-1H-benzo[e][1,4]diazepin-3-yl)-propionamide Prepared from 3-amino-7-chloro-5-phenyl-1,3-dihydro-2H-benzo[e][1,4]diazepin-2one (commercially available) and (2S)-3-(3,4-dichlorophenyl)-2-methyl-propionic acid using the procedure of Step 1E shown in Scheme 1.

($^1$H, CDCl$_3$) 1.27 (3H, d, J=7 Hz), 2.69 (2H, m), 3.03 (1H, m), 5.47 (1H d, J=7.9 Hz), 7.08 (3H, m), 7.26 (1H, m), 7.29 (2H, m), 7.35 (2H, m), 7.50–7.53 (4H, m), 7.78 (1H, s); MS(CI+), MH+: 502.

Example 31

(2S)-3-(3,4-Dichlorophenyl)-2-methyl-N-(7-chloro-1-methyl-2-oxo-5-phenyl-2,3-dihydro-1H-bezo[e][1,4]diazepin-3-yl)-propionamide Prepared from (2S)-3-(3,4-dichlorophenyl)-2-methyl-N-(7-chloro-2-oxo-5phenyl-2,3dihydro-1H-benzo[e][1,4]diazepin-3-yl)-propionamide by treatment with methyl iodide (c.f Step 2B, Scheme 2) ($^1$H, CDCl$_3$) 1.27 (3H, d, J=7 Hz), 2.68 (2H, m), 2.96 (1H, m), 3.43 (3H, s), 5.41 (1H, d, J=7.9 Hz), 7.05 (1H, m), 7.14 (1H, m), 7.32–7.36 (4H, m), 7.41 (2H, m), 7.48 (1H, m), 7.54–7.58 (3H, m); MS(CI+): MH+:516.

Example 32

(2R)-3-(3,4-Dichlorophenyl)-N-(1-methyl-2-oxo-5-piperidin-1-yl-2,3-dihydro-1H-benzo[e][1,4]diazepin-3-yl)-2-phenyl-propionamide (1:1 mixture of diastereomers).

Prepared from 3-amino-1-methyl-5-piperidin-1-yl-1,3-dihydro-2H-benzo[ ][1,4]diazepin-2-one (EP 539170 [1993]) and 3–3,4-dichlorophenyl)-2-phenyl-propionic acid using the procedure of Step 1E shown in Scheme 1.

($^1$H, CDCl$_3$) 0.79–0.93 (4H, m), 1.10–1.50 (3H, m), 2.89–3.31 (5H, m), 2.90–3.53 (4H, m), 3.68 (1H, dd, J=7.4, 6.6 Hz), 5.15 (1H, dd, J=5.5, 2.2 Hz), 6.81–7.55 (12H, m); MS (ES+), MH+=549.

Example 33

(2R)-3-(3,4-Dichlorophenyl)-N-(1-methyl-5-morpholin-4-yl-2-oxo-2,3-dihydro-1H-benzo[e][1,4]diazepin-3-yl)-2-phenyl-propionamide (1:1 mixture of diastereomers).

Prepared from 3-amino-1-methyl-5-morpholin-4-yl-1,3-dihydro-2H-benzo[e][1,4]diazepin-2-one (Synthesis, 1994, 505) and (2R)-3-(3,4-dichlorophenyl)-2-phenyl-propionic acid using the procedure of Step 1E shown in Scheme 1.

($^1$H, CDCl$_3$) 2.91–2.99 (1H, t, J=7.3 Hz), 3.08–3.25 (4H, m), 3.32–3.46 (3H, m), 3.58–3.81 (7H, m), 5.18(1H, d, J=7.8 Hz), 6.85–6.95 (2H, m), 7.15 (1H, d, J=1.9 Hz), 7.19–7.46 (7H, m), 7.48–7.57 (2H, m); MS (ES+), MH+=551.

Example 34

(2S)-3-(3,4-Dichlorophenyl)-N-(1-methyl-5-morpholin-4-yl-2-oxo-2,3-dihydro-1H-benzo[e][1,4]diazepin-3-yl)-2-phenyl-propionamide Prepared from 3-amino-1-methyl-5-morpholinyl-1,3-dihydro-2H-benzo[e][1,4]diazepin-2-one (Synthesis, 1994, 505) and (2S)-3-(3,4-dichlorophenyl)-2-phenyl-propionic acid using the procedure of Step 1E shown in Scheme 1.

($^1$H, d$^6$-DMSO) (1:1 mixture of diastereomers) 8.57 (1H, app t, J=6.5 Hz), 7.72–7.57 (3H, m), 7.44–7.06 (9H, m), 5.14 (1H,app t, J=7.8 Hz), 4.89 (1H, br), 4.37–4.34 (1H, m), 3.77–3.53 (4H, m), 3.42–3.10 (7H, m), 2.91 (1H, dd, J=7.2, 13.8 Hz); MS (CI+), MH+=551.

Example 35

(2R)-3-(3,4-Dichlorophenyl)-N-[1-methyl-2-oxo-5-(4-trifluoromethyl-piperidin-1-yl)-2,3-dihydro-1H-benzo[e][1,4]diazepin-3-yl]-2-phenyl-propionamide Prepared from 3-amino-1-methyl-5-(4-trifluoromethyl-piperidin-1-yl)-1,3-dihydro-2H-benzo[e][1,4]diazepin-2-one (WO94/03437) and (2R)-3-(3,4-dichlorophenyl)-2-phenyl-propionic acid using the procedure of Step 1E shown in Scheme 1

($^1$H, d$^6$-DMSO) (1:1 mixture of diastereomers) 8.66–8.60 (1H, m), 7.74–7.56 (3H, m), 7.46–7.32 (4H, m), 7.27–7.02 (4H, m), 5.15 (1H, app t, J=6.5 Hz), 4.71 (1H, br), 3.78–3.67 (2H, m), 3.34 (3H, s, diast. A), 3.31 (3H, s, diast. B), 3.31–3.10 (4H, m), 2.94 (1H, dd, J=6.5, 12.5 Hz), 2.64–2.62 (1H, m), 1.91–1.68 (3H, m), 1.52–1.46 (1H, m); MS (CI+), MH+=560.

Example 36

(±)-3-(3,4Dichlorophenyl)-N-[1-methyl-2-oxo-5-(4-trifluoromethyl-piperidin-1-yl)-2,3-dihydro-1H-benzo[e][1,4]diazepin-3-yl]-2-phenyl-propionamide (1:1 mixture of diastereomers).

Prepared from 3-amino-1-methyl-5-(4-trifluoromethyl-piperidin-1-yl)-1,3-dihydro-2H-benzotel[1,4]diazepin-2-one (WO94/03437) and (±)-3-(3,4-dichlorophenyl)-2-phenyl-propionic acid using the procedure of Step 1E shown in Scheme 1.

($^1$H, CDCl$_3$) 0.79–0.91 (2H, m), 1.62–1.98 (3H, m), 2.07–2.28 (1H, m), 2.52–2.25 (2H, m), 2.89–3.01(1H, m), 3.30–3.88 (6H, m), 3.86–4.02 (1H, m), 5.15(1H, app t, J=8.1 Hz), 6.82–6.98 (1H, m), 7.15–7.39 (9H, m), 7.46–7.58 (2H,m); MS (ES+), MH+=617.

Example 37

(2S)-3-(3,4-Dichlorophenyl)-2-methyl-N-[1-methyl-2-oxo-5-(4-trifluoromethylpiperidin-1-yl)-2,3-dihydro-1H-benzo[e][1,4]diazepin-3-yl]-propionamide Prepared from 3-amino-1-methyl-5-(4-trifluoromethyl-piperidin-1-yl)-1,3-dihydro-2H-benzo[e][1,4]diazepin-2-one (WO94/03437) and 3-(3,4-dichlorophenyl)-2-methyl-propionic acid using the procedure of Step 1E shown in Scheme 1.

($^1$H, CDCl$_3$) 7.56–7.50 (2H, m), 7.33–7.22 (4H, m), 7.03 (1H, dd, J=2, 8.2 Hz), 6.92 (1H, d, J=7.7 Hz), 5.17 (1H, d, J=7.8 Hz), 4.03–3.99 (1H, m), 3.51–3.71 (1H, m), 3.39 (3H, s), 2.94 (1H, dd, J=6.7, 12.8 Hz), 2.72–2.52 (4H, m), 2.27–2.07 (1H, m), 1.93–1.90 (1H, m), 1.78–1.50 (3H, m), 1.19 (3H, d, J=6.5 Hz); MS (CI+), MH$^+$=555.

Example 38

(2S)-2-(3,4-Dichlorobenzyl)-pent-4-enoic acid [5-(3-aza-bicyclo[3.2.2]non-3-yl)-1-methyl-2-oxo-2,3-dihydro-1H-benzo[e][1,4]diazepin-3-yl]-amide Prepared from 3-amino-5-(3-azabicyclo[3.3.2]non-3-yl)-1-methyl-1,3-dihydro-2H-benzo[e][1,4]diazepin-2-one (WO94/03437) and (2S)-2-(3,4-dichlorobenzyl)-pent-4-enoic acid using the procedure of Step 1E shown in Scheme 1.

($^1$H, CDCl$_3$) (1:1 mixture of diastereomers) 7.52–7.44 (2H, m), 7.32–7.21 (4H, m), 7.07–7.02 (1H, m), 6.87–6.81 (1H, m), 5.86–5.79 (1H, m), 5.19–5.05 (3H, m), 3.56–3.48 (2H, m), 3.37 (3H, s), 3.35–3.45 (2H, m), 2.96–2.87 (1H, m), 2.74–2.67 (1H, m), 2.54–2.41 (2H, m), 2.27–2.20 (1H, m), 2.10–2.03 (2H, m), 2.02–1.79 (2H, m), 1.70–1.62 (6H, m).

Example 39

(±)-N-[5-(3-Azabicyclo[3.2.2]non-3-yl)-1-methyl-2-oxo-2,3-dihydro-1H-benzo[e][1,4]diazepin-3-yl]-3-(3,4-dichlorophenyl)-2-phenyl-propionamide Prepared from 3-amino-5-(3-azabicyclo[3.3.2]non-3-yl)-1-methyl-1,3-dihydro-2H-benzo[e][1,4]diazepin-2-one (WO94/03437) and 3-(3,4-dichlorophenyl)-2-phenyl-propionic acid using the procedure of Step 1E shown in Scheme 1.

($^1$H, CDCl$_3$) (1:1 mixture of diastereomers) 7.51–7.43 (2H, m), 7.33–7.19 (8H, m), 7.03–6.94 (2H, m), 6.85 (1H, d, J=7.7 Hz), 5.16 (1H, 2xd, J=7.7 Hz), 3.89–3.84 (1H, m), 3.57–3.47 (3H, m), 3.35 (3H, s, diast. A), 3.31 (3H, s, diast. B), 3.26–3.23 (2H, m), 3.07 (1H, dd, J=6.9, 13.7), 1.96–1.92 (2H, m), 1.86–1.80 (2H, m), 1.70–1.60 (6H, m); MS (CI+), MH$^+$=589.

Example 40

(±)-3-(3,4-Dichlorophenyl)-N-(1-methyl-2-oxo-5-pyridin-4-yl-2,3-dihydro-1H-benzo[e][1,4]diazepin-3-yl)-2-phenyl-propionamide Prepared from benzyl carbamate C (Scheme 3) by way of Step 3C using 3-(3,4-dichlorophenyl)-2-phenyl-propionic acid followed by Steps 3D and 3E (Scheme 3).

($^1$H, CDCl$_3$) (1:1 mixture of diastereomers) 8.72 (2H, m), 8.64 (2H, m), 7.62 (1+1H, m), 7.33 (13+13H,m), 6.99 (1H, m), 6.94 (1H, m), 5.46 (1H, d, J=8.0 Hz), 5.42 (1H, d, J=8.0 Hz), 3.78 (1+1H, m), 3.52 (1+1H, m), 3.43 (3H, s), 3.40 (3H, s), 3.00 (1+1H, m); MS (ES+), MH$^+$=543.

Example 41

(±)-3-(3,4-Dichlorophenyl)-N-(1,5-diisopropyl-2,4-dioxo-2,3,4,5-tetrahydro-1H-benzo[b][1,4]diazepin-3-yl)-2-phenyl-propionamide Prepared from 3-amino-1,5-diisopropyl-2,4-dioxo-2,3,4,5-tetrahydro-1H-benzo[b][1,4]diazepine (WO96/40655) and 3-(3,4-dichlorophenyl)-2-phenyl-propionic acid using the procedure of Step 1E shown in Scheme 1.

($^1$H, CDCl$_3$) 7.31 (11H, m), 6.88 (1H, dd, J=0.9, 8 Hz), 6.76 (1H, d, J=7.3 Hz), 4.90 (1H, d, J=7.2 Hz), 4.47 (2H, m), 3.73 (1H, dd, J=8.1, 6.8 Hz), 3.45 (1H, dd, J=6.8, 13.9 Hz), 2.97 (1H, dd, J=8.1, 13.9 Hz), 1.49 (3H, d, J=6.9 Hz), 1.47 (3H, d, J=6.9 Hz), 1.26 (3H, d, J=6.9 Hz), 1.20 (3H, d, J=6.9 Hz); MS (ES+), MH$^+$=552.

Example 42

(±)-N-[5-(4-Bromo-phenyl)-2-oxo-2,3-dihydro-1H-benzo[e][1,4]diazepin-3-yl]-3-(3,4-dichloro-phenyl)-2-phenyl-propionamide (1:1 mixture of diastereomers)

Prepared by treating the product from Step 2A (Scheme 2) with HBr/AcOH (c.f Step 2D, Scheme 2) followed by treatment with 3-(3,4-dichlorophenyl)-2-phenyl-propionic acid using the procedure of Step 1E shown in Scheme 1.

($^1$H, CDCl$_3$) 8.85 (1H, s), 8.80 (1H, s), 7.44 (3+3H, m), 7.26 (11+11H, m), 6.98 (3+3H, m), 5.43 (1H, d, J=8.0 Hz), 5.40 (1H, d, J=8.0 Hz), 3.78 (1+1H, m), 3.50 (1+1H, m), 2.98 (1+1H, m); MS (ES+) MH$^+$=607.

Example 43

(±)-N-[5-(4-Bromophenyl)-1-methyl-2-oxo-2,3-dihydro-1H-benzo[e][1,4] diazepin-3-yl]-3-(3,4-dichlorophenyl)-2-phenyl-propionamide (1:1 mixture of diastereomers)

Prepared by treating the product from Step 2B (Scheme 2) with HBr/AcOH (c.f Step 2D, Scheme 2) followed by treatment with 3-(3,4-dichlorophenyl)-2-phenyl-propionic acid using the procedure of Step 1E shown in Scheme 1.

($^1$H, CDCl$_3$) 7.58–7.19 (16+16H, m), 6.96 (1+1H, m), 5.42 (1H, d, J=8.0 Hz), 5.39 (1H, d, J=8.0 Hz), 3.79 (1+1H, m), 3.50 (1+1H, m), 3.44 (3H, s), 3.41 (3H, s), 3.02 (1+1H, m); MS (ES+) MH$^+$=622.

Example 44

(2S)-N-[5-(4-Bromophenyl)-1-methyl-2-oxo-2,3-dihydro-1H-benzo[e][1,4]diazepin-3-yl]-3-(3,4dichlorophenyl)-2-methyl-propionamide Prepared by treating the product from Step 2B (Scheme 2) with HBr/AcOH (c.f Step 2D, Scheme 2) followed by treatment with (2S)-3-(3,4-dichlorophenyl)-2-methyl-propionic acid using the procedure of Step 1E shown in Scheme 1.

Less polar diastereomer ($^1$H, CDCl$_3$) 7.62–7.26 (11H, m), 7.05 (1H, d, J=7.2 Hz), 5.40 (1H, d, J=7.8 Hz), 3.45 (3H, s), 2.97 (1H, m), 2.68 (2H, m), 1.27 (3H, d, J=6.0 Hz); MS (ES+) MH$^+$=557. More polar diastereomer ($^1$H, d$_6$-DMSO) 9.12 (1H, d, J=8.2 Hz), 7.75–7.20 (11H, m), 5.24 (1H, d, J=8.2 Hz), 3.37 (3H, s), 2.97 (1H, m), 2.84 (1H, dd, J=8.3, 13.2 Hz), 2.59 (1H, dd, J=6.5, 13.4 Hz); MS (ES+) MH$^+$=557.

Example 45

(2S)-2-(3,4-Dichlorobenzyl)-pent-4-enoic acid [5-(4-bromophenyl)-1-methyl-2-oxo-2,3-dihydro-1H-benzo[e][1,4]diazepin-3-yl]-amide Prepared by treating the product from Step 2B (Scheme 2) with HBr/AcOH (c.f Step 2D, Scheme 2) followed by treatment with (2S)-3-(3,4dichlorophenyl)-pent-4-enoic acid using the procedure of Step 1E shown in Scheme 1.

($^1$H, CDCl$_3$) (1:1 mixture of diastereomers) 7.58–7.03 (12H, m), 5.90–5.82 (1H, m), 5.40 (1H, dd, J=8, 2 Hz), 5.16–5.08 (2H, m), 3.43 (3H, s), 3.01–2.88 (1H, m), 2.79–2.74 (1H, m), 2.62–2.49 (2H, m), 2.47–2.28. (1H, m); MS (CI+), MH$^+$=586.

Example 46

(2S)-2-(3,4Dichlorobenzyl)-pent4enoic acid [5-(2-fluorophenyl)-1-isopropyl-2-oxo-2,3-dihydro-1H-benzo[e][1,4]diazepin-3-yl]-amide (1:1 mixture of diastereomers)

Prepared from 3-amino-5-(2-fluoro-phenyl)-1-isopropyl-2-oxo-1,3-dihydro-2H-benzo[e][1,4]diazepine [available in an analogous fashion to (S)-3amino-1-methyl-5-phenyl-1,3-dihydro-2H-benzo[e][1,4]diazepin-2-one (i.e. *J. Org. Chem.* 1987, 52, 3232)] and (2S)-2-(3,4dichlorobenzyl)-pent-4-enoic acid using the procedure of Step 1E shown in Scheme 1.

($^1$H, CDCl$_3$) 7.72–6.98 (12+12H, m), 5.87 (1+1H, m), 5.42 (1H, d, J=8.2 Hz), 5.37 (1H, d, J=8.2 Hz), 5.13 (2+2H, m), 4.53 (1+1H, m), 2.94 (1+1H, m), 2.76 (1+1H, m), 2.63–2.45 (2+2H, m), 2.28 (1+1H, m), 1.50 (3+3 (coincident), d, J=6.8 Hz), 1.27 (3H, d, J=6.8 Hz), 1.26 (3H, d, J=6.9 Hz); MS (ES+) MH$^+$=552.

Example 47

2-(3,4-Dichlorobenzyl)-pent4-enoic acid [(S)-5-(2-fluorophenyl)-2-oxo-1-(2,2,2-trifluoroethyl)-2,3-dihydro-1H-benzo[e][1,4]diazepin-3-yl]-amide (1:1 mixture of diastereomers)

Prepared from 3-amino-5-(2-fluoro-phenyl)-1-(2,2,2-trifluoroethyl)-2-oxo-1,3-dihydro-2H-benzo[e][1,4]diazepine [available in an analogous fashion to (S)-3-amino-1-methyl-5-phenyl-1,3dihydro-2H-benzole][1,4]diazepin-2-one (i.e. *J. Org. Chem.* 1987, 52, 3232)] and (2S)-2-(3,4-dichlorobenzyl)-pent-4-enoic acid using the procedure of Step 1E shown in Scheme 1.

($^1$H, CDCl$_3$) 7.58–7.02 (12+12H, m), 5.84 (1+1H, m), 5.57 (1H, d, J=8.2 Hz), 5.52 (1H, d, J=8.2 Hz), 5.15 (3+3H, m), 4.23 (1+1H, m), 2.93 (1+1H, m), 2.75 (1+1H, m), 2.60 (1+1H, m), 2.50 (1+1H, m), 2.30 (1+1H, m); MS (ES+), MH$^+$=592.

Example 48

(2R)-3-(3,4-Dichlorophenyl)-N-[5-(2-fluorophenyl)-2-oxo-1-(2,2,2-trifluoroethyl)-2,3-dihydro-1H-benzo[e][1,4]diazepin-3-yl]-2-phenyl-propionamide (1:1 mixture of diastereomers)

Prepared from 3-amino5-(2-fluoro-phenyl)-1-(2,2,2-trifluoroethyl)-2-oxo-1,3-dihydro-2H-benzo[e][1,4]diazepine [available as above] and 3-(3,4-dichlorophenyl)-2-phenyl-propionic acid using the procedure of Step 1E shown in Scheme 1.

($^1$H, CDCl$_3$) 7.43–6.93 (17+17H, m), 5.55 (1H, d, J=8.0 Hz), 5.53 (1H, d, J=8.0 Hz), 5.12 (1+1H, m), 4.13 (1+1H, m), 3.48 (2+2H, m), 2.99 (1+1H, m); MS (ES+) MH$^+$=628.

Example 49

3-(3,4-Dichlorophenyl)-2-methyl-N-(6,7dihydro-7-methyl-6-oxo-3-methyl-5H-1,2,4-triazolo[4,3-d][1,4]benzodiazepin-5-yl)-propionamide Prepared by reaction of the product of Step 3D (Scheme 3) with acetic acid hydrazide using the procedure from Step 3G.

($^1$H, DMSO-d$_6$) 8.94 (brs, 1H), 7.85–7.37 (m, 6H), 7.16 (d, J=8.0 Hz, 1H), 6.07 (d, J=7.8 Hz, 1H), 3.33 (3H, s), 3.05–2.45 (m, 3H), 2.32 (s, 3H), 1.01 (d, J=6.6 Hz, 3H).

Example 50

3-(3,4-Dichlorophenyl)2-methyl-N-(6,7-dihydro-7-methyl-6-oxo-5H-1,2,4-triazolo[4,3-d][1,4]benzodiazepin-5-yl)-propionamide (1:1 mixture of diastereomers)

Prepared by reaction of the product of Step 3D (Scheme 3) with formic acid hydrazide using the procedure from Step 3G.

($^1$H, DMSO-d$_6$) 9.4 (0.5H, s), 9.35 (s, 0.5H), 8.15 (s, 0.5H), 8.10 (s, 0.5H), 7.9–7.2 (m, 7H), 6.2–6.1 (m, 1H), 3.36 (s, 1.5H), 3.34 (s, 1.5H), 3.2–3.5 (m, 3H), 0.9 (m, 3H).

Example 51

3-(3,4-Dichlorophenyl)-2-methyl-N-(6,7dihydro-7-methyl-6-oxo-3-pyridin-3-yl-5H-1,2,4-triazolo[4,3-d][1,4]benzodiazepin-5-yl)-propionamide (1:1 mixture of diastereomers)

Prepared by reaction of the product of Step 3D (Scheme 3) with nicotinic acid hydrazide using the procedure from Step 3G.

($^1$H, DMSO-d$_6$) 9.6 (s, 0.5H), 9.5 (s, 0.5H), 9.22 (s, 0.5H), 9.21 (s, 0.5H), 8.7–7.2 (m, 10H), 6.3–6.1 (m, 1H), 3.38 (s, 1.5H), 3.37 (s, 1.5H), 3.3–2.6 (m, 3H), 0.9 (m, 3H).

Example 52

(2S)-3-(3,4-Difluorophenyl)-2-methyl-N-(7-methyl-6-oxo-6,7-dihydro-5H-[1,2,4]triazolo[4,3-d][1,4]benzodiazepin-5-yl)propanamide Prepared from C (Scheme 3) via Step 3C (with (2$)-3-(3,4-difuorophenyl)-2-methyl propionic acid), Step 3D and Step 3G (with formic acid hydrazide).

Two diastereomers ($^1$H NMR, 400 MHz, DMSO) 9.5–9.2 (1H, m), 8.15 (0.5H, s), 8.10 (0.5H, s), 7.90–6.6 (7H, m), 6.25–6.1 (1H, m), 3.36 (1.5H, s), 3.34 (1.5H, s), 2.85–2.75 (1H, m), 2.6–2.5 (2H, m), 1.1–0.9 (3H, m). m/z: Found 412 (MH$^+$), C$_{21}$H$_{19}$N$_5$O$_2$F$_2$+H$^+$ requires 412.

Example 53

(±)-3-(3,4-Dichlorophenyl)-2-phenyl-N-(5-phenyl-2-thioxo-2,3-dihydro-1H-benzo[e][1,4]diazepin-3-yl)propionamide (1:1 mixture of diastereomers)

Prepared by reaction of 3-amino-5-phenyl-1,3-dihydro-2H-benzo[e][1,4]diazepin-2-one (*J. Org. Chem.* 1987, 52, 3232) with Lawesson's reagent (as WO95/14693) followed by removal of the protecting group as in Step 2D (Scheme 2) and reaction with 3-(3,4-dichlorophenyl)-2-phenyl-propionic acid using the procedure of Step 1E shown in Scheme 1.

($^1$H, CDCl$_3$) 9.97 (1H, s), 9.74 (1H, s), 7.75 (1H, d, J=7.9 Hz), 7.55 (1H, d, J=7.9 Hz), 7.45–6.95 (17+17H, m), 5.68 (1H, d, J=8.2 Hz), 5.61 (1H, d, J=8.2 Hz), 3.80 (1+1H, m), 3.53 (1+1H, m), 3.03 (1+1H, m); MS (ES+) MH$^+$=544.

Example 54

(±)-3-(3,4-Dichlorophenyl)-2-phenyl-N-(6-phenyl-2,4dihydro-1H-3,5,10b-triaza-benzo[e]azulen-4-yl)-propionamide Prepared from (±)-3-(3,4-dichlorophenyl)-2-phenyl-N-(5-phenyl-2-thioxo-2,3-dihydro-1H-benzo[e][1,4]diazepin-3-yl)-propionamide by the method of WO95/14693.

Less polar diastereomer ($^1$H, CDCl$_3$) 7.33 (15H, m), 7.00 (3H, m), 5.68 (1H, d, J=7.3 Hz), 4.03 (1H, m), 3.90 (1H, m), 3.69 (3H, m), 3.54 (1H, dd, J=8.2, 13.7 Hz), 3.00 (1H, dd, J=8.1, 13.7 Hz); MS (ES+) MH$^+$=553. More polar diastereomer ($^1$H, CDCl$_3$) 7.33 (15H, m), 7.00 (3H, m), 5.75 (1H, d, J=7.3 Hz), 4.08 (1H, m), 3.94 (1H, m), 3.74 (3H, m), 3.45 (1H, dd, J=8.1, 13.7 Hz), 2.98 (1H, dd, J=8.1, 13.7 Hz); MS (ES+) MH$^+$=553.

Example 55

(±)-3-(3,4-Dichlorophenyl)-2-phenyl-N-(6-phenyl4H-3,5,10b-triaza-benzo[e]azulen-4-yl)-propionamide Prepared from (±)-3-(3,4-dichlorophenyl)-2-phenyl-N-(5-phenyl-2-thioxo-2,3dihydro-1H-benzo[e][1,4]diazepin-3-yl)-propionamide by the method of WO95/14693.

Less polar diastereomer ($^1$H, CDCl$_3$) 7.71 (1H, d, J=7.9 Hz), 7.62 (1H, m), 7.46–7.22 (16H, m), 7.04 (2H, m), 5.93 (1H, d, J=7.8 Hz), 3.82 (1H, dd, J=7.4, 7.4), 3.58 (1H, dd, J=8.2, 13.7 Hz), 3.03 (1H, dd, J=6.8, 13.7 Hz); MS (ES+) MH$^+$=551. More polar diastereomer ($^1$H, CDCl$_3$) 7.61 (1H, m), 7.53–7.21 (17H, m), 7.05 (1H, m), 6.95 (1H, dd, J=2.0, 8.2 Hz), 6.01 (1H, d, J=8.4 Hz), 3.87 (1H, t, J=7.5 Hz), 3.48 (1H, m), 3.01 (1H, dd, J=7.2, 13.9 Hz); MS (ES+) MH$^+$=551.

Example 56

(±)-N-[5-(2-methoxy-4-pyridinyl)-2-oxo-2,3-dihydro-1H-1,4-benzodiazepin-3-yl]-2-methyl-3-phenylpropanamide Prepared from 3-amino-5-(2-methoxypyridin-4-yl)-2-oxo-2,3-dihydro-1H-benzo[e][1,4]diazepine (WO93/07131) and 2-methyl-3-phenyl-propionic acid using the procedure of Step 1E shown in Scheme 1.

$^1$H NMR (CDCl$_3$) (1:1 mixture of diastereomers) 1.19–1.27 (3H, m), 2.69–2.76 (2H, m), 3.06–3.13 (1H, m), 3.95 (1.5H, s), 3.96 (1.5H, s), 5.53–5.57 (1H, m), 6.81 (1H, m), 7.00–7.36 (10H, m), 7.52–7.58 (1H, m), 8.19 (0.5H, s), 8.20 (0.5H, s), 8.34 (1H, v br s).

Example 57

(2S)-3-(3,4Dichlorophenyl)-N-[5-(2-methoxypyridin-4-yl)-2-oxo-2,3-dihydro-1H-benzo[e][1,4]diazepin-3-yl]-2-methyl-propionamide Prepared from 3-amino-5-(2-methoxypyridin4yl)-2-oxo-2,3dihydro-1H-benzo[e][1,4]diazepine (WO93/07131) and (2S)-3-(3,4-dichlorophenyl)-2-methyl-propionic acid using the procedure of Step 1E shown in Scheme 1.

$^1$H NMR (CDCl$_3$) (1:1 mixture of diastereomers) 1.23–1.30 (3H, m), 2.65–2.72 (2H, m), 2.96–3.08 (1H, m), 3.95 (3H, s), 5.49–5.54 (1H, m), 6.77–6.81 (1H, m), 7.01–7.40 (8H, m), 7.53–7.59 (1H, m), 8.19–8.24 (1H, m). MS (ES+) MH$^+$=497.

Example 58

(±)-N-[5-(Bicyclo[2.2.1]hept-1-yl)-1-methyl-2-oxo-2,3-dihydro-1-H-benzo[e][1,4]diazepin-3-yl]-3-(3,4-dichlorophenyl)-2-phenyl-propionamide Prepared from 3-amino-5-(bicyclo[2.2.1]hept-1-yl)-1-methyl-2-oxo-2,3-dihydro-1H-benzo[e][1,4]diazepine and (±)-3-(3,4-dichlorophenyl)-2-phenyl-propionic acid using the procedure of Step 1E shown in Scheme 1.

($^1$H, CDCl$_3$) (1:1 mixture of diastereomers) 7.62–7.56 (1H, m), 7.46–7.42 (1H, m), 7.30–7.11 (10H, m), 6.96–6.90 (1H, m), 5.29–5.25 (1H, m), 3.72–3.68 (1H, m), 3.50–3.52 (3H, m), 2.99–2.91 (1H, m), 2.28–2.24 (1H, m), 1.74–1.23 (11H, m); MS (CI+), MH$^+$=560.

Example 59

3-(3,4-Dichlorophenyl)-2-methyl-N-(1-methyl-2-oxo-5-pyridin-3-yl-2,3-dihydro-1H-benzo[e][1,4]diazepin-3-yl)-propionamide Prepared by reaction of the product from Step 3D (Scheme 3) with diethyl-3-pyridylborane using the procedure of Step 3E shown in Scheme 3.

$^1$H NMR (CDCl$_3$) (1:1 mixture of diastereomers) 1.24–1.30 (3H, m), 2.64–2.72 (2H, m), 2.97–3.06 (1H, m), 3.47 (3H, s), 5.43 (0.5H, d, J=7.8 Hz), 5.49 (0.5H, d, J=8.0 Hz), 7.04–7.11 (1H, m), 7.23–7.44 (711, m), 7.60–7.66 (1H, m), 7.99–8.10 (1H, m), 8.67–8.72 (2H, m).

Example 60

3-(3,4-Dichlorophenyl)-2-methyl-N-(1-methyl-2-oxo-5-pyridin-4-yl-2,3-dihydro-1H-benzo[e][1,4]diazepin-3-yl)-propionamide Prepared by reaction of the product from Step 3D (Scheme 3) with pyridine-4-boronic acid using the procedure of Step 3E shown in Scheme 3.

$^1$H NMR (CDCl$_3$) (1:1 mixture of diastereomers) 1.24–1.30 (3H, m), 2.65–2.72 (2H, m), 2.97–3.06 (1H, m), 3.46 (3H, s), 5.445.51 (1H, m), 7.04–7.11 (1H, m), 7.22–7.49 (8H, m), 7.61–7.67 (1H, m), 8.68 (2H, m).

Example 61

3-(3,4-Dichlorophenyl)-N-[5-(4-fluorophenyl)-1-methyl-2-oxo-2,3-dihydro-1H-benzo[e][1,4]diazepin-3-yl]-2-methyl-propionamide Prepared by reaction of the product from Step 3D (Scheme 3) with 4-fluorophenylboronic acid using the procedure of Step 3E shown in Scheme 3.

$^1$H NMR (CDCl$_3$) (1:1 mixture of diastereomers) 1.23–1.29 (3H, m), 2.65–2.69 (2H, m), 2.97 (1H, m), 3.45 (3H, s), 5.40 (1H, m), 7.04–7.11 (3H, m), 7.23–7.27 (3H, m), 7.32–7.40 (3H, m), 7.51–7.75 (3H, m); MS (ES+) MH$^+$=498.

Example 62

3-(3,4-Dichlorophenyl)-N-[5-(6-methoxypyridin-3-yl)-1-methyl-2oxo-2,3-dihydro-1H-benzo[e][1,4]diazepin-3-yl]-2-methyl-propionamide Prepared by reaction of the product from Step 3D (Scheme 3) with 2-methoxypyridine-5-boronic acid using the procedure of Step SE shown in Scheme 3.

Less polar diastereomer $^1$H NMR (CDCl$_3$) 1.27 (3H, d, J=6.3 Hz), 2.63–2.70 (2H, m), 2.95–2.99 (1H, m), 3.45 (3H, s), 3.97 (3H, s), 5.40 (1H, d, J=7.9 Hz), 6.77 (1H, d, J=8.7 Hz), 7.04–7.06 (1H, m), 7.20–7.41 (6H, m), 7.59–7.63 (1H, m), 7.98 (1H, dd, J=8.7, 2.5 Hz), 8.22 (1H, d, J=2.5 Hz). More polar diastereomer $^1$H NMR (CDCl$_3$) 1.23–1.26 (3H, m), 2.64–2.70 (2H, m), 3.02–3.08 (1H, m), 3.45 (3H, s), 3.97 (3H, s), 5.45 (1H, d, J=8.0 Hz), 6.81 (1H, d, J=8.7 Hz), 7.08–7.11 (1H, m), 7.19–7.44 (6H, m), 7.58–7.62 (1H, m), 7.95 (1H, dd, J=8.6, 2.4 Hz), 8.17 (1H, d, J=2.4 Hz).

Example 63

3-(3,4-Dichlorophenyl)-2-methyl-N-[-1-methyl-2-oxo-5-(1-oxo-2,3-dihydro-1H-isoindol-5-yl)-2,3-dihydro-1H-benzo[e][1,4]diazepin-3-yl]-propionamide Prepared by reaction of the product from Step 3D (Scheme 3) with 2-(1-oxo-2,3-dihydro-1H-isoindol-5-yl)4,4,5,5-tetramethyl-1,3,2-dioxa-borolane using the procedure of Step 3E shown in Scheme 3.

$^1$H NMR (CDCl$_3$) (1:1 mixture of diastereomers) 1.19–1.30 (3H, m), 2.65–2.72 (2H, m), 2.90–3.00 (1H, m), 3.47–3.49 (3H, m), 4.48–4.51 (2H, m), 5.40–5.5 (1H, m), 6.23 (1H, br s), 6.95–7.12 (1H, m), 7.25–7.90 (10H, m); MS (ES+) MH$^+$=535.

Example 64

(2S)-3-(3,4-Difluorophenyl)-2-methyl-N-[1-methyl-2-oxo-5-(1-oxo-1,2,3,4-tetrahydro-6-isoquinolinyl)-2,3-dihydro-1H-benzo[e][1,4]diazepin-3-yl]propanamide Prepared from C (Scheme 3) via Step 3C (with (2S)-3-(3,4-difluorophenyl)-2-methyl propionic acid), Step 3D and Step 3E (with 2-(1-oxo-1,2,3,4-tetrahydro-6-isoquinolinyl)-4,4,5,5-tetramethyl-1,3,2-dioxa-borolane).

($^1$H NMR, 400 MHz, DMSO, 1:1 mixture of diastereomers) 9.18 (0.5H, d, J=8.1), 9.12 (0.5H, d, J=8.1), 8.04 (1H, s), 7.95–7.06 (9H, m), 7.07–7.04 (1H, m), 5.29 (0.5H, d, J=8.1), 5.27 (0.5H, d, J=8.1), 3.35 (3H, s), 3.2–2.5 (7H, m), 1.03 (1.5H, d, J=6.4), 0.98 (1.5H, d, J=6.4). m/z: Found 517 (MH$^+$), C$_{29}$H$_{26}$N$_4$O$_3$F$_2$+H$^+$ requires 517.

Example 65

(2S)-N-{5-[4-(Aminosulfonyl)phenyl]-1-methyl-2-oxo-2,3-dihydro-1H-benzo[e][1,4]diazepin-3-yl}-3-(3,4dichlorophenyl)-2-methylpropanamide Prepared by reaction of the product from Step 3D (Scheme 3) with 2-(4-(aminosulfonyl)phenyl)-4,4,5,5-tetramethyl-1,3,2-dioxa-borolane using the procedure of Step 3E shown in Scheme 3.

Less polar diastereomer. m/z: Found 559 (MH$^+$), C$_{26}$H$_{24}$N$_4$O$_4$Cl$_2$S+H$^+$ requires 559. More polar diastereomer. m/z: Found 559 (MH$^+$), C$_{26}$H$_{24}$N$_4$O$_4$Cl$_2$S+H$^+$ requires 559.

Example 66

(2S)-3-(3,4-Dichlorophenyl)-2-methyl-N-[1-methyl-2-oxo-5-(1H-pyrazol-3-yl)-3-yl)-2,3-dihydro-1H-benzo[e][1,4]diazepin-3yl]propanamide Prepared by reaction of the product from Step 3D (Scheme 3) with 1H-pyrazol-3-yl boronic acid using the procedure of Step 3E shown in Scheme 3.

(1H NMR, 360 MHz, DMSO) 13.2 (1H, s), 9.10 (0.5 H, d, J=8.2), 9.06 (0.5 H, d, J=8.2), 7.83–7.19 (8H, m), 6.7 (0.5H, brs), 6.6 (0.5H, brs), 5.31 (0.5H, d, J=8.1), 5.28 (0.5H, d, J=8.1), 3.39 (3H, s), 2.96–2.88 (2H, m), 2.57–2.49 (1H, m), 1.01 (1.5 H, d, J=6.4), 0.96 (1.5H, d, J=6.4) m/z: Found 470 (MH$^+$), C$_{23}$H$_{21}$N$_5$O$_2$Cl$_2$+H$^+$ requires 470.

Example 67

(2R)-3-(3,4-Dichlorophenyl)-N-[5-(1,4dioxa-8-azaspiro[4,5]dec-8-yl)-1-methyl-2-oco-2,3-dihydro-1H-benzo[e][1,4]diazepin-3-yl]-2-(3-thienyl)propanamide Prepared from C (Scheme 3) via Step 3C (using (2R)-3-(3,4-dichlorophenyl)-2-(3-thienyl)propanoic acid), Step 3D and Step 3F (with 1,4dioxa-8-azaspiro[4.5]decane).

($^1$H,CDCl$_3$) 7.54–7.47 (2H,m), 7.27–6.89 (9H,m), 5.17 (1H, d, 7.7), 3.95 (2H,s), 3.94 (2H,s), 3.82 (1H, dd, J=6.3, 7.3), 3.44–3.20 (8H,m),2.96 (1H, dt, J=7.7,14.9), 1.83–1.74 (2H, m), 1.56–1.45 (2H, m) ; MS (CI+) MH+613.

Example 68

(2R)-3-(3,4-Dichlorophenyl)-2-(4fluorophenyl)-N-((3S)-1-methyl-2oxo-5-phenxy-2,3-dihydro-1H-benzo[e][1,4]diazepin-3-yl)-propanamide Prepared from (S)-3-amino-1-methyl-5-phenyl-1,3-dihydro-2H-benzo[e][1,4]diazepin-2-one (J. Org. Chem. 1987, 52, 955 and 3232) (designated B) and (2R)-3-(3,4-dichlorophenyl)-2-(4-fluorophenyl)-propionic acid using the procedure of Step 1E shown in Scheme 1.

($^1$H, CDCl$_3$) 7.61–7.18 (14H, m), 7.04 (2H, t, J=8.5 Hz), 6.91 (1H, d, J=8 Hz), 5.53 (1H, d, J=8 Hz), 3.75 (1H, t, J=7.5 Hz), 3.43 (3H, s), 3.39 (1H, m) and 2.98 (1H, dd, J=14,7.5 Hz); MS (ES+) MH$^+$=560.

Example 69

(2R)-3-(3,4-Dichlorophenyl)-2-(4-bromophenyl)-N-((3S)-1-methyl-2-oxo-5-phenyl-2,3-dihydro-1H-benzo[e][1,4]diazepin-3-yl)-propanamide Prepared from amine B and (2R)-3-(3,4-dichlorophenyl)-2-(4-bromophenyl)-propionic acid using the procedure of Step 1E shown in Scheme 1.

($^1$H, CDCl$_3$) 7.57–7.18 (16H, m), 6.91 (1H, d, J=8 Hz), 5.43 (1H, d, J=8 Hz), 3.73 (1H, t, J=7.5 Hz), 3.44 (3H, s), 3.39 (1H, m) and 2.97 (1H, dd, J=14,7.5 Hz); MS (ES+) MH$^+$=622.

Example 70

(2S,3S)-3-(3,4-Dichlorophenyl)-3-hydroxy-2-methyl-N-((3S)-1-methyl-2-oxo-5-phenyl-2,3-dihydro-1H-benzo[e][1,4]diazepin-3-yl)-propanamide Prepared from amine B and (2S, 3S)-3-(3,4dichlorophenyl)-3-hydroxy-2-methyl-propionic acid using the procedure of Step 1E shown in Scheme 1.

(¹H, CDCl₃) 7.55–7.30 (12H, m), 7.28–7.20 (1H, m), 5.51 (1H, d, J=8 Hz), 5.11 (1H, br s), 4.40 (1H, br s), 3.49 (3H, s), 2.73–2.71 (1H, m), 1.16 (3H, d, J=7 Hz); MS (ES+) MH⁺=496.

Example 71

(2R)-3-(3,4-Dichlorophenyl)-N-((3S)-1-methyl-2-oxo-5-phenyl-2,3-dihydro-1H-benzo[e][1,4]diazepin-3-yl)-2-pyrrolidin-1-yl-propionamide Prepared from amine B and (2R)-3-(3,4-dichlorophenyl)-2-pyrrolidin-1-yl-propionic acid using the procedure of Step 1E shown in Scheme 1.

(¹H, CDCl₃) 8.32 (1H, d, J=8.5 Hz), 7.61–7.54 (3H, m), 7.48–7.30 (7H, m), 7.24–7.11 (2H, m), 5.48–5.46 (1H, m), 3.46 (3H, s), 3.45–3.41 (1H, m), 3.11 (1H, dd, J=13.5, 8 Hz), 2.97 (1H, dd, 13.5, 5 Hz), 2.80–2.71 (4H, br m), 1.89–1.81 (4H, br m); MS (ES+) MH⁺=535.

Example 72

(2R, 3R)-3-(3,4-Dichlorophenyl)-3-hydroxy-2-methyl-N-((3S)-1-methyl-2oxo-5-phenyl-2,3-dihydro-1H-benzo[e][1,4]diazepin-3-yl)-propionamide Prepared from amine B and (2R, 3R)-3-(3,4-dichlorophenyl)-3-hydroxy-2methyl-propionic acid using the procedure of Step 1E shown in Scheme 1.

(¹H, CDCl₃) 7.64–7.37 (12H, m), 7.29–7.22, (1H, m), 5.51 (1H, d, J=8 Hz), 5.21 (1H, br s), 4.52 (1H, br s), 3.48 (3H, s), 2.73–2.71 (1H, m), 1.11 (3H, d, J=7 Hz); MS (ES+) MH⁺=496.

Example 73

(2S)-3-(3,4-Dichlorophenyl)-N-((3R)-1-methyl-2-oxo-5-phenyl-2,3-dihydro-1H-benzo[e][1,4]diazepin-3-yl)-2-phenyl-propionamide Prepared from (R)-3-amino-1-methyl-5-phenyl-1,3-dihydro-2H-benzo[e][1,4]diazepin-2-one (J. Org. Chem. 1987, 52, 3232) and (2S)-3-(3,4-dichlorophenyl)-2-phenyl-propionic acid using the procedure of Step 1E shown in Scheme 1.

(¹H, CDCl₃) 7.60–7.18 (17H, m), 6.92 (1H, d, J=10 Hz), 5.44 (1H, d, J=8 Hz), 3.78 (1H, t, J=7.5 Hz), 3.50–3.44 (1H, m), 3.42 (3H, s), 3.01 (1H, dd, J=14, 7.5 Hz); MS (ES+) MH⁺=542.

Example 74

3-(2,4-Dichlorophenyl)-2-methyl-N-(3S)-(1-methyl-2-oxo-5-phenyl-2,3-dihydro-1H-benzo[e][1,4]diazepin-3-yl)-propionamide Prepared from amine B and 3-(2,4-dichlorophenyl)-2-methyl-propionic acid using the procedure of Step 1E shown in Scheme 1.

Less polar diastereomer (¹H, CDCl₃) 1.27 (3H, m), 2.83 (2H, m), 3.12 (1H, dd, J=9.8 and 16.2 Hz), 3.46 (3H, s), 5.44 (1H, d, J=7.9), 7.13 (2H, m), 7.28 (2H, m), 7.34–7.40 (5H, m), 7.46 (1H, m), 7.59 (3H, m). MS(ES+): MH⁺=480 More polar diastereomer (¹H, CDCl₃) 1.26 (3H, m), 2.84 (2H, m), 3.13 (1H, dd, J=7.7 and 13.2 Hz), 3.45 (3H, s), 5.49 (1H, d, J=8.2), 7.22 (3H, m), 7.41 (3H, m), 7.45 (3H, m), 7.49 (3H, m), 7.56 (3H, m). MS(ES+): MH⁺=480

Example 75

3-(3,4-Dichlorophenyl)-N-((3S)-1-methyl-2-oxo-5-phenyl-2,3-dihydro-1H-benzo[e][1,4]diazepin-3-yl)-2-thiophen-3-yl-propionamide (1:1 mixture of diastereomers)

Prepared from amine B and 3-(3,4-dichlorophenyl)-2-thiophen-3-yl-propionic acid using the procedure of Step 1E shown in Scheme 1.

(¹H, CDCl₃) 3.04 (1H, m), 3.41 (1H, m), 3.42 and 3.44 (3H, 2×s, diasts.), 3.92 (1H, dd, J=7.5 Hz), 5.45 (1H, d, J=7.9 Hz), 6.96 (1H, m), 7.12 (1H, m), 6.99–7.56 (11H, m), 7.59 (3H, m).

Example 76

3-(3,4-Dichlorophenyl)-N-((3S)-1-methyl-2-oxo-5-phenyl-2,3-dihydro-1H-benzo[e][1,4]diazepin-3-yl)-2-(2-methyl-thiazol-4-yl)-propionamide (1:1 mixture of diastereomers)

Prepared from amine B and 3-(3,4-dichlorophenyl)-2-(2-methyl-thiazol-4-yl)-propionic acid using the procedure of Step 1E shown in Scheme 1.

(¹H, CDCl₃) 2.76 and 2.78 (3H, 2×s, diasts.), 3.25 (1H, m), 3.42 (1H, m), 3.43 and 3.45 (3H, 2×s, diasts.), 3.95 (1H, m), 5.48 (1H, d, J=7.5 Hz), 6.89 (1H, d, J=10.2 Hz), 6.98 (1H, m), 7.21–7.29 (3H, m), 7.36 (4H, m), 7.45 (1H, m), 7.57 (3H, m), 8.18 and 8.29 (1H, 2×m, diasts.); MS(ES+): MH⁺=563

Example 77

3-(3,4-Dichlorophenyl)-N-((3S)-1-methyl-2-oxo-5-phenyl-2,3-dihydro-1H-benzo[e][1,4]diazepin-3-yl)-2-pyridin-4-yl-propionamide Prepared from amine B and 3-(3,4dichlorophenyl)-2-pyridin-4-yl-propionic acid using the procedure of Step 1E shown in Scheme 1.

Less polar diastereomer (¹H, CDCl₃): 3.00 (1H, dd, J=7.1 and 13.8), 3.41 (1H, m), 3.45 (3H, s), 3.75 (1H, m), 5.43 (1H, d, J=7.9 Hz), 6.94 (1H, dd, J=2.0 and 8.2 Hz), 7.21–7.58 (13H, m), 7.60 (1H, m), 8.60 (2H, d, J=6.0 Hz); MS(ES+): MH⁺=543 More polar diastereomer (¹H, CDCl₃): 2.98 (1H, dd, J=6.7 and 13.8 Hz), 3.41 (3H, s), 3.52 (1H, dd, J=8.3 and 13.8 Hz), 3.74 (1H, m), 5.40 (1H, d, J=7.8 Hz), 7.01 (1H, dd, J=2.0 and 8.2 Hz), 7.22–7.47 (10H, m), 7.48 (1H, m), 7.57 (3H, m), 8.54 (2H, d, J=1.6 Hz); MS(ES+): MH⁺=543

Example 78

2–3,4-Dichlorobenzyl)-3-methyl-N-((3S)-1-methyl-2-oxo-5-phenyl-2,3-dihydro-1H-benzo[e][1,4]diazepin-3-yl)-butyramide Prepared from amine B and 2-(3,4 dichlorobenzyl)-3-methyl-butyric acid using the procedure of Step 1E shown in Scheme 1.

Less polar diastereomer (¹H, CDCl₃) 1.14 (6H, m), 2.05 (1H, m), 2.29 (1H, m), 2.84 (2H, m), 3.43 (3H, s), 5.35 (1H, d, J=7.9 Hz), 7.04 (1H, dd, J=2.0 and 8.2 Hz), 7.11 (1H, d, J=7.9 Hz), 7.23 (2H, m), 7.30–7.39 (5H, m), 7.44 (1H, m), 7.58 (3H, m); MS(ES+): MH⁺=508 More polar diastereomer (¹H, CDCl₃) 1.05 (3H, d, J=6.7 Hz), 1.09 (3H, d, J=6.7 Hz), 1.99 (1H, m), 2.29 (1H, m), 2.83 (1H, m), 2.95 (1H, m), 3.43 (3H, s), 5.45 (1H, d, J=8.2 Hz), 7.05 (1H, d, J=8.3 Hz), 7.12

Example 79

3-(3,4-Dichlorophenyl)-N-((3S)-1-methyl-2-oxo-5-phenyl-2,3-dihydro-1H-benzo[e][1,4]diazepin-3-yl-propionamide (1:1 mixture of diastereomers)

Prepared from amine B and 3-(3,4-dichlorophenyl)-2-thiophen-2-yl-propionic acid using the procedure of Step 1E shown in Scheme 1.

($^1$H, CDCl$_3$): 3.06 (1H, m), 3.42 and 3.43 (3H, 2×s, diasts.), 3.51 (1H, m), 4.09 (1H, dd), 5.42 (1H, d), 6.97 (3H, m), 7.21–7.42 (10H, m), 7.54 (3H, m).

Example 80

(2R)-3-(3,4-Dichlorophenyl)-N-((3S)-1-methyl-2-oxo-5-phenyl-2,3-dihydro-1H-benzo[e][1,4]diazepin-3-yl)-2-thiophen-3-yl-propionamide Prepared from amine B and (2R)-3-(3,4-dichlorophenyl)-2-thiophen-3-yl-propionic acid using the procedure of Step 1E shown in Scheme 1.

($^1$H, CDCl$_3$) 3.18 (1H, m), 3.35 (1H, m), 3.44 (3H, s), 3.92 (1H, m), 5.45 (1H, d, J=7.9 Hz), 6.97 (1H, m), 7.13 (1H, m), 7.26 (3H, m), 7.33–7.39 (8H, m), 7.52 (3H, m); MS(ES+): MH$^+$=548

Example 81

2-(3,4-Dichloro-phenoxy)-N-((3S)-1-methyl-2-oxo-5-phenyl-2,3-dihydro-1H-benzo[e][1,4]diazepin-3-yl)-propionamide (1:1 mixture of diastereomers)

Prepared from amine B and 2-(3,4dichloro-phenoxy)-propionic acid using the procedure of Step 1E shown in Scheme 1.

($^1$H, CDCl$_3$) 8.18 (1H, d, J=8.0 Hz), 8.11 (1H, d, J=8.0 Hz), 7.62–7.22 (9+9H, m), 7.14 (1H, d, J=6.3 Hz), 7.13 (1H, d, J=6.3 Hz), 6.90 (1H, d, J=8.9 Hz), 6.88 (1H, d, J=8.9 Hz), 5.52 (1H, d, J=8.2 Hz), 5.49 (1H, d, J=8.2 Hz), 4.72 (1+1H, m), 3.47 (3H, s), 3.45 (3H, s), 1.68 (3H, d, J=6.8 Hz), 1.63 (3H, d, J=6.8 Hz); MS (ES+) MH+=482.

Example 82

2-(4-Chlorophenoxy)-N-((3S)-1-methyl-2-oxo-5-phenyl-2,3-dihydro-1H-benzo[e][1,4]diazepin-3-yl)-2-phenyl-acetamide (1:1 mixture of diastereomers)

Prepared from amine B and 2-(4chloro-phenoxy)-2-phenylacetic acid using the procedure of Step 1E shown in Scheme 1.

($^1$H, CDCl$_3$) 8.57 (1H, d, J=8.1 Hz), 7.59–7.22 (16H, m), 6.96 (2H, m), 5.61 (1H, s), 5.49 (1H, d, J=8.2 Hz), 6.88 (1H, d, J=8.9 Hz), 5.52 (1H, d, J=8.2 Hz), 5.49 (1H, d, J=8.2 Hz), 3.49 (3H, s); MS (ES+) MH$^+$=510.

Example 83

(2S)-3-3,4-Dichlorophenyl)-N-((3S)-1-methyl-2-oxo-5-phenyl-2,3 dihydro-1H-benzo[e][1,4]diazepin-3-yl)-2-phenyl-propionamide Prepared from amine B and (2S)-3-(3,4-dichlorophenyl)-2-phenyl-propionic acid using the procedure of Step 1E shown in Scheme 1.

($^1$H, CDCl$_3$) 7.58–7.20 (17H, m), 6.98 (1H, dd, J=2, 8), 5.41 (1H, d, J=7.7), 3.76 (1H, t, 7.5), 3.54 (1H, dd, J=7.7, 13.8), 3.39 (3H, s), 2.94 (1H, dd, J=7.3, 13.8); MS (CI+) MH+543.

Example 84

(2R)-3-(3,4-Dichlorophenyl)-N-(3S)-1-methyl-2-oxo-5-phenyl-2,3dihydro-1H-benzo[e][1,4]diazepin-3-yl)-2-phenyl-propionamide Prepared from amine B and (2R)-3-(3,4-dichlorophenyl)-2phenyl-propionic acid using the procedure of Step 1E shown in Scheme 1.

($^1$H, CDCl$_3$) 7.60–7.17 (17H, m), 6.94 (1H, dd, J=2, 8), 5.45 (1H, d, J=7.7) 3.77 (1H, t, 7.5), 3.43 (1H, dd, J=7.7, 13.8), 3.42 (3H, s), 3.01 (1H, dd, J=7.3, 13.8); MS (CI+) MH+543.

Example 85

(2S)-3-(3,4-Dichlorophenyl)-2-methyl-N-((3S)-1-methyl-2-oxo-5-phenyl-2,3-dihydro-1H-benzo[e][1,4]diazepin-3-yl)-propionamide Prepared from amine B and (2S)-3-(3,4dichlorophenyl)-2-methyl-propionic acid using the procedure of Step 1E shown in Scheme 1.

$^1$H NMR (CDCl$_3$) 1.28 (3H, d, J=6.4 Hz), 2.63–2.71 (2H, m), 2.96–3.00 (1H, m), 3.46 (3H, s), 5.44 (1H, d, J=8.0 Hz), 7.05–7.07 (1H, m), 7.22–7.62 (12H, m); MS (ES+) MH$^+$=480.

Example 86

(2S)-3-(3,4-Difluorophenyl)-2-methyl-N-((3S)-1-methyl-2-oxo-5-phenyl-2,3-dihydro-1H-benzo[e][1,4]diazepin-3-yl)-propionamide Prepared from amine B and (2S)-3-(3,4-difluorophenyl)-2-methyl-propionic acid using the procedure of Step 1E shown in Scheme 1.

$^1$H NMR (CDCl$_3$) 1.27 (3H, d, J=6.6 Hz), 2.63–2.72 (2H, m), 3.00–3.02 (1H, m), 3.46 (3H, s), 5.46 (1H, d, J=8.0 Hz), 6.89–7.09 (3H, m), 7.22–7.62 (9H, m); MS (ES+) MH$^+$=448.

Example 87

2-(2,4-dichlorophenoxy)-N-[(3S)-1-methyl-2-oxo-5-phenyl-2,3-dihydro-1H-benzo[e][1,4]diazepin-3-yl]propanamide Prepared from amine B and 2-(2,4-dichlorophenoxy)propionic acid using the procedure of Step 1E shown in Scheme 1.

Less polar diastereomer $^1$H, CDCl$_3$: 1.66 (3H, d, J=6.7), 3.48 (3H, s), 4.81 (1H, dd, J=6.7 and 13.4), 5.53 (1H, d, J=8.0), 6.97 (1H, m), 7.23 (3H, m), 7.36–7.48 (5H, m), 7.61 (3H, m), 8.45 (1H, d, J=8.0); MS(CI+), MH+=482 More polar diastereomer $^1$H, CDCl$_3$: 1.72 (3H, d), 3.46 (3H, s), 4.73 (1H, m), 5.52 (1H, d, J=6.3), 6.98 (1H, d, J=8.8), 7.11 (3H, m), 7.38–7.42 (5H, m), 7.72 (3H, m), 8.42 (1H, m); MS(CI+), MH+=482

Example 88

(2R)-3-(3,4-Dichlorophenyl)-N-[(3S)-2-oxo-5-phenyl-1-(2,2,2-trifluoroethyl)-2,3-dihydro-1H-benzo[e][1,4]diazepin-3-yl]-2-(3-thienyl)propanamide Prepared from 3-amino-5-phenyl-1-(2,2,2-trifluoroethyl)-1,3-dihydro-2H-benzo[e][1,4]diazepin-2-one (WO96/05839) and (2R)-3-(3,4-dichlorophenyl)-2-(3-thienyl) propanoic acid using the procedure of Step 1E shown in Scheme 1.

$^1$H NMR (CDCl$_3$) 3.04 (1H, dd, J=13.8, 7.5 Hz), 3.39 (1H, dd, J=13.8, 7.5 Hz), 3.92 (1H, t, J=7.5 Hz), 4.14 (1H, dq, J=15.4, 7.7 Hz), 5.17 (1H, dq, J=15.4, 8.3 Hz), 5.4 (1H, d, J=8.1 Hz), 6.93–9.96 (1H, m), 7.10–7.54 (14H, m), 7.58–7.63 (1H, m)

Example 89

(2S)-3-(3,4-Dichlorophenyl)-2-methyl-N-[2-oxo-5-(1-oxo-1,2,3,4-tetrahydro-6-isoquinolinyl)-1-(2,2,2-trifluoroethyl)-2.3-dihydro-1H-benzo[e][1,4]diazepin-3-yl]propanamide Prepared via Scheme 4 followed by Step 3D and Step 3E (with 2-(1-oxo-1,2,3,4-tetrahydro-6-isoquinolinyl-4,4,5,5-tetramethyl-1,3,2-dioxa-borolane).

(1H, NMR, 400 MHz, DMSO, two diastereomers) 9.32 (0.5H, d, J=7.9), 9.27 (0.5H, d, J=7.9), 8.1 (1H, s), 7.92–7.19 (10H, m), 5.41 (0.5H, d, J=8.0), 5.37 (0.5H, d, J=8.0), 5.15–5.08 (1H, m), 4.82–4.75 (1H, m), 3.5–3.3 (3H, m), 3.0–2.5 (4H, m), 1.04 (1.5H, d, J=6.5), 0.99 (1.5H, d, J=6.5). m/z: Found 617 (MH$^+$), C$_{30}$H$_{25}$NO$_3$Cl$_2$F$_3$+H$^+$ requires 617.

Example 90

4-[3-{[(2S)-3-(3,4-Dichlorophenyl)-2-methylpropanoyl]amino}-2-oxo-1-(2,2,2-trifluoroethyl)-2,3-dihydro-1H-benzo[e][1,4]diazepin-5-yl]benzamide Prepared via Scheme 4 followed by Step 3D and Step 3E (with 2-(4-(carbamoyl)phenyl)-4,4,5,5-tetramethyl-1,3,2-dioxa-borolane).

(1H NMR, 400 MHz, DMSO, two diastereomers) 9.34 (0.5H, d, J=8.0), 9.26 (0.5H, d, J=8.0), 8.08–7.20 (13H, m), 5.41 (0.5 H, d, J=8.0), 5.38 (0.5H, d, J=8.0), 5.17–5.07 (1H, m), 4.82–4.73 (1H, m), 3.0–2.5 (3H, m), 1.05–1.95 (3H, m). m/z: Found 591 (MH$^+$), C$_{28}$H$_{23}$N$_4$O$_3$F$_3$Cl$_2$+H$^+$ requires 591.

Example 91

(2S)-3-(3,4-dichlorophenyl)-2-methyl-N-[1-methyl-5-(4-morpholinyl)-2-oxo-2,3-dihydro-1H-1,4-benzodiazepin-3-yl)]propanamide Prepared by reaction of the product of Step 3D (Scheme 3) with morpholine using the procedure of Step 3F shown in Scheme 3.

$^1$H NMR (CDCl$_3$)(1:1 mixture of diastereomers)1.19 (3H, d, J=6.5 Hz), 2.58–2.64 (2H, m), 2.95–2.99 (1H, m), 3.18 (4H, m), 3.40 (3H, s), 3.65–3.70 (2H, m), 3.77–3.82 (2H, m), 5.21–5.23 (1H, m), 6.75–6.95 (1H,m), 7.01–7.06 (1H, m), 7.22–7.35 (4H, m), 7.52–7.56 (2H, m); MS (ES+) MH$^+$=489.

Example 92

(2S)-3-(3,4-dichlorophenyl)-2-methyl-N-{1-methyl-2-oxo-5-[4-(trifluoromethyl)phenyl]-2,3-dihydro-1H-1,4-benzodiazepin-3-yl}propanamide Prepared by reaction of the product from Step 3D (Scheme 3) with 4-(trifluoromethyl)benzene boronic acid using the procedure of Step 3E shown in Scheme 3.

$^1$H NMR (CDCl$_3$)(1:1 mixture of diastereomers) 1.19–1.29 (3H, m), 2.65–2.72 (2H, m), 2.97–3.06 (1H, m), 3.46 (3H, s), 5.44 (0.5H, d, J=7.9 Hz), 5.49 (0.5H, d, J=8.1 Hz), 7.04–7.11 (1H, m), 7.24–7.43 (6H, m), 7.60–7.72 (5H, m); MS (ES+) MH$^+$=548.

Example 93

(2S)-3-(3,4-dichlophenyl)-2-methyl-N-[1-methyl-2-oxo-5-(5-pyrimidinyl)-2,3-dihydro-1H-1,4-benzodiazepin-3yl]propanamide Prepared by reaction of the product from Step 3D (Scheme 3) with pyrimidine-5-boronic acid using the procedure of Step 3E shown in Scheme 3.

$^1$H NMR (CDCl$_3$)(2:1 mixture of diastereomers) 1.23–1.30 (3H, m), 2.65–2.72 (2H, m), 2.94–3.07 (1H, m), 3.45–3.51 (3H, m), 5.44–5.52 (1H, m), 7.04–7.10 (1H, m), 7.22–7.47 (5H, m), 7.64–7.70 (1H, m), 8.96 (2H, m), 9.29 (1H, m); MS (ES+) MH$^+$=482.

Example 94

(2S)—N-[5-(1-benzothien-2-yl)-1-methyl-2-oxo-2,3-dihydro-1H-1,4-benzodiazepin-3-yl]-3-(3,4-dichlorophenyl)-2-methylpropanamide Prepared by reaction of the product from Step 3D (Scheme 3) with benzo[b]thiophene-2-boronic acid using the procedure of Step 3E shown in Scheme 3.

$^1$H NMR (CDCl$_3$)(least polar diastereomer) 1.26 (3H, d, J=6.3 Hz), 2.66–2.71 (2H, m), 2.97–3.01 (1H, m), 3.44 (3H, s), 5.52 (1H, d, J=8.1 Hz), 7.07 (1H, dd, J=2.1,6.1 Hz), 7.17 (1H, d, J=8.1 Hz), 7.26 (1H, m), 7.31–7.41 (6H, m), 7.62–7.84 (4H, m). $^1$H NMR (CDCl$_3$)(more polar diastereomer) 1.24 (3H, d, J=6.6 Hz), 2.68 (2H, m), 3.05 (1H, m), 3.44 (3H, s), 5.55 (1H, d, J=8.3 Hz), 7.13 (2H, m), 7.33–7.43 (7H, m), 7.60–7.90 (4H, m).

Example 95

(2S)-3-(3,4-dichlorophenyl)-N-[5-(2-methoxy4-pyridinyl)-2-oxo-2,3-dihydro-1H-1,4-benzodiazepin-3yl]-2methylpropanamide Prepared from 3-amino-5-(2-methoxypyridin-4-yl)-2-oxo-2,3-dihydro-1H-benzo[e][1,4]diazepine (WO93/07131) and (2S)-3-(3,4-dichlorophenyl)-2-methyl-propionic acid using the procedure of Step 1E shown in Scheme 1.

$^1$H NMR (CDCl$_3$)(least polar diastereomer)1.29 (3H, d, J=6.5 Hz), 2.68–2.70 (2H, m), 2.99–3.03 (1H, m), 3.94 (3H, s), 5.50 (1H, d, J=7.9 Hz), 6.80 (1H,s), 7.03–7.07 (2H, m), 7.15–7.35 (8H, m), 7.54–7.58 (1H, m) 8.18–8.20 (1H, m,), 8.51 (1H, s); MS (ES+) MH$^+$=497.

Example 96

(2S)-3-(3,4-difluorophenyl)-2-methyl-N-{1-methyl-2-oxo-5-[4-(trifluoromethyl)-1-piperidinyl]-2,3-dihydro-1H-1,4-benzodiazepin-3-yl}propanamide Prepared from 3-amino-1-methyl-5-(4-trifluoromethyl-piperidin-1-yl)-1,3-dihydro-2H-benzo[e][1,4]diazepin-2-one (WO94/03437) and (S)-3-(3,4-difluorophenyl)-2-methyl-propionic acid using the procedure of Step 1E shown in Scheme 1.

$^1$H NMR (CDCl$_3$)(1:1 mixture of diastereomers) 1.18–1.22 (3H, m), 1.67–2.20 (4H, m), 2.56–2.72 (6H, m), 3.39 (3H, s), 3.61 (1H, m), 4.00 (1H, m) 5.18–5.21 (1H, m), 6.86–7.34 (6H, m), 7.51–7.56 (2H, m).

Example 97

(2S)-3-(3,4-dichlorophenyl)-2-methyl-N-(2-oxo-5-phenyl-2,3-dihydro-1H-1,4-benzodiazepin-3-yl)propanamide Prepared from (±)-3-amino-5-phenyl-1,3-dihydro-2H-1,4-benzodiazepin-2-one (*J. Org. Chem.* 1987, 52, 3232) and (2S)-3-(3,4-dichlorophenyl)-2-methyl-propionic acid using the procedure of Step 1E shown in Scheme 1.

$^1$H NMR (CDCl$_3$)(1:1 mixture of diastereomers) 1.25–1.30 (3H, m), 2.65–2.70 (2H, m), 3.02–3.11 (1H, m), 5.49 (0.5H, d, J=8.0 Hz), 5.52 (0.5H, d, J=8.0 Hz), 6.97–7.54 (14H, m).

Example 98

(2S)—N-[1-(2-amino-2-oxoethyl)-2-oxo-5-phenyl-2,3-dihydro-1H-1,4-benzodiazepin-3-yl]-3-(3,4-dichlorophenyl)-2-methylpropanamide Prepared from (2S)-3-(3,4-dichlorophenyl)-2-methyl-N-(2-oxo-5-phenyl-2,3-dihydro-1H-1,4-benzodiazepin-3-yl)propanamide and 2-bromoacetamide in an analogous fashion to that described in Step 4C shown in scheme 4.

$^1$H NMR (CDCl$_3$)(1:1 mixture of diastereomers) 0.98–1.04 (3H, m), 2.55–2.64 (1H, m), 2.80–3.05 (2H, m), 3.90–4.60 (2H, m), 5.82–5.90 (1H, m), 7.10 (1H, m), 7.22–7.31 (3H, m), 7.44–7.70 (10H, m), 9.00–9.10 (1H, m).

Example 99

(2S)—N-{1-[(5-chloro-1,2,3-thiadiazol-4-yl)methyl]-2-oxo-5-phenyl-2,3-dihydro-1H-1,4-benzodiazepin-3yl}-3-(3,4-dichlorophenyl)-2-methylpropanamide Prepared from (2S)-3-(3,4-dichlorophenyl)-2-methyl-N-(2-oxo-5-phenyl-2,3-dihydro-1H-1,4benzodiazepin-3-yl)propanamide and Maybridge SEW 03512 in an analogous fashion to that described in Step 4C shown in scheme 4.

$^1$H NMR (CDCl$_3$)(1:1 mixture of diastereomers) 1.23–1.28 (3H, m), 2.63–2.70 (2H, m), 2.99–3.06 (1H, m), 5.26 (0.5H, d, J=3.0 Hz), 5.31 (0.5H, d, J=3.0 Hz), 5.56–5.60 (1H, m), 5.72–5.79 (1H, m), 6.97–7.73 (13H, m); MS (ES+) MH$^+$=598.

Example 100

(2S)—N-[4-cyanomethyl)-2-oxo-5-phenyl-2,3-dihydro-1H-1,4-benzodiazepin-3-yl]-3-(3,4dichlorophenyl)-2-methylpropanamide Prepared from (2S)-3-(3,4dichlorophenyl)-2-methyl-N-(2-oxo-5-phenyl-2,3-dihydro-1H-1,4-benzodiazepin-3yl)propanamide and chloroacetonitrile in an analogous fashion to that described in Step 4C shown in scheme 4.

$^1$H NMR (CDCl$_3$)(least polar diastereomer)1.28 (3H, d, J=6.5 Hz), 2.66–2.73 (2H, m), 2.96–3.01 (1H, m), 4.79 (2H, dd, J=17.4, 54.6 Hz), 5.57 (1H, d, J=8.1 Hz), 7.04–7.71 (13H, m); MS (ES+) MH$^+$=505. $^1$H NMR (CDCl$_3$)(more polar diastereomer)1.26 (3H, d, J=6.4 Hz), 2.65–2.71 (2H, m), 3.01–3.08 (1H, m), 4.76 (2H, m), 5.59 (1H, d, J=8.3 Hz), 7.06 (2H, m), 7.34–7.55 (10H, m), 7.66–7.71 (1E, m); MS (ES+) ME+=505.

Unless otherwise indicated, Examples 101–134 were prepared from (S)-3-amino-1-methyl-5-phenyl-2,3-dihydro-1H-1,4-benzodiazepin-2-one (*J. Org. Chem.* 1987, 52, 955 and 3232) or 3-amino-5-phenyl-2,3dihydro-1H-1,4-benzodiazepin-2-one (*J. Org. Chem.* 1995, 60, 730) or 3-amino-5-phenyl-1-(2,2,2-trifluoroethyl)-2,3-dihydro-1H-1,4-benzodiazepin-2-one (*J. Med. Chem.* 1997, 40, 3865) by coupling with a carboxylic acid using the procedure of Step 1E shown in Scheme 1. The required carboxylic acids were prepared by methods shown in Scheme 5 and Scheme 6 or by literature methods (*Org. Synth.* 1990, 68, 83–90; *J. Org. Chem.* 1992, 57, 2768; *Aldrichimica Acta*, 1982, 53,23; *J. Am. Chem. Soc.* 1991, 113, 4026; *J. Chem. Soc., Perkin Trans.* 1, 1994, 1141–7).

Example 101

(2R,3R)-3-(3,4-difluorophenyl)-3-hydroxy-2-methyl-N-[(3S)-1-methyl-2-oxo-5-phenyl-2,3-dihydro-1H-1,4-benzodiazepin-3-yl]propanamide m/z (ES+) 464

Example 102

3-(3,4-dichlorophenyl)-2-methyl-N-[(3S)-1-methyl-2oxo-5-phenyl-2,3-dihydro-1H-1,4benzodiazepin-3-yl]-3-oxopropanamide Prepared from (2R, 3R)-3-(3,4-dichlorophenyl)-3-hydroxy-2-methyl-N-((3S)-1-methyl-2-oxo-5-phenyl-2,3-dihydro-1H-1,4-benzodiazepin-3-yl)-propionamide by oxidation with Dess-Martin periodinane m/z (ES+) 494

Example 103

(2R,3S)-3-(3,4dichlorophenyl)-2,3-dimethoxy-N-[(3S)-1-methyl-2-oxo-5-phenyl-2,3-dihydro-1H-1,4-benzodiazepin-3-yl]propanamide Prepared from methyl (2R,3S)-3-(3,4dichlorophenyl)-2,3-dihydroxypropanoate (cf. *J. Org. Chem.*, 1992, 57, 2768) by alkylation with methyl iodide/potassium carbonate followed by ester hydrolysis with lithium hydroxide and subsequent coupling using the method of Step 1E (Scheme 1).

m/z (ES+) 526

Example 104

(2R,3R)-3-(3,4-dichlorophenyl)-3-methoxy-2-methyl-N-[(3S)-1-methyl-2oxo-5-phenyl-2,3-dihydro-1H-1,4-benzodiazepin-3-yl]propanamide Prepared from (2R, 3R)-3-(3,4-dichlorophenyl)-3-hydroxy-2-methyl-N-((3S)-1-methyl-2-oxo-5-phenyl-2,3-dihydro- 1H-1,4-benzodiazepin-3-yl)-propionamide by alkylation with methyl iodide/sodium hydride.

m/z (ES+) 510

Example 105

(3E)-3-(3,4-dichlorophenyl)-3-(hydroxyimino)-2-methyl-N-[(3S)-1-methyl-2-oxo-5-phenyl-2,3-dihydro-1H-1,4-benzodiazepin-3yl]propanamide Prepared from 3-(3,4-dichlorophenyl)-2-methyl-N-[(3S)-1-methyl-2-oxo-5-phenyl-2,3-dihydro-1H-1,4-benzodiazepin-3-yl]-3oxopropanamide by treatment with hydroxylamine hydrochloride.

m/z (ES+) 509

Example 106

(1R,2R)-1–3,4-dichlorophenyl)-2-methyl-3-{[(3S)-1-methyl-2-oxo-5-phenyl-2,3-dihydro-1H-1,4-benzodiazepin-3-yl]amino}-3-oxopropyl sulfmate Prepared from (2R, 3R)-3–3,4-dichlorophenyl)-3-hydroxy-2-methyl-N-((3S)-1-methyl-2-oxo-5-phenyl-2,3-dihydro-1H-1,4-benzodiazepin-3-yl)-propionamide by reaction with sulfamoyl chloride.

m/z (ES+) 575

Example 107

(2R,3S)-3-(hydroxymethyl)-2-isobutyl-N-(1-methyl-2-oxo-5-phenyl-2,3-dihydro-1H-1,4-benzodiazepin-3-yl)hexanamide Prepared from (2S,3R)-3-[[(2,3-dihydro-1-methyl-2-oxo-5-phenyl-1H-1,4-benzodiazepin-3-yl)amino]carbonyl]-5-methyl-2-(2-propenyl)-hexanoic acid (WO0038618) by treatment with isobutyl chloroformate followed by sodium borohydride reduction and hydrogenation.

m/z (ES+) 450

Example 108

(2R,3R)-3-(3,4-dichlorophenyl)-3-hydroxy-2-methyl-N-[(3S)-2-oxo-5-phenyl-2,3dihydro-1H-1,4benzodiazepin-3-yl]propanamide m/z (ES+) 482

Example 109

(2R,3R)-3-(3,4-difluorophenyl)-3-(formylamino)-2-methyl-N-[(3S)-1-methyl-2-oxo-5-phenyl-2.3-dihydro-1H-1,4-benzodiazepin-3-yl]propanamide Prepared from tert butyl 3-(3,4-difluorophenyl)-2-methyl-prop-2-enoate by treatment with (S)-(−)-N-benzyl-α-methyl benzylamine/butyl lithium (c.f *J. Chem. Soc., Perkin Trans.* 1, 1994, 1141) followed by hydrogenolysis (hydrogen/palladium on charcoal/acetic acid/40 psi), acylation (formic acetic anhydride), ester hydrolysis (TFA) and finally coupling (procedure of Step 1E (Scheme 1)).

m/z (ES+) 491

Example 110

(2R)-3-[3-fluoro-4-(trifluorom thyl)phenyl]-2-methyl-N-[(3S)-1-methyl-2-oxo-5-phenyl-2,3-dihydro-1H-1,4-benzodiazepin-3-yl]propanamide m/z (ES+) 498

Example 111

4-(4chlorophenyl)-2-(4-fluorophenyl)-N-[(3S)-1-methyl-2-oxo-5-phenyl-2,3-dihydro-1H-1,4-benzodiazepin-3yl]-4-oxobutanamide m/z (ES+) 554

Example 112

4-(4-chlorophenyl)-2-(4-fluorophenyl)-4-hydroxy-N-[(3S)-1-methyl-2-oxo-5-phenyl-2,3-dihydro-1H-1,4-benzodiazepin-3-yl]butanamide (less polar isomers)

Prepared from 4-(4-chlorophenyl)-2-(4-fluorophenyl)-N-[(3S)-1-methyl-2-oxo-5-phenyl-2,3-dihydro-1H-1,4-benzodiazepin-3-yl]-4-oxobutanamide by treatment with sodium borohydride.

m/z (ES+) 556

Example 113

4-(4chlorophenyl)-2-(4-fluorophenyl)-4-hydroxy-N-[(3S)-1-methyl-2-oxo-5-phenyl-2,3-dihydro-1H-1,4-benzodiazepin-3-yl]butanamide (more polar isomers)

Prepared from 4-(4-chlorophenyl)-2-(4-fluorophenyl)-N-[(3S)-1-methyl-2oxo-5-phenyl-2,3-dihydro-1H-1,4-benzodiazepin-3-yl]-4-oxobutanamide by treatment with sodium borohydride.

m/z (ES+) 556

Example 114

(2R)-3-(3,4-difluorophenyl)-2-(4-fluorophenyl)-N-(2-oxo-5-phenyl-2,3-dihydro-1H-1,4-benzodiazepin-3-yl)propanamide m/z (ES+) 514

Example 115

3-(3,4-difluorophenyl)-2-methyl-N-[(3S)-1-methyl-2-oxo-5-phenyl-2,3-dihydro-1H-1,4-benzodiazepin-3-yl]-3-oxopropanamide Prepared from (2R,3R)-3-(3,4-difuorophenyl)-3-hydroxy-2-methyl-N-[(3S)-1-methyl-2-oxo-5-phenyl-2,3-dihydro-1H-1,4-benzodiazepin-3-yl]propanamide by treatment with Dess-Martin periodinane.

m/z (ES+) 462

Example 116

(3E)-3-(3,4-difuorophenyl)-3-(hydroxyimino)-2-methyl-N-[(3S)-1-methyl-2-oxo-5-phenyl-2,3-dihydro-1H-1,4-benzodiazepin-3yl]propanamide Prepared from 3–3,4-difluorophenyl)-2-methyl-N-[(3S)-1-methyl-2-oxo-5-phenyl-2,3dihydro-1H-1,4-benzodiazepin-3-yl]-3-oxopropanamide by treatment with hydroxylamine hydrochloride.

m/z (ES+) 477

Example 117

(2R)-3-(3,4-difluorophenyl)-2-(4-fluorophenyl)-N-[(3S)-1-methyl-2-oxo-5-phenyl-2,3-dihydro-1H-1,4-benzodiazepin-3yl]propanamide m/z (ES+) 528

Example 118

(2R)-3-(3,4-difluorophenyl)-2-(4-fluorophenyl)-N-[(3S)-2-oxo-5-phenyl-1-(2,2,2-trifluorophenyl)-2,3-dihydro-1H-1,4-benzodiazepin-3-yl]propanamide m/z (ES+) 596

Example 119

(2R)-3-(3,4-difuorophenyl)-2-(4-fluorophenyl)-N-(2-oxo-5-phenyl-2,3-dihydro-1H-1,4-benzodiazepin-3-yl)propanamide m/z (ES+) 514

Example 120

3-(3,4-difluorophenyl)-4-hydroxy-2-methyl-N-[(3S)-1-methyl-2-oxo-5-phenyl-2,3-dihydro-1H-1,4-benzodiazepin-3-yl]butanamide Prepared from methyl methacrylate as outlined below (c.f WO 0024720 and *Acta Chem. Scand.*, 1990, 44, 202):

To a stirred solution of methyl methacrylate (3.15 g, 31.5 mmol.) and benzyltriethylammonium chloride (0.72 g, 3.2 mmol.) in aqueous NaOH (12.6 ml of a 50% w/w solution, 0.16 mol.) was slowly added bromoform (15.95 g, 63 mmol.) and the deep brown solution stirred at room temperature for 18 hours. The mixture was partitioned between dichloromethane (50 ml) and water (50 ml), the layers separated and the aqueous layer extracted with further dichloromethane (50 ml). The organic layers were combined, washed with brine, dried ($MgSO_4$) and evaporated to give the desired methyl 2,2-dibromo-1-methylcyclopropanecarboxylate (8.0 g, 93%). This was dissolved in a mixture of TBF (70 ml) and water (30 ml) and LiOH (1.05 g, 44 mmol.) added. The mixture was vigorously stirred at room temperature for 20 hours then the THF was evaporated and the aqueous residue washed with ether (2×25 ml), acidified with 5N HCl to pH1 and extracted with ethyl acetate (2×50 ml). The combined ethyl acetate layers were dried ($MgSO_4$) and evaporated to give the desired 2,2-dibromo-1-methylcyclopropanecarboxylic acid as a tan solid (4.2 g, 55%) which was dissolved in 2,2,2-trifluoroethanol (200 ml). Silver trifluoroacetate (5.75 g, 26 mmol.) was added under nitrogen and the reaction refluxed in the dark for 16 hours after which time the mixture was filtered and evaporated. The residue was taken up in ether (100 ml), washed with water (100 ml), and with saturated aqueous $NaHCO_3$ (100 ml), then dried ($MgSO_4$) and evaporated to give an oil (1.1 g) which was purified by chromatography ($SiO_2$; dichloromethane:hexane; 4:1 w/w) to afford the desired 4-bromo-3-methyl-2(5H)-furanone (520 mg).

To a solution of 4-bromo3-methyl-2(5H)-furanone (510 mg, 2.9 mmol.) and 3,4-difluorophenylboronic acid (500 mg, 3.2 mmol.) in dry dimethoxyethane (20 ml) was added sodium carbonate (4.3 ml of a 2M aqueous solution, 8.6 mmol.) and the mixture degassed by nitrogen bubbling for 15 minutes. Tetrakis(triphenylphosphine)palladium(0) (50 mg) was then added, the mixture degassed for a further 5 minutes then heated to 90° C. for 2 hours. The reaction was cooled and partitioned between ethyl acetate (50 ml) and water (50 ml). The organic layer was washed with brine (50 ml), dried ($MgSO_4$) and evaporated to give an oil (0.73 g) which was purified by chromatography ($SiO_2$; dichloromethane:hexane; 4:1 w/w) to afford the desired 4-(3,4-difluorophenyl)-3-methyl-2(5H)-furanone (450 mg).

4-(3,4-Difluorophenyl)-3-methyl-2(5H)-furanone (235 mg, 1.1 mmol.) was dissolved in methanol (20 ml) in a thick-walled flask and degassed by nitrogen bubbling. Palladium on charcoal (10%, 300 mg) was added and the flask shaken under an atmosphere of hydrogen at 40 psi on a Parr hydrogenator for 72 hours. The reaction was placed under nitrogen and filtered through a pad of Celite® washing well with methanol and the combined washings evaporated to afford the desired cis-dihydro-4-(3,4-difluorophenyl)-3-methyl-2(3H)-furanone as an oil (230 mg).

To a stirred solution of (S)-3-amino-1-methyl-5-phenyl-2,3-dihydro-1H-1,4benzodiazepin-2-one (148 mg, 0.56 mmol.; *J. Org. Chem.* 1987, 52, 955 and 3232) in dichloromethane (5 ml) under an atmosphere of nitrogen was added dropwise over five minutes trimethylaluminium (0.28 ml of a 2M solution in hexanes, 0.56 mmol.) and the mixture stirred 10 minutes at ambient temperature. Cis-dihydro-4-(3,4-difluorophenyl)-3-methyl-2(3H)-furanone (79 mg, 0.37 mmol.) as a solution in dry dichloromethane (3 ml) was then added and the mixture heated to reflux for 15 hours then cooled and poured into water (10 ml). Dichloromethane (10 ml) was added and the layers separated. The organic layer was washed with 1N HCl (2×10 ml), 1N NaOH (10 ml), dried ($MgSO_4$) and evaporated to give an oil (145 mg) which was purified by chromatography ($SiO_2$; dichloromethane: ethyl acetate; 1:2 to 1:4 w/w gradient) to afford the desired product (31 mg).

m/z (ES+) 478

Example 121

(2R,3R)-3-(3,4-difluorophenyl)-2-(4fluorophenyl)-3-hydroxy-N-[(3S)-1-methyl-2-oxo-5-phenyl-2,3-dihydro-1H-1,4-benzodiazepin-3-yl]propanamide m/z (ES+) 544

Example 122

(2R,3R)-3-(3,4-difluorophenyl)-2-(4-fluorophenyl)-3-hydroxy-N-(2-oxo-5-phenyl-2,3-dihydro-1H-1,4-benzodiazepin-3-yl)propanamide m/z (ES+) 530

Example 123

(2R,3R)-3-(3,4-dichlorophenyl)-2-(4fluorophenyl)-3-hydroxy-N-[(3S)-1-methyl-2-oxo-5-phenyl-2,3-dihydro-1H-1,4-benzodiazepin-3-yl]propanamide m/z (ES+) 576

Example 124

(2R,3R)-3-(3,4-dichlorophenyl)-2-(4-fluorophenyl)-3-hydroxy-N-(2-oxo-5-phenyl-2,3-dihydro-1H-1,4-benzodiazepin-3-yl)propanamide m/z (ES+) 562

Example 125

(2R,3R)-3-(3,4dichlorophenyl)-2-(4-fluorophenyl)-3-methoxy-N2-oxo-5phenyl-2,3-dihydro-1H-1,4-benzodiazepin-3-yl)propanamide Prepared from the product from Step 6A (Scheme 6) by reaction with 3,4-dichlorobenzaldehyde using the procedure of Step 6B (Scheme 6) followed by treatment with methyl triflate and 2,6-di-tertbutyl-4-methylpyridine. Deprotection (Step 6D (Scheme 6)) and subsequent coupling (using the procedure of Step 1E (Scheme 1) with 3-amino-5-phenyl-2,3dihydro-1H-1,4-benzodiazepin-2-one afforded the product.

m/z (ES+) 576

Example 126

(2S,3R)-3-(3,4-difluorophenyl)-2-(4-fluorophenyl)-N-[(3S)-1-methyl-2-oxo-5-phenyl-2,3-dihydro-1H-1,4-benzodiazepin-3-yl]propanamide Prepared from (2S,3R)-3-(3,4-difluorophenyl)-2-(4-fluorophenyl)-N-[(3S)-1-methyl-2-oxo-5-phenyl-2,3dihydro-1H-1,4benzodiazepin-3yl]pent-4-enamide (Scheme 5) by hydrogenation with palladium on charcoal catalyst.

m/z (ES+) 556

Example 127

(2S,3R)-4-bromo-3-(3,4-difluorophenyl)-2-(4-fluorophenyl)-N-[(3S)-1-methyl-2-oxo-5-phenyl-2,3-dihydro-1H-1,4-benzodiazepin-3yl]butanamide Prepared as in Scheme 5.

m/z (ES+) 620/622

Example 128

(2S,3R)-3-(3,4-difluorophenyl)-2-(4-fluorophenyl)-4-hydroxy-N-(2-oxo-5phenyl-2,3-dihydro-1H-1,4-benzodiazepin-3-yl)butanamide Prepared from the product of Step 5B (Scheme 5) by reaction with 3-amino-5-phenyl-2,3-dihydro-1H-1,4-benzodiazepin-2-one under the conditions of Step 5C followed by Step 5D (both Scheme 5).

m/z (ES+) 544

Example 129

4-[((2R,3S)-2-(3,4-difluorophenyl)-3-(4fluorophenyl)-4-{[(3S)-1-methyl-2oxo-5-phenyl-2,3-dihydro-1H-1,4-benzodiazepin-3yl]amino}-4-oxobutyl)oxy]-4-oxobutanoic acid Prepared from reaction of (2S,3R)-3-(3,4-difluorophenyl)-2-(4-fluorophenyl)-4hydroxy-N-[(3S)1-methyl-2oxo-5-phenyl-2,3-dihydro-1H-1,4benzodiazepin-3-yl]butanamide with succinic anhydride.

m/z (ES+) 658

Example 130

(2S,3S)-3-(3,4-difluorophenyl)-2-(4-fluorophenyl)-3-hydroxy-N-[(3S)-1-methyl-2-oxo-5-phenyl-2,3-dihydro-1H-1,4-benzodiazepin-3yl]propanamide m/z (ES+) 544

Example 131

(2S,3S)-3-(3,4-dichlorophenyl)-2-(4-fluorophenyl)-3-hydroxy-N-[(3S)-1-methyl-2-oxo-5-phenyl-2,3-dihydro-1H-1,4-benzodiazepin-3yl]propanamide m/z (ES+) 576

Example 132

(2R,3R)-3-{[tert-butyl(dimethyl)silyl]oxy}-3-(3,4-dichlorophenyl)-2-(4fluorophenyl)-N-[(3S)-1-methyl-2oxo-5-phenyl-2,3-dihydro-1H-1,4-benzodiazepin-3-yl]propanamide Prepared from the product of Step 6C (Scheme 6) by treatment with LiOH/hydrogen peroxide (Step 6D) followed by Step 1E (Scheme 1).

m/z (ES+) 691

Example 133

(2R,3R)-2-(4-fluorophenyl)-3-[3-fluoro-4-(trifluoromethyl)phenyl]-3-hydroxy-N-[(3S)-1-methyl-2-oxo-5-phenyl-2,3-dihydro-1H-1,4-benzodiazepin-3-yl]propanamide m/z (ES+) 594

Example 134

(3R)-3-(3,4-difluorophenyl)-2-(4-fluorophenyl)-4-methoxy-N-(1-methyl-2oxo-5-phenyl-2,3-dihydro-1H-1,4-benzodiazepin-3yl)butanamide Prepared from reaction of (2S,3R)-3-(3,4-difluorophenyl)-2-(4-fluorophenyl)-4-hydroxy-N-[(3S)1-methyl-2-oxo-5-phenyl-2,3-dihydro-1H-1,4benzodiazepin-3-yl]butanamide with methyl iodide and potassium hexamethyldisilazide.

m/z (ES+) 572

Unless otherwise indicated, Examples 135 to 187 were prepared as in Scheme 3 or Scheme 7

Example 135

(2R)-3-(3,4-dichlorophenyl)-2-methyl-N-[1-methyl-2-oxo-5-(1-oxo-1,2,3,4-tefrahydroisoquinohin-6-yl)-2,3-dihydro-1H-1,4benzodiazepin-3-yl]propanamide Prepared analogously to example 136 using 6-boronyl-1-oxo-1,2,3,4-tetrahydroisoquinoline and (2S)-2-methyl-3-(3,4-dichlorophenyl)propionic acid.

m/z (ES+) 549

Example 136

(2S)-3-(3,4-difluorophenyl)-2-methyl-N-[1-methyl-2-oxo-5-(1-oxo-1,2dihydroisoquinolin-6–2,3-dihydro-1,4-benzodiazepin-3-yl]propanamide Prepared by reaction of the product from Step 7B (Scheme 7) with 6-boronyl-1-oxo-1,2-dihydroisoquinoline (prepared by treatment of 6-bromo-isoquinolone with bis(pinacolato) diboron under the reaction conditions described by N. Miyaura et al, *J. Org. Chem.*, 1995, 60, 7508–7510) under reaction conditions 7C, followed by treatment with TFA (reaction 7D), followed by reaction with (2R)-2-methyl-3-(3,4-difluorophenyl)propionic acid under reaction conditions 7E to yield the title compound.

m/z (ES+) 515

Example 137

(2S)-3-(3,4-dichlorophenyl)-2-methyl-N-[1-methyl-2-oxo-5-(1-oxo-1,2-dihydroisoquiolin-6yl)-2,3-dihydro-1H-1,4-benzodiazepin-3-yl]propanamide Prepared analogously to example 136.

m/z (ES+) 547

Example 138

(2S)-3-(3,4-difluorophenyl)-2-methyl-N-[1-methyl-2-oxo-5-(2-oxo-1,2,3,4-tetrahydroquinolin-6-yl)-2,3-dihydro-1H-1,4-benzodiazepin-3-yl]propanamide Prepared analogously to example 136.

m/z (ES+) 517

Example 139

(2S)-3-(3,4difluorophenyl)-2-methyl-N-[l-methyl-5-(2-methyl-1-oxo1,2,3,4tetrahydroisoquinolin-6-yl)-2-oxo-2,3-dihydro-1H-1,4-benzodiazepin-3-yl]propanamide Prepared analogously to example 136.

m/z (ES+) 531

Example 140

(2S)-3-(3,4-difluorophenyl)-2-methyl-N-(1-methyl-2-oxo-5-quinolin-5-yl-2,3-dihydro-1H-1,4-benzodiazepin-3yl)propanamide Prepared analogously to example 136.

m/z (ES+) 499

Example 141

(2S)-3-(3,4-difluorophenyl)-2-methyl-N-[1-methyl-2-oxo-5-(1-oxo-2,3-dihydro-1H-inden-5-yl)-2,3-dihydro-1H-1,4-benzodiazepin-3-yl]propanamide Prepared analogously to example 136.

m/z (ES+) 502

Example 142

(2S)-3-(3,4-difluorophenyl)-2-methyl-N-[1-methyl-5-(3-methyl-1H-inden-6-yl)-2-oxo-2,3-dihydro-1H-1,4-benzodiazepin-3-yl]propanamide Prepared analogously to example 136.

m/z (ES+) 500

Example 143

(2S)—N-[5-(1,3-benzodioxol-5-yl)-1-methyl-2-oxo-2,3-dihydro-1H-1,4-benzodiazepin-3-yl]-3-(3,4-difluorophenyl)-2-methylpropanamide Prepared analogously to example 158.

m/z (ES+) 492

Example 144

1-(3-{[(2S)-3-(3,4-dichlorophenyl)-2-methylpropanoyl]amino}-1-methyl-2-oxo-2,3-dihydro-1H-1,4-benzodiazepin-5yl)piperidine-4carboxamide Prepared using Scheme 3, Steps 3A-3D then 3F.

m/z (ES+) 530

Example 145

(2S)-3-(3,4-difluorophenyl)N-[5-4-methoxyphenyl)-1-methyl-2-oxo-2,3-dihydro-1H-1,4-benzodiazepin-3-yl]-2-methylpropanamide Prepared by reaction of 3-amino-2-oxo-5-(4-methoxy)phenyl-2,3-dihydro-1H-1,4benzodiazepine (prepared by methods analogous to R. G. Sherrill et al, *J. Org. Chem.*, 1995, 60, 730) with (2S)-3-(3,4-fluorophenyl)-2-methylpropionic acid under reaction conditions 7E to yield the title compound.

m/z (ES+) 478

Example 146

(2S)-3-(3,4-difluorophenyl)-2-methyl-N-[1-methyl-2-oxo-5-(5-oxo-5,6,7,8-tetrahydronaphthalen-2yl)-2,3dihydro-1H-1,4-benzodiazepin-3-yl]propanamide Prepared analogously to example 136.

m/z (ES+) 516

Example 147

(2S)-3-(3,4-difluorophenyl)-N-[5-(2,3-dihydro-1,4-benzodioxin-6-yl)-1-methyl-2-oxo-2,3-dihydro-1H-1,4benzodiazepin-3yl]-2-methylpropanamide Prepared analogously to example 136.

m/z (ES+) 506

Example 148

(2R)-3-(3,4-difiuorophenyl)-N-{(3S)-[5-(3-methoxyphenyl)-1-methyl-2-oxo2,3-dihydro-1H-1,4benzodiazepin-3-yl]}-2-methylpropanamide (less polar isomer)

Prepared by reaction of 3-amino-2-oxo-5-(3-methoxy)phenyl-2,3-dihydro-1H-1,4benzodiazepine (prepared by methods analogous to R. G. Sherrill et al, *J. Org. Chem.*, 1995, 60, 730) with (2S)-3-(3,4-difluorophenyl)-2methylpropionic acid under reaction conditions 7E to yield the title compound.

m/z (ES+) 478

Example 149

(2S)-3-(3,4-difluorophenyl)-2-methyl-N-[1-methyl-2-oxo-5-(4-oxo-4H-chromen-7-yl)-2,3-dihydro-1H-1,4-benzodiazepin-3-yl]propanamide Prepared using the route shown in Scheme 7:

7-Hydroxybenzopyran-4one (162 mg) (J. C. Jaen et al, *J. Med. Chem.*, 1991, 34, 248), triethylamine (0.3 ml), acetonitrile (5 ml) and N-phenyltriflimide (450 mg) were stirred together at room temperature for 20 min, evaporated in vacuo and purified by flash column chromatography to give 7-(trifluoromethanesulfonyl)oxybenzopyran-4-one (202 mg, 69%).

A solution of the foregoing triflate was reacted with bis(pinacolato)diboron under the general reaction conditions described by N. Miyaura et al, *J. Org. Chem.*, 1995, 60, 7508–7510. The resulting boronic ester was reacted immediately with 1-methyl-3-BOCNH-2-oxo-5-chloro-2,3-dihydro-1H-1,4-benzodiazepine under reaction conditions 7C, followed by treatment with TFA (reaction 7D), followed by reaction with (2R)-2-methyl-3-(3,4-difluorophenyl)propionic acid under reaction conditions 7E to yield the title compound.

m/z (ES+) 516

Example 150

(2S)-3-(3,4-difluorophenyl)-2-methyl-N-{1-methyl-2-oxo-5-[4-(trifluoromethoxy)phenyl]-2,3-dihydro-1H-1,4-benzodiazepin-3-yl}propanamide Prepared from the precursor of Step 7A (Scheme 7) (WO9514473) by reaction under the conditions of Step 7C, followed by reduction with triphenylphosphine/water and coupling using the procedure of Step 7E.

m/z (ES+) 532

Example 151

(2S)-3-[3-fluoro-4-(trifluoromethyl)phenyl]-2-methyl-N-[1-methyl-2-oxo-5-(1-oxo-2,3-dihydro-1H-inden-5-yl)-2,3-dihydro-1H-1,4-benzodiazepin-3-yl]propanamide Prepared analogously to example 136.

m/z (ES+) 552

Example 152

(2S)-3-(3,4-difluorophenyl)-N-{(3S)-[5-(3-methoxyphenyl)-1-methyl-2-oxo-2,3-dihydro-1H-1,4-benzodiazepin-3-yl]}-2-methylpropanamide (more polar isomer).

Prepared analogously to example 148.

m/z (ES+) 478

Example 153

(2R,3R)—N-[5-(1,3-benzodioxol-5-yl)-2-oxo-2,3-dihydro-1H-1,4-benzodiazepin-3-yl]-3-(3,4-difluorophenyl)-3-hydroxy-2-methylpropanamide Prepared by reaction of 3-amino-2-oxo-5-(3,4-methylenedioxy)phenyl-2,3-dihydro-1H-1,4-benzodiazepine (prepared by methods analogous to R. G. Sherrill et al, *J. Org. Chem.*, 1995, 60, 730) with (2R,3R)-3-(3,4difluorophenyl)-3-hydroxy-2-methylpropionic acid under reaction conditions 7E to yield the title compound.

m/z (ES+) 494

Example 154

(2R,3R)-3-(3,4-dichlorophenyl)-3-hydroxy-2-methyl-N-[1-methyl-2-oxo-5-(4-oxo-4H-chromen-7yl)-2,3-dihydro-1H-1,4-benzodiazepin-3-yl]propanamide Prepared analogously to example 149.

m/z (ES+) 564

Example 155

(2R,3R)-3-(3,4-difluorophenyl)-3-hydroxy-2-methyl-N-[1-methyl-2-oxo-5-(4oxo4H-chromen-7-yl)-2,3-dihydro-1H-1,4benzodiazepin-3yl]propanamide Prepared analogously to example 149.

m/z (ES+) 532

Example 156

(2R)-3-(3,4-difluorophenyl)-2-(4fluorophenyl)-N-[1-methyl-2-oxo-5-(4-oxo-4H-chromen-7-yl)-2,3-dihydro-1H-1,4-benzodiazepin-3-yl]propanamide Prepared analogously to example 149.

m/z (ES+) 596

Example 157

(2R)—N-[5-(1,3-benzodioxol-5-yl)-2-oxo-2,3-dihydro-1H-1,4-benzodiazepin-3-yl]-3-(3,4-difluorophenyl)-2-(4-fluorophenyl)propanamide Prepared analogously to example 153.

m/z (ES+) 558

Example 158

(2R,3R)—N-[5-(1,3-benzodioxol-5-yl)-1-methyl-2-oxo-2,3-dihydro-1H-1,4-benzodiazepin-3-yl]-3-(3,4-difluorophenyl)-3-hydroxy-2-methylpropanamide Prepared by reaction of 1-methyl-3-amino-2-oxo-5-(3,4-methylenedioxy)phenyl-2,3-dihydro-1H-1,4benzodiazepine (prepared by methods analogous to R. G. Sherrill et al, *J. Org. Chem.*, 1995, 60, 730) with (2R,3R)-3-(3,4-difluorophenyl)-3-hydroxy-2-methylpropionic acid under reaction conditions 7E.

m/z (ES+) 508

Example 159

(2S)-3–3,4-dichlorophenyl)-2-methyl-N-[1-methyl-2-oxo-5–5-oxo-5,6,7,8-tetrahydronaphthalen-2-yl)-2,3-dihydro-1H-1,4-benzodiazepin-3-yl]propanamide Prepared analogously to example 136.

m/z (ES+) 548

Example 160

(2R)-3-(3,4-dichlorophenyl)-2-(4-fluorophenyl)-N-[1-methyl-2-oxo-5-(5-oxo-5,6,7,8-tetrahydronaphthalen-2yl)-2,3-dihydro-1H-1,4-benzodiazepin-3-yl]propanamide Prepared analogously to example 136.

m/z (ES+) 628

Example 161

(2R3-(3,4-difuorophenyl)-2-(4-fluorophenyl)-N-[1-methyl-2-oxo-5-(5-oxo-5,6,7,8-tetrahydronaphthalen-2-yl)-2,3-dihydro-1H-1,4-benzodiazepin-3-yl]propanamide Prepared analogously to example 136.

m/z (ES+) 596

Example 162

(2S)—N-[5-(1,3-benzodioxol-5-yl)-2-oxo-2,3-dihydro-1H-1,4-benzodiazepin-3-yl]-3-(3,4-difluorophenyl)-2-methylpropanamide Prepared analogously to example 153.
m/z (ES+) 478

Example 163

(2R)—N-[5-(1,3-benzodioxol-5-yl)-1-methyl-2-oxo-2,3-dihydro-1H-1,4-benzodiazepin-3-yl]-3-(3,4-difluorophenyl)-2-(4-fluorophenyl)propanamide Prepared analogously to example 158.
m/z (ES+) 572

Example 164

(2R,3R)-3-(3,4-difluorophenyl)-3-hydroxy-2-methyl-N-[1-methyl-2-oxo-5-(5oxo-5,6,7,8-tetrahydronaphthalen-2-yl)-2,3-dihydro-1H-1,4-benzodiazepin-3-yl]propanamide Prepared analogously to example 136.
m/z (ES+) 532

Example 165

(2R)-N-[5-(1,3-benzodioxol-5-yl)-1-methyl-2-oxo-2,3-dihydro-1H-1,4-benzodiazepin-3-yl]-3-(3,4-difluorophenyl)-2-(4-fluorophenyl)propanamide Prepared analogously to example 158.
m/z (ES+) 572

Example 166

(2R,3R)-3-(3,4-difluorophenyl)-2-(4-fluorophenyl)-3-hydroxy-N-{1-methyl-2-oxo-5-[4-(trifluoromethyl)piperidin-1-yl]-2,3-dihydro-1H-1,4-benzodiazepin-3-yl}propanamide Prepared by coupling of required benzodiazepine (c.f J. Med. Chem., 1994, 37, 719; Synthesis 1994, 505) under the conditions of Step 7E.
m/z (ES+) 619

Example 167

(2R,3R)-3-(3,4-difluorophenyl)-N-[5-(2,6-dimethylmorpholinzyl)-4-yl)-1-methyl-2-oxo-2,3-dihydro-1H-1,4-benzodiazepin-3-yl]-2-(4-fluorophenyl)-3-hydroxypropanamide Prepared by coupling of required benzodiazepine (c.f J. Med. Chem., 1994, 37, 719; Synthesis 1994, 505) under the conditions of Step 7E.
m/z (ES+) 581

Example 168

(2R,3R)-3-(3,4-difluorophenyl)-2-(4-fluorophenyl)-3-hydroxy-N-[1-methyl-2-oxo-5–2,4,6-trimethylpiperiden-1yl)-2,3-dihydro-1H-1,4-benzodiazepin-3-yl]propanamide Prepared by coupling of required benzodiazepine (c.f. J. Med. Chem., 1994, 37, 719; Synthesis 1994, 505) under the conditions of Step 7E.
m/z (ES+) 593

Example 169

(2R)-3-(3,4-difluorophenyl)-2-(4-fluorophenyl)-N-(5-isopropyl-2-oxo-2,3-dihydro-1H-1,4-benzodiazepin-3-yl)propanamide Prepared by reaction of 3-amino-5-isopropyl-2-oxo-phenyl-2,3-dihydro-1H-1,4benzodiazepine (prepared by methods analogous to R. G. Sherrill et al, J. Org. Chem., 1995, 60, 730) with (2R)-3-(3,4-difluorophenyl)-2-(4-fluorophenyl) propionic acid under reaction conditions 7E.
m/z (ES+) 480

Example 170

(2R,3R)-3-(3,4-dichlorophenyl)-2-(4-fluorophenyl)-3-hydroxy-N-(5-isopropyl-2-oxo-2,3-dihydro-1H-1,4-benzodiazepin-3yl)propanamide Prepared analogously to example 169.
m/z (ES+) 528

Example 171

(2S)—N-[5-(2,2-difluoro-1,3-benzodioxol-5-yl)-1-methyl-2-oxo-2,3-dihydro-1H-1,4-benzodiazepin-3-yl]-3-(3,4-difluorophenyl)-2methylpropanamide Prepared by reaction of the product from Step 7B (Scheme 7) with 5-boronyl-2,2-difluorobenzodioxole (prepared by treatment of 5-bromo-2,2-difluorobenzodioxole with bis(pinacolato)diboron under the reaction conditions described by N. Miyaura et al, J. Org. Chem., 1995, 60, 7508–7510) under reaction conditions 7C, followed by treatment with TFA (reaction 7D), followed by reaction with (2S)-2-methyl-3-(3,4-difluorophenyl)propionic acid under reaction conditions 7E to yield the title compound.
m/z (ES+) 528

Example 172

(2R,3R)—N-(5-tert-butyl-2-oxo-2,3-dihydro-1H-1,4-benzodiazepin-3-yl)-3-(3,4-difuorophenyl)-2-(4fluorophenyl)-3-hydroxypropanamide Prepared by coupling of 3-amino-2-oxo-5-tertbutyl-phenyl-2,3-dihydro-1H-1,4-benzodiazepine (prepared by methods analogous to R. G. Sherrill et al, J. Org. Chem., 1995, 60, 730) under reaction conditions 7E.
m/z (ES+) 510

Example 173

(2R)—N-[5-(1,3-benzodioxol-5-yl)-1-methyl-2-oxo-2,3-dihydro-1H-1,4benzofdiazepin-3-yl]-2-(2,5-difuorophenyl)-3-(3,4-difluorophenyl)propanamide Prepared analogously to example 158.
m/z (ES+) 590

Example 174

(2R,3R)-3-(3,4-difluorophenyl)-N-[5-(2,6-dimethylmorpholin-4-yl)-1methyl-2-oxo-2,3-dihydro-1H-1,4-benzodiazepin-3-yl]-2-(4-fluorophenyl)-3-hydroxypropanamide Prepared by coupling of required benzodiazepine (c.f. J. Med. Chem., 1994, 37, 719; Synthesis 1994, 505) under the conditions of Step 7E.
m/z (ES+) 581

Example 175

(2R,3R)-3-(3,4-difluorophenyl)-2-(4-fluorophenyl)-3-hydroxy-N-[1-methyl-5-(4methylpiperidin-1yl)-2-oxo-2,3-dihydro-1H-1,4-benzodiazepin-3-yl]propanamide Prepared by coupling of required benzodiazepine (c.f. *J. Med. Chem.*, 1994, 37, 719; *Synthesis* 1994, 505) under the conditions of Step 7E.

m/z (ES+) 565

Example 176

(2R,3R)-2-(4-fluorophenyl)-3-[3-fluoro-4-(trifluoromethyl)phenyl]-3-hydroxy-N-(5-isopropyl-2oxo-2,3-dihydro-1H-1,4-benzodiazepin-3-yl)propanamide Prepared analogously to example 169.

m/z (ES+) 546

Example 177

(2S)-N-(5-bicyclo[2.2.1]hept-1-yl-1-methyl-2-oxo-2,3-dihydro-1H-1,4-benzodiazepin-3-yl)-3-(3,4-difluorophenyl)-2-methylpropanamide Prepared by reaction of 3-amino-1-methyl-2-oxo-5-([2.2.1]-bicyclohept-1-yl)phenyl-2,3-dihydro-1H-1,4-benzodiazepine (prepared by methods analogous to R. G. Sherrill et al, *J. Org. Chem.*, 1995, 60, 730) with (2R)-3-(3,4-difluorophenyl)2-methylpropionic acid under reaction conditions 7E to yield the title compound.

m/z (ES+) 466

Example 178

(2R)-N-(5-cycloheptyl-2-oxo-2,3-dihydro-1H-1,4benzodiazepin-3-yl)-3-(3,4difluorophenyl)-2-(4-fluorophenyl)propanamide Prepared by reaction of 3-amino-2-oxo-5-(cycloheptyl)phenyl-2,3-dihydro-1H-1,4-benzodiazepine (prepared by methods analogous to R. G. Sherrill et al, *J. Org. Chem.*, 1995, 60, 730) with (2R)-3-(3,4-difluorophenyl)-2-(4-fluorophenyl)propionic acid under reaction conditions 7E to yield the title compound.

m/z (ES+) 534

Example 179

(2R,3R)-3(3,4-dichlorophenyl)-2-(4-fluorophenyl)-3-hydroxy-N-[(3S)-5-isopropyl-2-oxo-2,3-dihydro-1H-1,4-benzodiazepin-3-yl]propanamide Prepared analogously to example 169.

m/z (ES+) 528

Example 180

(2R,3R)-3-(3,4-dichlorophenyl)-2-(4-fluorophenyl)-3-hydroxy-N-(5-methyl-2-oxo-2,3-dihydro-1H-1,4-benzodiazepin-3-yl)propanamide Prepared by coupling of 3-amino-5-methyl-2-oxo-phenyl-2,3-dihydro-1H-1,4-benzodiazepine (prepared by methods analogous to R. G. Sherrill et al, *J. Org. Chem.*, 1995, 60, 730) under reaction conditions 7E.

m/z (ES+) 500

Example 181

(2S,3R)-3-(3,4-difluorophenyl)-2-(4-fluorophenyl)-N-[(3S)-5-isopropyl-2-oxo-2,3-dihydro-1H-1,4-benzodiazepin-3-yl]pent-4enamide Prepared by reaction of 3-amino-5-isopropyl-2-oxo-phenyl-2,3-dihydro-1H-1,4-benzodiazepine (prepared by methods analogous to R. G. Sherrill et al, *J. Org. Chem.*, 1995, 60, 730) with the product from Step 5B (Scheme 5) under reaction conditions 5C.

m/z (ES+) 506

Example 182

(2S)-3-(3,4-difluorophenyl)-N-(5-isopropyl-2-oxo-2,3-dihydro-1H-1,4-benzodiazepin-3-yl)-2-methylpropanamide Prepared analogously to example 169.

m/z (ES+) 400

Example 183

(2S,3R)-3-(3,4-difluorophenyl)-2-(4-fluorophenyl)-4-hydroxy-N-(5-isopropyl-2-oxo-2,3-dihydro-1H-1,4-benzodiazepin-3-yl)butanamide Prepared from the product described in example 181 by way of Step 5D (Scheme 5).

m/z (ES+) 510

Example 184

(2S,3R)-3-(3,4-difluorophenyl)-2-(4-fluorophenyl)-4-hydroxy-N-[5-(4-methoxyphenyl)-2-oxo-2,3-dihydro-1H-1,4-benzodiazepin-3-yl]butanamide Prepared by reaction of 3-amino-5-(4-methoxyphenyl)-2-oxo-phenyl-2,3-dihydro-1H-1,4-benzodiazepine (prepared by methods analogous to R. G. Sherrill et al, *J. Org. Chem.*, 1995, 60, 730) with the product from Step 5B under the conditions of Step 5C and 5D.

m/z (ES+) 574

Example 185

(2S,3R)-3-(3,4-difluorophenyl)-2-(4-fluorophenyl)-4-hydroxy-N-[1-isopropyl-5-(4-methoxyphenyl)-2-oxo-2,3-dihydro-1H-1,4-benzodiazepin-3-yl]butanamide Prepared by reaction of 3-amino-1-isopropyl-5-(4-methoxyphenyl)-2-oxo-phenyl-2,3-dihydro-1H-1,4-benzodiazepine (prepared by methods analogous to R. G. Sherrill et al, *J. Org. Chem.*, 1995, 60, 730) with the product from Step 5B under the conditions of Step 5C followed by oxidation under the conditions of Step 5D (Scheme 5).

m/z (ES+) 616

Example 186

(2R,3R)-N-(5-cyclobutyl-2-oxo-2,3-dihydro-1H-1,4-benzodiazepin-3-yl)-3-(3,4-dichlorophenyl)-2-(4-fluorophenyl)-3-hydroxypropanamide Prepared by coupling of 3-amino-5-cyclobutyl-2-oxo-phenyl-2,3-dihydro-1H-1,4-benzodiazepine (prepared by methods analogous to R. G. Sherrill et al, *J. Org. Chem.*, 1995, 60, 730) under reaction conditions 7E.

m/z (ES+) 540

Example 187

(2S,3R)-3-(3,4-difluorophenyl)-2-(4-fluorophenyl)-4-hydroxy-N-(5-(4-chlorophenyl)-2-oxo-2,3-dihydro-1H-1,4-benzodiazepin-3-yl)butanamide Prepared by reaction of 3-amino-1-isopropyl-5-(4-chlorophenyl)-2-oxo-phenyl-2,3-dihydro-1H-1,4-benzodiazepine (prepared by methods analogous to R. G. Sherrill et al, *J. Org. Chem.*, 1995, 60, 730) with the product from Step 5B under the conditions of Step 5C followed by oxidation under the conditions of Step 5D (Scheme 5).

m/z (ES+) 578

Unless otherwise indicated, Examples 188 to 216 were prepared as in Scheme 8 and/or Scheme 9.

Example 188

(2S)-3-(3,4-dichlorophenyl)-N-[1-(2-{[2-(dimethylamino)ethyl]ammo}-2-oxoethyl)-2-oxo-5-phenyl-2,3-dihydro-1H-1,4-benzodiazepin-3-yl]-2-methylpropanamide Prepared as shown in Scheme 9.

m/z (ES+) 594

Example 189

(2S)-3-(3,4dichlorophenyl)-2-methyl-N-(1-{2-[(2-morpholin-4-ylethyl)amino]-2-oxoethyl}-2-oxo-5-phenyl-2,3-dihydro-1H-1,4-benzodiazepin-3-yl)propanamide Prepared as shown in Scheme 9 using Step 9A then Step 9B (with 2-(morpholin-4-yl)-ethylamine).

m/z (ES+) 636

Example 190

(2R,3R)-N-[1-(2-amino-2-oxoethyl)-2-oxo-5-phenyl-2,3-dihydro-1H-1,4-benzodiazepin-3-yl]-3-(3,4-dichlorophenyl)-2-(4-fluorophenyl)-3-hydroxypropanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 619

Example 191

(2R,3R)-N-[1-(2-amino-2-oxoethyl)-5-isopropyl-2-oxo-2,3-dihydro-1H-1,4-benzodiazepin-3-yl]-3-(3,4-dichlorophenyl)-2-(4-fluorophenyl)-3-hydroxypropanamide Prepared by alkylation of 3-benzyloxycarbonylamino-5-isopropyl-2-oxo-phenyl-2,3-dihydro-1H-1,4-benzodiazepine (prepared by methods analogous to R. G. Sherrill et al, *J. Org. Chem.*, 1995, 60, 730) under reaction conditions 8F followed by 2D (Scheme 2) and 1E (Scheme 1).

m/z (ES+) 585

Example 192

(2R)-N-[1-(2-amino-2-oxoethyl)-2-oxo-5-phenyl-2,3-dihydro-1H-1,4-benzodiazepin-3-yl]-2-(2,5-difluorophenyl)-3-(3,4-difluorophenyl)propanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 589

Example 193

(2S)-N-[1-(2-amino-2-oxoethyl)-5-(2-methoxypyridin-4-yl)-2-oxo-2,3-dihydro-1H-1,4-benzodiazepin-3-yl]-3-(3,4-difluorophenyl)-2-methylpropanamide Prepared by alkylation of 3-benzyloxycarbonylamino-5-(2-methoxypyridin-4-yl)-2-oxo-phenyl-2,3-dihydro-1H-1,4-benzodiazepine (prepared by methods analogous to R. G. Sherrill et al, *J. Org. Chem.*, 1995, 60, 730) under reaction conditions 8F followed by 2D (Scheme 2) and 1E (Scheme 1).

m/z (ES+) 522

Example 194

(2R,3R)-N-[1-(2-amino-2-oxoethyl)-5-(4-methoxyphenyl)-2-oxo-2,3-dihydro-1H-1,4-benzodiazepin-3-yl]-3-(3,4-difluorophenyl)-2-(4-fluorophenyl)-3-hydroxypropanamide Prepared by alkylation of 3-benzyloxycarbonylamino-5-(4-methoxyphenyl)-2-oxo-phenyl-2,3-dihydro-1H-1,4-benzodiazepine (prepared by methods analogous to R. G. Sherrill et al, *J. Org. Chem.*, 1995, 60, 730) under reaction conditions 8F followed by 2D (Scheme 2) and 1E (Scheme 1).

m/z (ES+) 617

Example 195

(2S)-N-[1-(2-amino-2-oxoethyl)-5-(4-methoxyphenyl)-2-oxo-2,3-dihydro-1H-1,4-benzodiazepin-3-yl]-3-(3,4-difluorophenyl)-2-methylpropanamide Prepared analogously to example 194.

m/z (ES+) 521

Example 196

(2S)-N-[1-(2-amino-2-oxoethyl)-5-(4-chlorophenyl)-2-oxo-2,3-dihydro-1H-1,4-benzodiazepin-3-yl]-3-(3,4-difluorophenyl)-2-methylpropanamide Prepared by alkylation of 3-benzyloxycarbonylamino-5-(4-chlorophenyl)-2-oxo-phenyl-2,3-dihydro-1H-1,4-benzodiazepine (prepared by methods analogous to R. G. Sherrill et al, *J. Org. Chem.*, 1995, 60, 730) under reaction conditions 8F followed by 2D (Scheme 2) and 1E (Scheme 1).

m/z (ES+) 525

Example 197

(2R)-N-[1-(2-amino-2-oxoethyl)-2-oxo-5-phenyl-2,3-dihydro-1H-1,4-benzodiazepin-3-yl]-3-(3,4-difluorophenyl)-2-fluorophenyl)propanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 571

Example 198

(2S)-N-[1-(2-amino-2-oxoethyl)-5-(3,4-dichlorophenyl)-2-oxo-2,3-dihydro-1H-1,4-benzodiazepin-3-yl]-3-(3,4-difluorophenyl)-2-methylpropanamide Prepared by alkylation of 3-benzyloxycarbonylamino-5-(3,4-dichlorophenyl)-2-oxo-phenyl-2,3-dihydro-1H-1,4-benzodiazepine (prepared by methods analogous to R. G. Sherrill et al, *J. Org. Chem.*, 1995, 60, 730) under reaction conditions 8F followed by 2D (Scheme 2) and 1E (Scheme 1).

m/z (ES+) 559

Example 199

(2R)-N-[1-(2-amino-2-oxoethyl)-5-cycloheptyl-2-oxo-2,3-dihydro-1H-1,4-benzodiazepin-3-yl]-3-(3,4-difluorophenyl)-2-(4-fluorophenyl)propanamide Prepared from the product described in example 178 by alkylation using the procedure of Step 8F (Scheme 8).

m/z (ES+) 591

Example 200

(2R,3R)-N-[1-(2-amino-2-oxoethyl)-5-isopropyl-2-oxo-2,3-dihydro-1H-1,4-benzodiazepin-3-yl]-3-(3,4-dichlorophenyl)-2-(4-fluorophenyl)-3-hydroxypropanamide Prepared analogously to example 191.

m/z (ES+) 585

Example 201

(2R,3R)-3-(3,4-dichlorophenyl)-2-(4-fluorophenyl)-3-hydroxy-N-{5-isopropyl-1-[2-(methylamino)-2-oxoethyl]-2-oxo-2,3-dihydro-1H-1,4-benzodiazepin-3-yl}propanamide Prepared by alkylation of 3-benzyloxycarbonylamino-5-isopropyl-2-oxo-phenyl-2,3-dihydro-1H-1,4-benzodiazepine (prepared by methods analogous to R. G. Sherrill et al, *J. Org. Chem.*, 1995, 60, 730) under reaction conditions 9A followed by reaction with methylamine under the conditions of Step 9B then deprotection as Step 2D (Scheme 2) and finally coupling as shown in Step 1E (Scheme 1).

m/z (ES+) 599

Example 202

(2R,3R)-N-[1-(2-amino-2-oxoethyl)-5-isopropyl-2-oxo-2,3-dihydro-1H-1,4-benzodiazepin-3-yl]-2-(4-fluorophenyl)-3-[3-fluoro-4-(trifluoromethyl)phenyl]-3-hydroxypropanamide Prepared analogously to example 191.

m/z (ES+) 603

Example 203

(2R)-N-[1-(2-amino-2-oxoethyl)-2-oxo-5-phenyl-2,3-dihydro-1H-1,4-benzodiazepin-3-yl]-2-(4-fluorophenyl)-3-[3-fluoro-4-(trifluoromethyl)phenyl]propanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 621

Example 204

(2S)-N-[1-(2-amino-2-oxoethyl)-2-oxo-5-phenyl-2,3-dihydro-1H-1,4-benzodiazepin-3-yl]-3-(3,4-difluorophenyl)-2-methylpropanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 491

Example 205

(2R)-3-(3,4-difluorophenyl)-2-(4-fluorophenyl)-N-[2-oxo-5-phenyl-1-(pyridin-3-ylmethyl)-2,3-dihydro-1H-1,4-benzodiazepin-3-yl]propanamide Prepared from 3-benzyloxycarbonylamino-5-phenyl-2,3-dihydro-1H-1,4-benzodiazepin-2-one (*J. Org. Chem.* 1995, 60, 730) by way of alkylation with 3-(bromomethyl)pyridine under the conditions of Step 8F, followed by Steps 2D and 8I (Scheme 8).

m/z (ES+) 605

Example 206

(2S)-N-[1-(2-amino-2-oxoethyl)-5-(4-methoxyphenyl)-2-oxo-2,3-dihydro-1H-1,4-benzodiazepin-3-yl]-3-fluoro-4-(trifluoromethyl)phenyl]-2-methylpropanamide Prepared analogously to example 194.

m/z (ES+) 571

Example 207

(2S)-N-[1-(2-amino-2-oxoethyl)-5-isopropyl-2-oxo-2,3-dihydro-1H-1,4-benzodiazepin-3-yl]-3-(3,4-difluorophenyl)-2-methylpropanamide Prepared analogously to example 191.

m/z (ES+) 457

Example 208

(2R)N-[1-(2-amino-2-oxoethyl)-5-isopropyl-2-oxo-2,3-dihydro-1H-1,4-benzodiazepin-3-yl]-3-(3,4-difluorophenyl)-2-(4-fluorophenyl)propanamide Prepared analogously to example 191.

m/z (ES+) 537

Example 209

(2R)-N-[1-(2-amino-2-oxoethyl)-2-oxo-5-phenyl-2,3-dihydro-1H-1,4-benzodiazepin-3-yl]-3-(3,4-difluorophenyl)-2-(4-fluorophenyl)propanamide Prepared from 3-benzyloxycarbonylamino-5-phenyl-2,3-dihydro-1H-1,4-benzodiazepin-2-one (*J. Org. Chem.* 1995, 60, 730) by way of Steps 8F, 2D and 8I (Scheme 8).

m/z (ES+) 571

Example 210

(2R)-N-[1-(2-amino-2-oxoethyl)-5-(4-methoxyphenyl)-2-oxo-2,3-dihydro-1H-1,4-benzodiazepin-3-yl]-2-cyclopropyl-3-(3,4-difluorophenyl)propanamide Prepared analogously to example 194.

m/z (ES+) 547

Example 211

(2R)-N-[1-(2-amino-2-oxoethyl)-5-(4-methoxyphenyl)-2-oxo-2,3-dihydro-1H-1,4-benzodiazepin-3-yl]-2-(3,4-difluorobenzyl)-3-methylbutanamide Prepared analogously to example 194.
m/z (ES+) 549

Example 212

(2R)-3-(3,4-difluorophenyl)-2-(4-fluorophenyl)-N-[2-oxo-5-phenyl-1-(pyridin-4-ylmethyl)-2,3-dihydro-1H-1,4-benzodiazepin-3-yl]propanamide Prepared from 3-benzyloxycarbonylamino-5-phenyl-2,3-dihydro-1H-1,4-benzodiazepin-2one (J. Org. Chem. 1995, 60, 730) by way of alkylation with 4-(bromomethyl)pyridine under the conditions of Step 8F, followed by Steps 8H and 8I (Scheme 8).
m/z (ES+) 605

Example 213

(2S,3R)-N-[1-(2-amino-2-oxoethyl)-5-(4-methoxyphenyl)-2-oxo-2,3-dihydro-1H-1,4-benzodiazepin-3-yl]-3-(3,4-difluorophenyl)-2-(4-fluorophenyl)-4-hydroxybutanamide Prepared by alkylation of 3-benzyloxycarbonylamino-5-(4-methoxyphenyl)-2-oxo-phenyl-2,3-dihydro-1H-1,4-benzodiazepine (prepared by methods analogous to R. G. Sherrill et al, J. Org. Chem., 1995, 60, 730) under reaction conditions 8F followed by deprotection as in Step 2D (Scheme 2) and subsequent reaction with the product from Step 5B under the conditions of Step 5C. Final reaction under the conditions of Step 5D (Scheme 5) afforded the product.
m/z (ES+) 631

Example 214

(2R,3R)-N-[1-(2-amino-2-oxoethyl)-5-methyl-2-oxo-2,3-dihydro-1H-1,4-benzodiazepin-3-yl]-3-(3,4-dichlorophenyl)-2-(4-fluorophenyl)-3-hydroxypropanamide Prepared by alkylation of 3-benzyloxycarbonylamino-5-methyl-2-oxo-2,3-dihydro-1H-1,4-benzodiazepine (prepared by methods analogous to R. G. Sherrill et al, J. Org. Chem., 1995, 60, 730) under reaction conditions 8F followed by 2D (Scheme 2) and 1E (Scheme 1).
m/z (ES+) 557

Example 215

(2R)-N-[1-(3-amino-3-oxopropyl)-2-oxo-5-phenyl-2,3-dihydro-1H-1,4-benzodiazepin-3-yl]-3-(3,4-difluorophenyl)-2-(4-fluorophenyl)propanamide Prepared from 3-amino-5-phenyl-2,3-dihydro-1H-1,4-benzodiazepin-2-one (J. Org. Chem. 1995, 60, 730) by way of alkylation with 3-chloropropionamide under the conditions of Step 8F, followed by Steps 2D and 8I (Scheme 8).
m/z (ES+) 585

Example 216

(2R)-N-(3S)-[1-(2-amino-2-oxoethyl)-5-(4-methoxyphenyl)-2-oxo-2,3-dihydro-1H-1,4-benzodiazepin-3-yl]-2-cyclopropyl-3-(3,4-difluorophenyl)propanamide Prepared analogously to example 194.
m/z (ES+) 547

Unless otherwise indicated, Examples 217 to 273 were prepared using Schemes 7, 8, 9 or 10.

Example 217

(2R,3R)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-3-hydroxy-2-methylpropanamide Prepared by reaction of 3-benzyloxycarbonylamino-2-oxo-5–3,4-methylenedioxy)phenyl-2,3-dihydro-1H-1,4-benzodiazepine (prepared by methods analogous to R. G. Sherrill et al, J. Org. Chem., 1995, 60, 730) with iodoacetamide under reaction conditions 8F, followed by treatment with HBr—AcOH under reaction conditions 2D, followed by coupling under reaction conditions 7E to yield the title compound.
m/z (ES+) 551

Example 218

(2R)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-2-(4-fluorophenyl)propanamide Prepared analogously to example 217.
m/z (ES+) 615

Example 219

(2S)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-2-methylpropanamide Prepared analogously to example 217.
m/z (ES+) 535

Example 220

(2S)-N-[1-(2-amino-2-oxoethyl)-5-(1,3-benzodioxol-5-yl)-2-oxo-2,3-dihydro-1H-1,4-benzodiazepin-3-yl]-3-[3-fluoro-4-(trifluoromethyl)-phenyl]-2-methylpropanamide Prepared analogously to example 217.
m/z (ES+) 585

Example 221

Methyl (5-(1,3-benzodioxol-5-yl)-3-{[(2S)-3-(3,4-difluorophenyl)-2-methyl propanoyl]amino}-2-oxo-2,3-dihydro-1H-1,4-benzodiazepin-1-yl)acetate Prepared by reaction of 3-benzyloxycarbonylamino-2-oxo-5-(3,4-methylenedioxy)phenyl-2,3-dihydro-1H-1,4-benzodiazepine (prepared by methods analogous to R. G. Sherrill et al, J. Org. Chem., 1995, 60, 730) with methyl bromoacetate under reaction conditions 9A, followed by treatment with HBr—AcOH under reaction conditions 2D, followed by reaction with (2R)-2-methyl-3-(3,4-difluorophenyl)propionic acid under reaction conditions 7E.
m/z (ES+) 550

Example 222

(2S)-N-[5-(1,3-benzodioxol-5-yl)-1-(2-hydroxy-2-methylpropyl)-2-oxo-2,3-dihydro-1H-1,4-benzodiazepin-3-yl]-3-(3,4-difluorophenyl)-2-methylpropanamide A solution of 3-benzyloxycarbonylamino-2-oxo-5-(3,4-methylenedioxy)phenyl-2,3-dihydro-1H-1,4-benzodiazepine (1.0 g) (prepared by methods analogous to R. G. Sherrill et al, *J. Org. Chem.*, 1995, 60, 730) in DMF (20 ml) was treated at −15° C. with NaH (1.1 equivalents), stirred for 30 minutes and then treated with methallyl bromide (1.1 equivalents). The reaction mixture was allowed to warm to room temperature, and evaporated in vacuo. The residue was taken up in ethyl acetate-water, washed with water and brine, dried, filtered and evaporated. Purification by column chromatography gave the methallylated benzodiazepine (1.1 g, 98%).

A solution of the foregoing methallylated benzodiazepine was treated with HBr—AcOH under the reaction conditions 2D. Purification gave the tertiary bromide (0.85 g, 87%).

A solution of the foregoing tertiary bromide (200 mg) was treated with water (1.5 ml), acetone (1.5 ml) and silver nitrate (120 mg) and stirred overnight at room temperature. The reaction mixture was filtered through Celite®, washing with methanol. The filtrate was evaporated in vacuo, azeotroped with toluene and evaporated in vacuo. Purification by column chromatography gave the tertiary alcohol (102 mg, 59%).

A solution of the foregoing tertiary alcohol was reacted with (2R)-2-methyl-3-(3,4-difluorophenyl)propionic acid under reaction conditions 7E to yield the title compound.

m/z (ES+) 550

Example 223

(2S)-N-[5-(1,3-benzodioxol-5-yl)-2-oxo-1-(2-oxopropyl)-2,3-dihydro-1H-1,4-benzodiazepin-3-yl]-3-(3,4-difluorophenyl)-2-methylpropanamide A solution of the product described in example 221 (150 mg) in THF (5 ml) was cooled to −78° C. and treated with methyl magnesium bromide (3 equivalents) and allowed to warm to room temperature. The resulting complex reaction mixture was diluted with ethyl acetate and ammonium chloride. The organic layer was washed with brine, dried, filtered and evaporated in vacuo. Purification by chromatography gave the title compound (10 mg, 7%).

m/z (ES+) 534

Example 224

(2S)-N-[5-(1,3-benzodioxol-5-yl)-2-oxo-1-(2-oxo-2-pyrrolidin-1-ylethyl)-2,3-dihydro-1H-1,4-benzodiazepin-3-yl]-3-(3,4-difluorophenyl)-2-methylpropanamide Prepared by reaction of 3-benzyloxycarbonylamino-2-oxo-5-(3,4-methylenedioxy)phenyl-2,3-dihydro-1H-1,4-benzodiazepine (prepared by methods analogous to R. G. Sherrill et al, *J. Org. Chem.*, 1995, 60, 730) with methyl bromoacetate under reaction conditions 9A. This product was treated with pyrrolidine (1 ml) and heated at 50° C. for 3 h. The reaction mixture was evaporated in vacuo and purified by column chromatography to give the corresponding amide (165 mg, 77%)

The foregoing amide was treated with HBr—AcOH following reaction conditions 2D and the resulting product was reacted with (2R)-2-methyl-3-(3,4-difluorophenyl)propionic acid under reaction conditions 7E to yield the title compound.

m/z (ES+) 589

Example 225

2-(5-(1,3-benzodioxol-5-yl)-3-{[(2S)-3-(3,4-difluorophenyl)-2-methylpropanoyl]amino}-2-oxo-2,3-dihydro-1H-1,4-benzodiazepin-1-yl)ethyl acetate Prepared analogously to example 221, except that 2-bromoethyl acetate was used in Step 9A.

m/z (ES+) 564

Example 226

(2S)-N-[5-(1,3-benzodioxol-5-yl)-1-(2-hydroxyethyl)-2-oxo-2,3-dihydro-1H-1,4-benzodiazepin-3-yl]-3-(3,4-difluorophenyl)-2-methylpropanamide A solution of the product described in example 225 (250 mg) was dissolved in dioxane (3 ml) and aqueous lithium hydroxide solution (0.5 ml) and stirred at room temperature for 2 h. The reaction mixture was diluted with ammonium chloride and ethyl acetate, washed with brine, dried, filtered and evaporated. Purification by column chromatography gave the title compound (111 mg, 48%).

m/z (ES+) 522

Example 227

(2S)-N-{5-(1,3-benzodioxol-5-yl)-1-[2-(methylamino)-2-oxoethyl]-2-oxo-2,3-dihydro-1H-1,4-benzodiazepin-3-yl}-3-(3,4-difluorophenyl)-2-methylpropanamide Prepared as shown in Scheme 10.

m/z (ES+) 549

Example 228

(2R)-N-[5-(1,3-benzodioxol-5-yl)-1-(2-hydroxy-2-methylpropyl)-2-oxo-2,3-dihydro-1H-1,4-benzodiazepin-3-yl]-3-(3,4-difluorophenyl)-2-(4-fluorophenyl)propanamide Prepared analogously to example 222.

m/z (ES+) 630

Example 229

(2S)-N-[5-(1,3-benzodioxol-5-yl)-1-(2-bromo-2-methylpropyl)-2-oxo-2,3-dihydro-1H-1,4-benzodiazepin-3-yl]-3-(3,4-difluorophenyl)-2-methylpropanamide Prepared analogously to example 222 except the silver nitrate step was ommitted.

m/z (ES+) 613

Example 230

(2S)-N-{5-(1,3-benzodioxol-5-yl)-1-[2-(dimethylamino)-2-oxoethyl]-2-oxo-2,3-dihydro-1–1,4-benzodiazepin-3-yl}-3-(3,4-difluorophenyl)-2-methylpropanamide Prepared as shown in Scheme 10; Step 10B was carried out using dimethylamine.

m/z (ES+) 563

Example 231

(2S)-N-[5-(1,3-benzodioxol-5-yl)-1-(2-morpholin-4-yl-2-oxoethyl)-2-oxo-2,3-dihydro-1H-1,4-benzodiazepin-3-yl]-3-(3,4-difluorophenyl)-2-methylpropanamide Prepared as shown in Scheme 10; Step 10B was carried out using morpholine.
m/z (ES+) 605

Example 232

(2S)-N-{5-(1,3-benzodioxol-5-yl)-1-[2-(isopropylamino)-2-oxoethyl]-2-oxo-2,3-dihydro-1H-1,4-benzodiazepin-3-yl}-3-(3,4-difluorophenyl)-2-methylpropanamide Prepared analogously to example 224 except that isopropylamine was used in place of pyrrolidine.
m/z (ES+) 577

Example 233

(2S)-N-{5-(1,3-benzodioxol-5-yl)-1-[2-(ethylamino)-2-oxoethyl]-2-oxo-2,3-dihydro-1H-1,4-benzodiazepin-3-yl}-3-(3,4-difluorophenyl)-2-methylpropanamide Prepared analogously to example 224 except that ethylamine was used in place of pyrrolidine.
m/z (ES+) 563

Example 234

(2S)-N-{5-(1,3-benzodioxol-5-yl)-1-[2-(tert-butylamino)-2-oxoethyl]-2-oxo-2,3-dihydro-1,4-benzodiazepin-3-yl}-3-(3,4-difluorophenyl)-2-methylpropanamide Prepared by reaction of 3-benzyloxycarbonylamino-2-oxo-5-(3,4-methylenedioxy)phenyl-2,3-dihydro-1H-1,4-benzodiazepine (prepared by methods analogous to R. G. Sherrill et al, *J. Org. Chem.*, 1995, 60, 730) with methyl bromoacetate under reaction conditions 9A. This product (501 mg) was dissolved in dioxane (10 ml), treated with aqueous lithium hydroxide (10 equivalents) and stirred at room temperature. The resulting reaction mixture was acidified with citric acid, diluted with ethyl acetate and washed with brine, dried, filtered and evaporated in vacuo. The foregoing acid was dissolved in THF (15 ml) and DMF (1 drop) and treated with oxalyl chloride (1.5 equiv) and stirred for 1 h. The resulting acid chloride was treated with tert-butylamine (5 equivalents) at 0° C., stirred for 30 minutes, diluted with ethyl acetate and washed with citric acid, NaHCO$_3$ and brine and dried, filtered and evaporated in vacuo. Purification by column chromatography gave the corresponding tert-butyl amide (250 mg, 48%).

The foregoing amide was treated with HBr—AcOH following reaction conditions 2D and the resulting product was reacted with (2R)-2-methyl-3-(3,4-difluorophenyl)propionic acid under reaction conditions 7E to yield the title compound.
m/z (ES+) 591

Example 235

(2S,3S)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-2-(4-fluorophenyl)-3-hydroxypropanamide Prepared analogously to example 217.
m/z (ES+) 631

Example 236

(2S,3S)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-3-hydroxy-2-methylpropanamide Prepared analogously to example 217.
m/z (ES+) 551

Example 237

(2R,3R)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-2-(4-fluorophenyl)-3-hydroxypropanamide Prepared analogously to example 217.
m/z (ES+) 631

Example 238

(2R)-N-[1-(2-amino-2-oxoethyl)-5-(1,3-benzodioxol-5-yl)-2-oxo-2,3-dihydro-1H-1,4-benzodiazepin-3-yl]-3-(3,4-difluorophenyl)-2-methylpropanamide Prepared analogously to example 217.
m/z (ES+) 535

Example 239

N-[1-(2-amino-2-oxoethyl)-5-(1,3-benzodioxol-5-yl)-2-oxo-2,3-dihydro-1H-1,4-benzodiazepin-3-yl]-2-benzyl-3,3,3-trifluoropropanamide (less polar isomer)

Prepared analogously to example 217, except that 2-benzyl-3,3,3-trifluoropropanoic acid (Watanabe, Shoji et al, *J. Fluorine Chem.* (1992), 59(2), 249–56) was used in Step 7E.
m/z (ES+) 553

Example 240

N-[1-(2-amino-2-oxoethyl)-5-(1,3-benzodioxol-5-yl)-2-oxo-2,3-dihydro-1H-1,4-benzodiazepin-3-yl]-2-benzyl-3,3,3-trifluoropropanamide (more polar isomer)

Prepared analogously to example 239.
m/z (ES+) 553

Example 241

(2S)-N-[5-(1,3-benzodioxol-5-yl)-1-(cyanomethyl)-2-oxo-2,3-dihydro-1H-1,4-benzodiazepin-3-yl]-3-(3,4-difluorophenyl)-2-methylpropanamide Prepared by reaction of the product described in example 162 with bromoacetonitrile under the reaction conditions 8F.
m/z (ES+) 517

Example 242

(2S)-N-[1-(2-amino-2-oxoethyl)-5-(3-chloro-4-methoxyphenyl)-2-oxo-2,3-dihydro-1H-1,4-benzodiazepin-3-yl]-3-(3,4-difluorophenyl)-2-methylpropanamide Prepared using procedures 8A–8G and 8H–8I shown in Scheme 8. (3-chloro-4-methoxyphenylboronic acid was used in Step 8G).
m/z (ES+) 555

Example 243

(2R)-N-[1-(2-amino-2-oxoethyl)-5-(1,3-benzodioxol-5-yl)-2-oxo-2,3-dihydro-1H-1,4-benzodiazepin-3-yl]-2-(3,4-difluorophenoxy)propanamide Prepared analogously to example 217. The requisite carboxylic acid as prepared using the method of *J. Org. Chem.*, 1993, 58, 1276.
m/z (ES+) 537

Example 244

(2S)-N-[5-(1,3-benzodioxol-5-yl)-1-(2-hydroxy-2-methylpropyl)-2-oxo-2,3-dihydro-1H-1,4-benzodiazepin-3-yl]-3-[3-fluoro-4-(trifluoromethyl)phenyl]-2-methylpropanamide Prepared analogously to example 222.
m/z (ES+) 600

Example 245

(2S)-N-[1-(2-amino-2-oxoethyl)-5-(1,3-benzodioxol-5-yl)-2-oxo-2,3-dihydro-1H-1,4-benzodiazepin-3-yl]-2-methyl-3-[4-(trifluoromethyl)phenyl]propanamide Prepared analogously to example 217.
m/z (ES+) 567

Example 246

(2S)-N-[1-(2-amino-2-oxoethyl)-5-(1,3-benzodioxol-5-yl)-2-oxo-2,3-dihydro-1H-1,4-benzodiazepin-3-yl]-3-[4-fluoro-3-(trifluoromethyl)phenyl]-2-methylpropanamide Prepared analogously to example 217.
m/z (ES+) 585

Example 247

(2S)-N-[1-(2-amino-2-oxoethyl)-5-(2,3-dihydro-1,4-benzodioxin-6-yl)-2-oxo-2,3-dihydro-1H-1,4-benzodiazepin-3-yl]-3-(3,4-difluorophenyl)-2-methylpropanamide Prepared using procedures 8A–8G and 8H–8I shown in Scheme 8. (Step 8G using 6-boronyl-2,3-dihydro-1,4-benzodioxane (prepared by treatment of 6-bromo-2,3-dihydro-1,4-benzodioxane with bis(pinacolato)diboron under the reaction conditions described by N. Miyaura et al, *J. Org. Chem.*, 1995, 60, 7508–7510)).
m/z (ES+) 549

Example 248

(2S)-N-[1-(2-amino-2-oxoethyl)-5-(1,3-benzodioxol-5-yl)-2-oxo-2,3-dihydro-1H-1,4-benzodiazepin-3-yl]-2-(3,4-difluorobenzyl)pent-4-enamide Prepared analogously to example 217.
m/z (ES+) 561

Example 249

(2S)-N-[5-(2,2-difluoro-1,3-benzodioxol-5-yl)-1-(4-methoxybenzyl)-2-oxo-2,3-dihydro-1H-1,4-benzodiazepin-3-yl]-3-[3-fluoro-4-trifluoromethyl)phenyl]-2-methylpropanamide Prepared analogously to example 242 except Steps 8E and 8F were omitted. (Step 8G used 5-boronyl-2,2-difluoro-1,3-benzodioxane (prepared by treatment of 5-bromo-2,2-difluoro-1,3-benzodioxane with bis(pinacolato)diboron under the reaction conditions described by N. Miyaura et al, *J. Org. Chem.*, 1995, 60, 7508–7510)).
m/z (ES+) 684

Example 250

(2S)-N-[1-(2-amino-2-oxoethyl)-5-(2,2-difluoro-1,3-benzodioxol-5-yl)-2-oxo-2,3-dihydro-1H-1,4-benzodiazepin-3-yl]-3-[3-fluoro-4-(trifluoromethyl)phenyl]-2-methylpropanamide Prepared analogously to example 242. (Step 8G used 5-boronyl-2,2-difluoro-1,3-benzodioxane (prepared by treatment of 5-bromo-2,2-difluoro-1,3-benzodioxane with bis(pinacolato)diboron under the reaction conditions described by N. Miyaura et al, *J. Org. Chem.*, 1995, 60, 7508–7510))
m/z (ES+) 621

Example 251

(2S)-N-[1-(2-amino-2-oxoethyl)-2-oxo-5-pyridin-4-yl-2,3-dihydro-1H-1,4-benzodiazepin-3-yl]-3-[3-fluoro-4-(trifluoromethyl)phenyl]-2-methylpropanamide Prepared analogously to example 242 (Step 8G used 4-pyridyl boronic acid)
m/z (ES+) 542

Example 252

(2S)-N-[1-(2-amino-2-oxoethyl)-5-(1,3-benzodioxol-5-yl)-2-oxo-2,3-dihydro-1H-1,4-benzodiazepin-3-yl]-2-methyl-3-[3-(trifluoromethyl)phenyl]propanamide Prepared analogously to example 217.
m/z (ES+) 567

Example 253

(2S)-N-[1-(2-amino-2-oxoethyl)-5-(1,3-benzodioxol-5-yl)-2-oxo-2,3-dihydro-1H-1,4-benzodiazepin-3-yl]-2-methyl-3-[2-(trifluoromethyl)phenyl]propanamide Prepared analogously to example 217.
m/z (ES+) 567

Example 254

(2S)-N-[1-(2-amino-2-oxoethyl)-5-(1,3-benzodioxol-5-yl)-2-oxo-2,3-dihydro-1H-1,4-benzodiazepin-3-yl]-2-methyl-3-phenylpropanamide Prepared analogously to example 217.
m/z (ES+) 499

Example 255

(2S)-N-[5-(2,6-dimethylmorpholin-4-yl)-2-oxo-2,3-dihydro-1H-1,4-benzodiazepin-3-yl]-3-[3-fluoro-4-(trifluoromethyl)phenyl]-2-methylpropanamide Prepared using procedures shown in Scheme 8 in the order: 8A–8D, 8J, 8H–8I, 8E.
m/z (ES+) 521

Example 256

(2S)-N-[1-(2-amino-2-oxoethyl)-5-(2,6-dimethylmorpholin-4-yl)-2-oxo-2,3-dihydro-1H-1,4-benzodiazepin-3-yl]-3-[3-fluoro-4-(trifluoromethyl)phenyl]-2-methylpropanamide Prepared from the product from example 255 by application of Step 8F.
m/z (ES+) 578

Example 257

(2S)-N-[1-(2-amino-2-oxoethyl)-5-morpholin-4-yl-2-oxo-2,3-dihydro-1H-1,4-benzodiazepin-3-yl]-3-[3-fluoro-4-(trifluoromethyl)phenyl]-2-methylpropanamide Prepared using procedures shown in Scheme 8 in the order: 8A–8F 8J, 8H–8I.
m/z (ES+) 550

Example 258

(2R)-N-[1-(2-amino-2-oxoethyl)-(1,3-benzodioxol-5-yl)-2-oxo-2,3-dihydro-1H-1,4-benzodiazepin-3-yl]-2-(3,4-difluorobenzyl)-3-methylbutanamide Prepared analogously to example 217.
m/z (ES+) 563

Example 259

(2R)-N-[1-(2-amino-2-oxoethyl)-5-morpholin-4-yl-2-oxo-2,3-dihydro-1H-1,4-benzodiazepin-3-yl]-3-(3,4-difluorophenyl)-2-(4-fluorophenyl)propanamide Prepared analogously to example 257.
m/z (ES+) 580

Example 260

(2R)-N-[1-(2-amino-2-oxoethyl)-2-oxo-5-pyridin-4-yl-2,3-dihydro-1H-1,4-benzodiazepin-3-yl]-3-(3,4-difluorophenyl)-2-(4-fluorophenyl)propanamide Prepared analogously to example 251
m/z (ES+) 572

Example 261

(2S)-N-[1-(2-amino-2-oxoethyl)-2-oxo-5-quinolin-6-yl-2,3-dihydro-1H-1,4-benzodiazepin-3-yl]-3-(3,4-difluorophenyl)-2-methylpropanamide Prepared using procedures 8A–8G and 8H–8I shown in Scheme 8. (Step 8G used 6-boronylquinoline(prepared by treatment of 6-bromoquinoline with bis(pinacolato)diboron under the reaction conditions described by N. Miyaura et al, J. Org. Chem., 1995, 60, 7508–7510)).
m/z (ES+) 542

Example 262

(2S)-N-[1-(2-amino-2-oxoethyl)-2-oxo-5-pyridin-4-yl-2,3-dihydro-1H-1,4-benzodiazepin-3-yl]-3-(3,4-difluorophenyl)-2-(4-fluorophenyl)propanamide Prepared analogously to example 242. (Step 8G used 4-pyridyl boronic acid.)
m/z (ES+) 572.

Example 263

(2S)-N-{1-[2-(methylamino)-2-oxoethyl]-2-oxo-5-phenyl-2,3-dihydro-1H-1,4-benzodiazepin-3-yl}-3-(3,4-difluorophenyl)-2-(4-fluorophenyl)propanamide Prepared from 3-benzyloxycarbonylamino-5-phenyl-2,3-dihydro-1H-1,4-benzodiazepin-2-one (J. Org. Chem. 1995, 60, 730) by way of Steps 10A, 10B and 10C (Scheme 10).
m/z (ES+) 585

Example 264

(2S)-N-{1-[2-(dimethylamino)-2-oxoethyl]-2-oxo-5-phenyl-2,3-dihydro-1H-1,4-benzodiazepin-3-yl}-3-(3,4-difluorophenyl)-2–4-fluorophenyl)propanamide Prepared from 3-benzyloxycarbonylamino-5-phenyl-2,3-dihydro-1H-1,4-benzodiazepin-2-one (J. Org. Chem. 1995, 60, 730) by way of Steps 10A, 10B (using dimethylamine in place of methylamine) and 10C (Scheme 10).
m/z (ES+) 599

Example 265

(2S,3R)-3-(3,4-difluorophenyl)-2-(4-fluorophenyl)-4-hydroxy-N-[1-(2-amino-2-oxoethyl)-2-oxo-5-phenyl-2,3-dihydro-1H-1,4-benzodiazepin-3-yl]butanamide Prepared from 3-benzyloxycarbonylamino-5-phenyl-2,3-dihydro-1H-1,4-benzodiazepin-2-one (J. Org. Chem. 1995, 60, 730) by way of Steps 8F, 2D followed by coupling with the product from Step 5B under the conditions of Step 5C and finally treatment under the conditions of Step 5D.
m/z (ES+) 601

Example 266

(2S,3R)-3-(3,4-difluorophenyl)-2-(4-fluorophenyl)-4-hydroxy-N-[2-oxo-5-(4-pyridyl)-2,3-dihydro-1H-1,4-benzodiazepin-3-yl]butanamide Prepared using procedures shown in Scheme 8 in the order: 8A–8E, 8G–8H followed by coupling under the condition of Step 8I with the product from Step 5B and finally treatment under the conditions of Step 5D.
m/z (ES+) 545

Example 267

(2S)-N-[1-(2-amino-2-oxoethyl)-2-oxo-5-phenyl-2,3-dihydro-1H-1,4-benzodiazepin-3-yl]-2-(4-fluorophenyl)-3-(3,4-difluorophenyl)propanamide Prepared from 3-benzyloxycarbonylamino-5-phenyl-2,3-dihydro-1H-1,4-benzodiazepin-2-one (J. Org. Chem. 1995, 60, 730) by way of Steps 8F, 2D and 8I (Scheme 8).
m/z (ES+) 571

Example 268

(2S)-N-{1-[3-(morpholin-4-yl)propyl]-2-oxo-5-phenyl-2,3-dihydro-1H-1,4-benzodiazepin-3-yl}-2-(4-fluorophenyl)-3-(3,4-difluorophenyl)propanamide Prepared from 3-tertbutyloxycarbonylamino-5-phenyl-2,3-dihydro-1H-1,4-benzodiazepin-2-one (c.f. *J. Org. Chem.*

1995, 60, 730) by way of Step 10A using 1,3-dibromopropane, 10B using morpholine/DMF, Step 8H and finally Step 1E.

m/z (ES+) 691

Example 269

(2S)-N-[1-(2-amino-2-oxoethyl)-5-(2,6-dimethylmorpholin-4-yl)-2-oxo-2,3-dihydro-1H-1,4-benzodiazepin-3-yl]-3-(3,4-difluorophenyl)-2-(4-fluorophenyl)propanamide Prepared using procedures shown in Scheme 8 in the order: 8A–8D, 8J, 8H–8I, 8E, 8F.

m/z (ES+) 580

Example 270

(2S,3R)-3-(3,4-difluorophenyl)-2-(4-fluorophenyl)-4-hydroxy-N-[5-(2,6-dimethylmorpholin-4-yl)-2-oxo-2,3-dihydro-1H-1,4-benzodiazepin-3-yl]butanamide Prepared using procedures shown in Scheme 8 in the order: 8A–8E, 8J, 8H followed by coupling under the condition of Step 8I with the product from Step 5B and finally treatment under the conditions of Step 5D.

m/z (ES+) 581

Example 271

(2S,3R)-3-(3,4-difluorophenyl)-2-(4-fluorophenyl)-4-hydroxy-N-[5-cyclobutyl-2-oxo-2,3-dihydro-1H-1,4-benzodiazepin-3-yl]butanamide Prepared by coupling of 3-amino-5-cyclobutyl-2-oxo-phenyl-2,3-dihydro-1H-1,4-benzodiazepine (prepared by methods analogous to R. G. Sherrill et al, *J. Org. Chem.*, 1995, 60, 730) with the product from Step 5B under the conditions of Step 5C and finally treatment under the conditions of Step 5D.

m/z (ES+) 522

Example 272

(2S,3R)-3-(3,4-difluorophenyl)-2-(4-fluorophenyl)-4-hydroxy-N-[5-cyclopropyl-2-oxo-2,3-dihydro-1H-1,4-benzodiazepin-3-yl]butanamide Prepared by coupling of 3-amino-5-cyclopropyl-2-oxo-phenyl-2,3-dihydro-1H-1,4-benzodiazepine (prepared by methods analogous to R. G. Sherrill et al, *J. Org. Chem.*, 1995, 60, 730) with the product from Step 5B under the conditions of Step 5C and finally treatment under the conditions of Step 5D.

m/z (ES+) 508

Example 273

(2S,3R)-3-(3,4-difluorophenyl)-2-(4-fluorophenyl)-4-hydroxy-N-[2,4-dioxo-2,3,4,5-tetrahydro-1H-1,5-benzodiazepin-3-yl]butanamide Prepared by coupling of 3-amino-2,4dioxo-2,3,4,5-tetrahydro-1H-1,5-benzodiazepine (prepared by methods disclosed in WO96/40655) with the product from Step 5B under the conditions of Step 5C and finally treatment under the conditions of Step 5D.

m/z (ES+) 568

What is claimed is:

1. A compound of formula I:

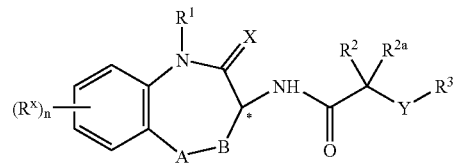

wherein:

n is 0–3;

each $R^x$ independently represents halogen, —CN, —$NO_2$, $C_{1-6}$alkyl, polyfluoro$C_{1-6}$alkyl, —OH or $C_{1-4}$alkoxy;

-A-B- represents:

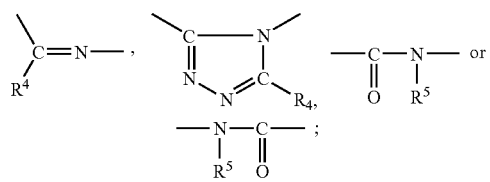

X represents O, S or N—$R^a$ where $R^a$ together with $R^1$ completes a fused imidazole or 4,5-dihydroimidazole ring;

Y represents —CH($R^b$)—, —$(CH_2)_x$—CH($OR^c$)—, —CH($CH_2OCOR^b$)—, —CH(NHC(O)$R^b$)—, —$(CH_2)_x$—C(O)—, —$(CH_2)_x$—C(NO$R^b$)—, —CH($OSO_2NH_2$)—, —O— or —S—; where x is 0 or 1, $R^b$ represents H or $C_{1-6}$alkyl or $C_{2-6}$alkenyl, either of which is optionally substituted with halogen, CN, $NO_2$, $CF_3$, OH, $CO_2H$, $C_{1-4}$alkoxy or $C_{1-4}$alkoxycarbonyl, and $R^c$ represents $R^b$ or tris($C_{1-6}$alkyl)silyl;

$R^1$ represents H, $C_{1-6}$alkyl, $C_{3-8}$cycloalkyl, $C_{2-6}$alkenyl, $C_{2-6}$alkynyl or polyfluoro$C_{1-6}$alkyl, said alkyl, cycloalkyl, alkenyl and alkynyl groups being optionally substituted by halogen, —CN, —$NO_2$, aryl, heteroaryl, —$COR^6$, —$CO_2R^6$, —$CON(R^6)_2$, —$OCOR^7$, —$NR^6COR^7$, —$NR^6SO_2R^7$, —$SO_3R^6$, —$SO_2N(R^6)_2$, —$OR^6$, —$SR^6$ or —$N(R^6)_2$; when X is N—$R^a$, $R^1$ together with $R^a$ completes a fused imidazole or 4,5-dihydroimidazole ring;

$R^2$ represents $C_{1-6}$alkyl, $C_{3-6}$cycloalkyl, $C_{2-6}$alkenyl, $C_{2-6}$alkynyl, polyfluoro$C_{1-6}$alkyl, aryl, heteroaryl, —$OR^7$ or —Oaryl, said alkyl, cycloalkyl, alkenyl and alkynyl groups optionally being substituted by halogen, —CN, —$NO_2$, aryl, heteroaryl, —$COR^6$, —$CO_2R^6$, —$CON(R^6)_2$, —$OCOR^7$, —$NR^6COR^7$, —$NR^6SO_2R^7$, —$S_3R^6$, —$SO_2N(R^6)_2$, —$OR^6$, —$SR^6$ or —$N(R^6)_2$;

$R^{2a}$ represents H or $C_{1-6}$alkyl;

or $R^2$ and $R^{2a}$ together complete a $C_{3-6}$cycloalkyl group;

$R^3$ represents aryl or heteroaryl;

$R^4$ represents H, halogen, —CN, $C_{1-10}$alkyl, $C_{3-10}$cycloalkyl, $C_{2-10}$alkenyl, $C_{2-10}$alkynyl, aryl, heteroaryl, —$OR_8$ or —$N(R^8)_2$, said alkyl, cycloalkyl, alkenyl and alkynyl groups optionally being substituted by halogen, —CN, —$NO_2$, aryl, heteroaryl, —$COR^6$, —$CO_2R^6$, —$CON(R^6)_2$, —$OCOR^7$, —$NR^6COR^7$, —$NR^6SO_2R^7$, —$SO_3R^6$, —$SO_2N(R^6)_2$, —$OR^6$, —$SR^6$ or —$N(R^6)_2$;

$R^5$ represents H, $C_{1-6}$alkyl or benzyl which optionally bears up to 3 substituents independently selected from halogen, —CN, —NO$_2$, —OH and methoxy;

each $R^6$ independently represents H, polyfluoroC$_{1-6}$alkyl, or $C_{1-6}$alkyl which is optionally substituted with halogen, —CN, —NO$_2$, —OH, —SH, —NH$_2$, phenyl, morpholin-4-yl, thiomorpholin-4-yl, piperidin-1-yl, piperazin-1-yl, pyrrolidin-1-yl, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$; or two $R_6$ groups attached to a single nitrogen atom may complete a heterocyclic ring or condensed ring system of from 3 to 12 members including the said nitrogen, the remaining atoms being selected from C, N, O and S, and the ring or condensed ring system optionally bearing up to 3 substituents independently selected from $C_{1-6}$alkyl, polyfluoroC$_{1-6}$alkyl, $C_{2-7}$acyl, —OH and —CONH$_2$;

$R^7$ represents $R^6$ that is other than H;

$R^8$ represents $R^6$, aryl or heteroaryl;

$R^9$ represents aryl, heteroaryl, $C_{3-6}$cycloalkyl or —OR$^7$;

"aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoroC$_{1-6}$alkyl, halogen, —CN, —NO$_2$, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

"heteroaryl" refers to a heteroaromatic ring of 5 or 6 members, at least one member being nitrogen, oxygen or sulphur and the remainder carbon, said ring optionally being fused to a 5–7 membered saturated or unsaturated ring which may be carbocyclic or may comprise up to 3 heteroatoms selected from nitrogen, oxygen and sulphur, and which may be oxo-substituted, the heteroaromatic ring and optional fused ring together bearing 0–3 substituents independently selected from $C_{1-6}$alkyl which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONH C$_{1-4}$alkyl or —CON(C$_{1-4}$alkyl)$_2$, polyfluoroC$_{1-6}$alkyl, halogen, —CN, —NO$_2$, phenyl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

or a pharmaceutically acceptable salt thereof.

2. A compound according to claim 1 of formula II:

or a pharmaceutically acceptable salt thereof.

3. A compound according to claim 2 of formula IIa:

wherein:

$R^y$, $R^z$, $R^v$ and $R^w$ are independently H, CF$_3$ or halogen;

$Y^1$ is —CH(R$^b$)—, —CH(OR$^c$)—, —CH(CH$_2$OCOR$^b$)—, —CH(NHC(O)R$^b$)—, —C(O)—, —C(NOR$^b$)— or —O—;

$R^{1a}$ is H, polyfluoroC$_{1-4}$alkyl, or $C_{1-4}$alkyl which is optionally substituted by —OH, —CN, halogen, aryl, heteroaryl, carbamoyl, N-($C_{1-4}$alkyl)carbamoyl, N,N-di($C_{1-4}$alkyl)carbamoyl or dimethylamino;

$R^{2b}$ is selected from $C_{1-6}$alkyl, $C_{3-6}$cycloalkyl, polyfluoroC$_{1-6}$alkyl, (R$^{6a}$)$_2$N—$C_{1-6}$alkyl, $C_{2-6}$alkenyl, heteroaryl, $C_{1-6}$alkoxy, —N(R$^{6a}$)$_2$, —NHCO$_2$R$^{7a}$, and phenyl which is optionally substituted by halogen;

$R^{4a}$ is selected from $C_{1-10}$alkyl, $C_{3-10}$cycloalkyl, —N(R$^{6a}$)$_2$, pyridyl which is optionally substituted by methoxy; or phenyl which is optionally substituted by up to 2 groups selected from halogen, methoxy, CF$_3$, OCF$_3$ and carbamoyl or which is fused to a heterocyclic ring or to an oxo-substituted carbocyclic ring;

each $R^{6a}$ independently represents H or $C_{1-6}$alkyl which is optionally substituted with —CONH$_2$, or two $R^{6a}$ groups together with a nitrogen atom to which they are commonly attached complete a heterocyclic ring or condensed ring system of 3–12 members including the said nitrogen, the remaining atoms being selected from C, O, N and S, and the ring or condensed ring system optionally bearing up to 3 substituents selected from $C_{1-4}$alkyl, polyfluoroC$_{1-6}$alkyl, —OH, and —CONH$_2$; and $R^{7a}$ represents t-butyl or benzyl;

or a pharmaceutically acceptable salt thereof.

4. A compound according to claim 1 of formula IIc:

or a pharmaceutically acceptable salt thereof.

5. A compound according to claim 4 of formula IId:

where $R^y$, $R^z$, $R^v$, $R^w$, $Y^1$, $R^{1a}$ and $R^{2b}$ are as defined in claim 3;
or a pharmaceutically acceptable salt thereof.

6. A method of treatment of a subject suffering from Alzheimer's disease which comprises administering to that subject an effective amount of a compound of formula I

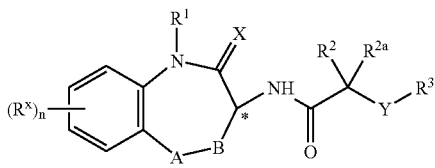

I wherein:

n is 0–3;

each $R^x$ independently represents halogen, —CN, —NO$_2$, $C_{1-6}$alkyl, polyfluoro$C_{1-6}$alkyl, —OH or $C_{1-4}$alkoxy;

-A-B- represents:

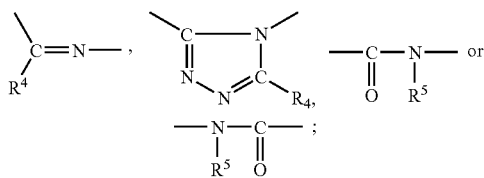

X represents O, S or N—$R^a$ where $R^a$ together with $R^1$ completes a fused imidazole or 4,5-dihydroimidazole ring;

Y represents —CH($R^b$)—, —(CH$_2$)$_x$—CH(OR$^c$)—, —CH(CH$_2$OCOR$^b$)—, —CH(NHC(O)R$^b$)—, —(CH$_2$)$_x$—C(O)—, —(CH$_2$)$_x$—C(NOR$^b$)—, —CH(OSO$_2$NH$_2$)—, —O— or —S—; where x is 0 or 1, $R^b$ represents H or $C_{1-6}$alkyl or $C_{2-6}$alkenyl, either of which is optionally substituted with halogen, CN, NO$_2$, CF$_3$, OH, CO$_2$H, $C_{1-4}$alkoxy or $C_{1-4}$alkoxycarbonyl, and $R^c$ represents $R^b$ or tris($C_{1-6}$alkyl)silyl;

$R^1$ represents H, $C_{1-6}$alkyl, $C_{3-8}$cycloalkyl, $C_{2-6}$alkenyl, $C_{2-6}$alkynyl or polyfluoro$C_{1-6}$alkyl, said alkyl, cycloalkyl, alkenyl and alkynyl groups being optionally substituted by halogen, —CN, —NO$_2$, aryl, heteroaryl, —COR$_6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$; or when X is N—$R^a$, $R^1$ together with $R^a$ completes a fused imidazole or 4,5-dihydroimidazole ring;

$R^2$ represents $C_{1-6}$alkyl, $C_{3-6}$cycloalkyl, $C_{2-6}$alkenyl, $C_{2-6}$alkynyl, polyfluoro$C_{1-6}$alkyl, aryl, heteroaryl, —OR$^7$, or —Oaryl, said alkyl, cycloalkyl, alkenyl and alkynyl groups optionally being substituted by halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$;

$R^{2a}$ represents H or $C_{1-6}$alkyl;

or $R^2$ and $R^{2a}$ together complete a $C_{3-6}$cycloalkyl group;

$R^3$ represents aryl or heteroaryl;

$R^4$ represents H, halogen, —CN, $C_{1-10}$alkyl, $C_{3-10}$cycloalkyl, $C_{2-10}$alkenyl, $C_{2-10}$alkynyl, aryl, heteroaryl, —OR$^8$ or —N(R$^8$)$_2$, said alkyl, cycloalkyl, alkenyl and alkynyl groups optionally being substituted by halogen, —CN, —NO$_2$, aryl, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ or —N(R$^6$)$_2$;

$R^5$ represents H, $C_{1-6}$alkyl or benzyl which optionally bears up to 3 substituents independently selected from halogen, —CN, —NO$_2$, —OH and methoxy;

each $R^6$ independently represents H, polyfluoro$C_{1-6}$alkyl, or $C_{1-6}$alkyl which is optionally substituted with halogen, —CN, —NO$_2$, —OH, —SH, —NH$_2$, phenyl, morpholin-4-yl, thiomorpholin-4-yl, piperidin-1-yl, piperazin-1-yl, pyrrolidin-1-yl, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$; or two $R^6$ groups attached to a single nitrogen atom may complete a heterocyclic ring or condensed ring system of from 3 to 12 members including the said nitrogen, the remaining atoms being selected from C, N, O and S and the ring or condensed ring system optionally bearing up to 3 substituents independently selected from $C_{1-6}$alkyl, polyfluoro$C_{1-6}$alkyl, $C_{2-7}$acyl, —OH and —CONH$_2$;

$R^7$ represents $R^6$ that is other than H;

$R^8$ represents $R^6$, aryl or heteroaryl;

$R^9$ represents aryl, heteroaryl, $C_{3-6}$cycloalkyl or —OR$^7$;

"aryl" refers to phenyl which is optionally fused to a 5–7 membered saturated or unsaturated ring which may be carbocyclic or may comprise up to 3 heteroatoms selected from nitrogen, oxygen and sulphur, and which may be oxo-substituted, said phenyl and optional fused ring together bearing 0–3 substituents independently selected from $C_{1-6}$alkyl [which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$], polyfluoro$C_{1-6}$alkyl, halogen, —CN, —NO$_2$, heteroaryl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

"heteroaryl" refers to a heteroaromatic ring of 5 or 6 members, at least one member being nitrogen, oxygen or sulphur and the remainder carbon, said ring optionally being fused to a 5–7 membered saturated or unsaturated ring which may be carbocyclic or may comprise up to 3 heteroatoms selected from nitrogen, oxygen and sulphur, and which may be oxo-substituted, the heteroaromatic ring and optional fused ring together bearing 0–3 substituents independently selected from $C_{1-6}$alkyl which is optionally substituted with halogen, —CN, —NO$_2$, —OH, —SH, —NH$_2$, $C_{1-4}$alkoxy, $C_{1-4}$alkylthio, $C_{1-4}$alkylamino, di($C_{1-4}$alkyl)amino, —CO$_2$H, —CO$_2$C$_{1-4}$alkyl, —CONH$_2$, —CONHC$_{1-4}$alkyl or —CON(C$_{1-4}$alkyl)$_2$, polyfluoro$C_{16}$alkyl, halogen, —CN, —NO$_2$, phenyl, —COR$^6$, —CO$_2$R$^6$, —CON(R$^6$)$_2$, —OCOR$^7$, —NR$^6$COR$^7$, —NR$^6$SO$_2$R$^7$, —SO$_3$R$^6$, —SO$_2$N(R$^6$)$_2$, —OR$^6$, —SR$^6$ and —N(R$^6$)$_2$;

or a pharmaceutically acceptable salt thereof.

* * * * *